(12) United States Patent
Petrecca et al.

(10) Patent No.: US 8,765,708 B2
(45) Date of Patent: Jul. 1, 2014

(54) METHOD FOR REDUCING EXPRESSION OF DOWNREGULATED IN RENAL CELL CARCINOMA IN MALIGNANT GLIOMAS

(76) Inventors: Kevin Petrecca, Verdun (CA); Masad Damha, St-Hubert (CA); Glen Francis Deleavey, Montreal (CA)

(*) Notice: Subject to any disclaimer, the term of this patent is extended or adjusted under 35 U.S.C. 154(b) by 0 days.

(21) Appl. No.: 13/698,429

(22) PCT Filed: May 18, 2011

(86) PCT No.: PCT/CA2011/000591
§ 371 (c)(1),
(2), (4) Date: Mar. 20, 2013

(87) PCT Pub. No.: WO2011/143762
PCT Pub. Date: Nov. 24, 2011

(65) Prior Publication Data
US 2013/0197057 A1 Aug. 1, 2013

Related U.S. Application Data

(60) Provisional application No. 61/345,751, filed on May 18, 2010.

(51) Int. Cl.
*C12N 15/11* (2006.01)
*C12Q 1/68* (2006.01)
*C12N 15/113* (2010.01)

(52) U.S. Cl.
CPC .................................. *C12N 15/113* (2013.01)
USPC ........................................ 514/44 A; 435/6.1

(58) Field of Classification Search
None
See application file for complete search history.

(56) References Cited

U.S. PATENT DOCUMENTS

2005/0244851 A1 11/2005 Blume et al.
2006/0134663 A1* 6/2006 Harkin et al. ..................... 435/6

OTHER PUBLICATIONS

Asano et al, DRR1 is expressed in the developing nervous system and downregulated during neuroblastoma carcinogenesis, Apr. 2010, Biochemical and Biophysical Research Communications, vol. 394, 3: 829-835.*
Le, P. U. et al. DRR drives brain cancer invasion by regulating cytoskeletal-focal adhesion dynamics. Oncogene. Jun. 14, 2010, vol. 29, No. 33, pp. 4636-4647, ISSN 1476-5594.
Wang, L. at al. Loss of expression of the DRR 1 gene at chromosomal segment 3p21.1 in renal cell carcinoma. Genes. Chromosomes & Cancer. Jan. 2000, vol. 27, No. 1, pp. 1-10, ISSN 1098-2264.
Van Den Boom, J. et al. Identification of novel genes associated with astrocytoma progression using suppression subtractive hybridization and real-time reverse transcription-polymerase chain reaction. Int. J. Cancer. Nov. 15, 2006, vol. 119, No. 10, pp. 2330-2338, ISSN 1097-0215.
International Search Report, International Application No. PCT/CA2011/000591, mailed Sep. 2, 2011.

* cited by examiner

*Primary Examiner* — Tracy Vivlemore
*Assistant Examiner* — Kate Poliakova-Georgantas
(74) *Attorney, Agent, or Firm* — Norton Rose Fulbright Canada

(57) ABSTRACT

The present invention relates to novel compositions and therapeutic methods for the treatment of cancer, in particular malignant glioma. The compositions include antisense oligonucleotides or RNAs or vectors encoding them which reduce expression of downregulated in renal cell carcinoma (DRR) in tumor cells, and inhibit malignant glioma cell invasion.

17 Claims, 24 Drawing Sheets

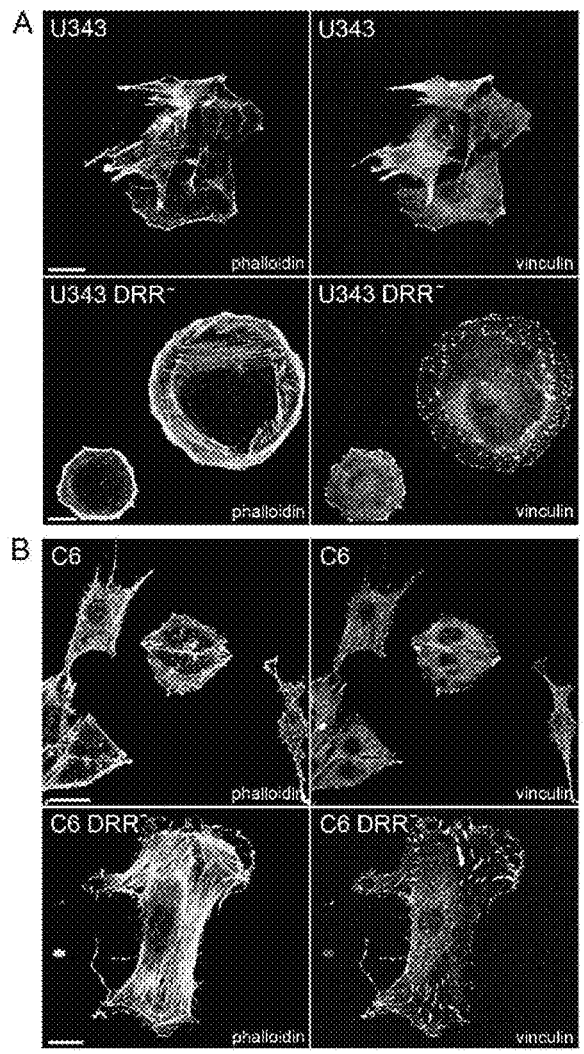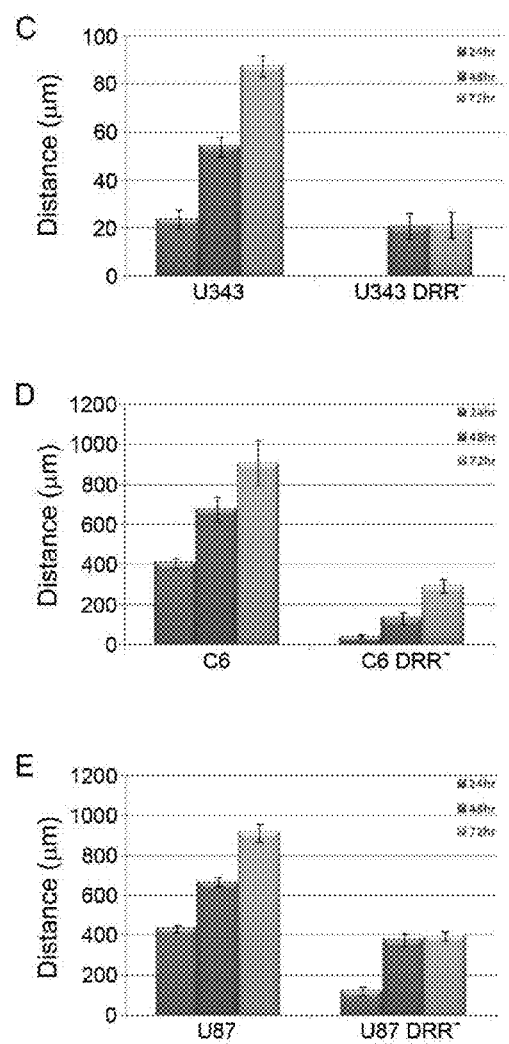
FIGURE 11

FIGURE 13

```
                             SEQUENCE LISTING

<160> NUMBER OF SEQ ID NOS: 16

<210> SEQ ID NO 1
<211> LENGTH: 29
<212> TYPE: DNA
<213> ORGANISM: Artificial sequence
<220> FEATURE:
<223> OTHER INFORMATION: primer

<400> SEQUENCE: 1
gctctctctc ttcgccggcc aatgcggca                                       29

<210> SEQ ID NO 2
<211> LENGTH: 15
<212> TYPE: DNA
<213> ORGANISM: Artificial sequence
<220> FEATURE:
<223> OTHER INFORMATION: antisense

<400> SEQUENCE: 2
gctctctctc ttcgc                                                      15

<210> SEQ ID NO 3
<211> LENGTH: 15
<212> TYPE: DNA
<213> ORGANISM: Artificial sequence
<220> FEATURE:
<223> OTHER INFORMATION: sense sequence

<400> SEQUENCE: 3
gcgaagagag agagc                                                      15

<210> SEQ ID NO 4
<211> LENGTH: 435
<212> TYPE: DNA
<213> ORGANISM: Artificial sequence
<220> FEATURE:
<223> OTHER INFORMATION: DRR sequence

<400> SEQUENCE: 4
atgtactcgg agatccagag ggagcgggca gacattgggg gcctgatggc ccggccagaa     60
tacagagagt ggaatccgga gctcatcaag cccaagaagc tgctgaaccc cgtgaaggcc    120
tctcggagtc accaggagct ccaccgggag ctgctcatga accacagaag gggccttggt    180
gtggacagca agccagagct gcagcgtgtc ctagagcacc gccggcggaa ccagctcatc    240
aagaagaaga aggaggagct ggaagccaag cggctgcagt gccccttga gcaggagctg     300 ctgagacggc agcagaggct gaaccagctg gaaaaccac cagagaagga agaggatcac    360
gcccccgagt ttattaaagt cagggaaaac ctgcggagaa ttgccacact gaccagcgaa   420
gagagagagc tttaa                                                     435

<210> SEQ ID NO 5
<211> LENGTH: 16
<212> TYPE: DNA
<213> ORGANISM: Artificial sequence
<220> FEATURE:
<223> OTHER INFORMATION: antisense
```

-continued

```
<400> SEQUENCE: 5
gctctctctc ttcgct                                                   16

<210> SEQ ID NO 6
<211> LENGTH: 17
<212> TYPE: DNA
<213> ORGANISM: Artificial sequence
<220> FEATURE:
<223> OTHER INFORMATION: antisense

<400> SEQUENCE: 6
gctctctctc ttcgctg                                                  17

<210> SEQ ID NO 7
<211> LENGTH: 18
<212> TYPE: DNA
<213> ORGANISM: Artificial sequence
<220> FEATURE:
<223> OTHER INFORMATION: antisense

<400> SEQUENCE: 7
gctctctctc ttcgctgg                                                 18

<210> SEQ ID NO 8
<211> LENGTH: 19
<212> TYPE: DNA
<213> ORGANISM: Artificial sequence
<220> FEATURE:
<223> OTHER INFORMATION: antisense

<400> SEQUENCE: 8
gctctctctc ttcgctggt                                                19

<210> SEQ ID NO 9
<211> LENGTH: 20
<212> TYPE: DNA
<213> ORGANISM: Artificial sequence
<220> FEATURE:
<223> OTHER INFORMATION: antisense

<400> SEQUENCE: 9
gctctctctc ttcgctggtc                                               20

<210> SEQ ID NO 10
<211> LENGTH: 15
<212> TYPE: DNA
<213> ORGANISM: Artificial sequence
<220> FEATURE:
<223> OTHER INFORMATION: antisense

<400> SEQUENCE: 10
ctctcttcgc tggtc                                                    15

<210> SEQ ID NO 11
<211> LENGTH: 21
<212> TYPE: DNA
<213> ORGANISM: Artificial sequence
<220> FEATURE:
<223> OTHER INFORMATION: antisense with FANA nucleotides
<220> FEATURE:
<221> NAME/KEY: modified_base
<222> LOCATION: (1)..(3)
<223> OTHER INFORMATION: 2'- fluoroarabinonucleotide
<220> FEATURE:
<221> NAME/KEY: modified_base
<222> LOCATION: (7)..(9)
```

-continued

<223> OTHER INFORMATION: 2'- fluoroarabinonucleotide
<220> FEATURE:
<221> NAME/KEY: modified_base
<222> LOCATION: (13)..(15)
<223> OTHER INFORMATION: 2'- fluoroarabinonucleotide
<220> FEATURE:
<221> NAME/KEY: modified_base
<222> LOCATION: (19)..(21)
<223> OTHER INFORMATION: 2'- fluoroarabinonucleotide

<400> SEQUENCE: 11
ttccttggtc gagtagttct t       21

<210> SEQ ID NO 12
<211> LENGTH: 21
<212> TYPE: DNA
<213> ORGANISM: Artificial sequence
<220> FEATURE:
<223> OTHER INFORMATION: antisense with FANA nucleotides
<220> FEATURE:
<221> NAME/KEY: modified_base
<222> LOCATION: (1)..(6)
<223> OTHER INFORMATION: 2'- fluoroarabinonucleotide
<220> FEATURE:
<221> NAME/KEY: modified_base
<222> LOCATION: (16)..(21)
<223> OTHER INFORMATION: 2'- fluoroarabinonucleotide

<400> SEQUENCE: 12
ttccttggtc gagtagttct t       21

<210> SEQ ID NO 13
<211> LENGTH: 18
<212> TYPE: DNA
<213> ORGANISM: Artificial sequence
<220> FEATURE:
<223> OTHER INFORMATION: antisense with FANA nucleotides
<220> FEATURE:
<221> NAME/KEY: modified_base
<222> LOCATION: (1)..(6)
<223> OTHER INFORMATION: 2'- fluoroarabinonucleotide
<220> FEATURE:
<221> NAME/KEY: modified_base
<222> LOCATION: (13)..(18)
<223> OTHER INFORMATION: 2'- fluoroarabinonucleotide

<400> SEQUENCE: 13
atatccttgt cgtatccc       18

<210> SEQ ID NO 14
<211> LENGTH: 20
<212> TYPE: DNA
<213> ORGANISM: Artificial sequence
<220> FEATURE:
<223> OTHER INFORMATION: antisense with FANA nucleotides
<220> FEATURE:
<221> NAME/KEY: modified_base
<222> LOCATION: (1)..(3)
<223> OTHER INFORMATION: 2'- fluoroarabinonucleotide
<220> FEATURE:
<221> NAME/KEY: modified_base
<222> LOCATION: (7)..(9)
<223> OTHER INFORMATION: 2'- fluoroarabinonucleotide
<220> FEATURE:
<221> NAME/KEY: modified_base
<222> LOCATION: (13)..(15)
<223> OTHER INFORMATION: 2'- fluoroarabinonucleotide
<220> FEATURE:
<221> NAME/KEY: modified_base
<222> LOCATION: (19)..(20)
<223> OTHER INFORMATION: 2'- fluoroarabinonucleotide

<400> SEQUENCE: 14

```
aatgtctgcc cgctccctct                                                    20

<210> SEQ ID NO 15
<211> LENGTH: 20
<212> TYPE: DNA
<213> ORGANISM: Artificial sequence
<220> FEATURE:
<223> OTHER INFORMATION: antisense with FANA nucleotides
<220> FEATURE:
<221> NAME/KEY: modified_base
<222> LOCATION: (1)..(6)
<223> OTHER INFORMATION: 2'- fluoroarabinonucleotide
<220> FEATURE:
<221> NAME/KEY: modified_base
<222> LOCATION: (16)..(20)
<223> OTHER INFORMATION: 2'- fluoroarabinonucleotide

<400> SEQUENCE: 15
aatgtctgcc cgctccctct                                                    20

<210> SEQ ID NO 16
<211> LENGTH: 20
<212> TYPE: DNA
<213> ORGANISM: Artificial sequence
<220> FEATURE:
<223> OTHER INFORMATION: antisense

<400> SEQUENCE: 16
aatgtctgcc cgctccctct                                                    20
```

METHOD FOR REDUCING EXPRESSION OF DOWNREGULATED IN RENAL CELL CARCINOMA IN MALIGNANT GLIOMAS

RELATED APPLICATIONS

This application claims priority to U.S. provisional application no. 61/345,751 filed May 18, 2010, which is hereby incorporated by reference in its entirety.

FIELD OF THE INVENTION

This invention relates to novel pharmaceutical compositions and methods for treating malignant glioma.

BACKGROUND OF THE INVENTION

Gliomas arise from the supporting cells of the brain, called the glia. These cells are subdivided into astrocytes, ependymal cells and oligodendroglial cells. Gliomas are the most common primary brain cancers and are amongst the most devastating of human malignancies. The tumors are graded from the lowest grade 1 to highest grade 4, with glioblastoma multiforme (GBM) being the highest grade and deadliest type of glioma. High-grade glioma or GBM is the most common primary malignant brain tumor, as well as the most devastating, accounting for 19 percent of all primary brain tumors.

Benign gliomas, known as pilocytic astrocytomas, are seen in children and are very well treated by complete surgical resection, with patients typically maintaining a full life expectancy. In contrast, high-grade or malignant gliomas, known as astrocytomas, oligodendrogliomas or glioblastomas, are adult neoplasms characterized by brain invasion. Unlike benign gliomas, which do not invade normal brain, malignant gliomas are highly invasive. As a rule, high-grade gliomas almost always grow back even after complete surgical excision.

Malignant gliomas can be further divided into low grade and high grade. Low grade malignant gliomas are highly invasive but have low proliferation rates, often invading multiple lobes prior to clinical presentation. Over time, low grade malignant gliomas may incur genetic changes that increase their proliferation rate and convert them to a higher grade (Louis, D. N. et al., *Cancer Cell* 1:125-128, 2002).

The prognosis for patients with high-grade gliomas is generally poor. Malignant gliomas are among the most challenging of all cancers to treat successfully because they are characterized not only by aggressive proliferation and expansion, but also by their aggressive invasion of distant brain tissue. Of approximately 10,000 Americans diagnosed each year with malignant gliomas, about half are alive 1 year after diagnosis, and 25% after two years. Those with anaplastic astrocytoma survive about three years. Glioblastoma multiforme has a worse prognosis with less than 12 month survival after diagnosis. Standard treatment includes surgical resection followed by chemotherapy and radiation therapy. Unfortunately, this multimodal approach still translates to a mean survival of only 12 to 14 months. Gliomas cannot be cured.

One desirable approach to managing this devastating cancer would be to inhibit malignant glial cell (MGC) invasion. Maintaining MGCs in a local environment leaves further treatment options open. However, there are currently no therapeutic strategies available for the inhibition of brain cancer invasion.

Many molecules have been implicated in malignant glioma invasion, however the molecular mechanisms underlying the process are not well understood. The current understanding of cell invasion is a composite derived from studies of different cell types and environments. Cell invasion involves the extension of a cellular process, attachment through focal adhesion (FA) formation, degradation of the extracellular matrix to create space to accommodate the moving cell, translocation of the cell body forward, and release of cell rear FAs (Friedl and Wolf, *Nat Rev Cancer* 3:362-74, 2003). This multistep process requires the coordinated action of cell surface receptors, signaling pathways, cytoskeletal elements, FA components, and extracellular matrix degrading enzymes (Burridge and Chrzanowska-Wodnicka, *Annu. Rev. Cell. Dev. Biol.* 12:463-519, 1996; Lauffenburger and Horwitz, *Cell* 84:359-369, 1996; Ridley et al., *Science* 302:1704-9, 2003). Within this scheme, recent studies have pointed to the importance of actin/microtubule (MT) dynamics in both cell front membrane protrusion and cell rear retraction (Palazzo and Gundersen, *Sci. STKE* 2002:PE31, 2002; Rodriguez et al., *Nature Cell Biology* 7:599-609. 2003). Cell rear retraction requires regulated FA disassembly and the actin/MT system plays a key role in the process.

While there are many similarities between cell movement in normal physiologic conditions and in cancer, MGCs are thought to utilize additional or alternate mechanisms (Beadle et al., *Mol Biol Cell.* 19:3357-68.2008). Recent studies have suggested that MGCs invade the dense substance of the brain using a mode of cell movement that is similar to neural progenitor cell movement.

The "down regulated in renal cell carcinoma (DRR1)" gene (also known as TU3A, and referred to herein as DRR, DRR-1 and DRR1 interchangeably) was originally cloned from the short arm of chromosome 3 from patients with renal cell carcinoma (Wang et al., *Genes Chromosomes & Cancer* 27:1-10, 2000). Wang et al. reported that the gene showed significant loss of expression in renal cell carcinoma (RCC) cell lines, as well as in primary tumours, and that transfection of the gene into DRR negative cell lines resulted in growth suppression, suggesting a role as a tumour suppressor for DRR. The function of the DRR gene product is not known. The gene sequence predicts a protein of 144 amino acids with a nuclear localization signal and a coiled domain. A putative role for downregulation of DRR1 gene expression in glioma progression has also been suggested by van den Boom et al. (van den Boom et al., *Int. J. Cancer* 119: 2330-2338, 2006), who reported that DRR1 gene expression is reduced in glioblastomas as compared to diffuse astrocytomas.

There is a need for inhibitors of brain cancer invasion and for new therapeutic approaches for the treatment of glioma, as well as for inhibitors of DRR.

SUMMARY OF THE INVENTION

We report herein the identification of a protein, "down regulated in renal cell carcinoma" or "DRR", as a novel therapeutic target for the treatment of brain cancer. We show here that DRR is a novel regulator of brain cancer invasion. DRR drives MGC invasion in both in vitro and in vivo invasion assays, and DRR interaction with actin and microtubules (MTs) is essential for focal adhesion (FA) disassembly and cell invasion. Moreover, DRR is not expressed in normal human brain glia, but is highly expressed in the invasive component of malignant gliomas, indicating a strong correlation between DRR expression in malignant gliomas and invasion. These findings are novel and unexpected, particularly in view of previous reports identifying a role for DRR as a tumour suppressor (Wang et al., *Genes Chromosomes & Cancer* 27:1-10, 2000; van den Boom et al., *Int. J. Cancer* 119: 2330-2338, 2006).

Taken together, our findings identify DRR as a novel regulator of brain cancer invasion and a target for therapeutic intervention in the treatment of glioma.

Accordingly, there are provided herein compositions and methods for the treatment of glioma, comprising nucleic acid molecules effective at reducing the expression of DRR in tumor cells. The nucleic acid molecules of the invention include, for example, therapeutic RNAs or therapeutic oligonucleotides such as antisense oligonucleotides, antisense RNAs, or vectors which encode antisense oligonucleotides or antisense RNAs.

In an embodiment, there is provided herein a method for reducing the expression of downregulated in renal cell carcinoma (DRR) in tumor cells, comprising providing a therapeutic antisense molecule comprising the sequence of SEQ ID NOs: 1, 2, 5, 6, 7, 8, 9, 10, 14, 15 or 16, or a fragment or derivative thereof, to tumor cells, wherein the antisense molecule reduces the expression of DRR in the tumor cells.

In another embodiment, there is provided an antisense molecule for reducing the expression of downregulated in renal cell carcinoma (DRR) in tumor cells, comprising the sequence of SEQ ID NO: 1, 2, 5, 6, 7, 8, 9, 10, 14, 15 or 16, or a fragment or derivative thereof.

In yet another embodiment, there is provided a method for reducing the expression of downregulated in renal cell carcinoma (DRR) in tumor cells, comprising providing to tumor cells a DNA molecule comprising a sequence which encodes the sequence of SEQ ID NO: 1, 2, 5, 6, 7, 8, 9, 10, 14, 15 or 16 or a fragment or derivative thereof suitable for reducing the expression of DRR in the tumor cells. In some embodiments, the DNA molecule is inserted in an expression vector suitable for the production of a therapeutic molecule, e.g. an antisense oligonucleotide or RNA, of the invention. The expression vector may, for example, comprise a sequence encoding the sequence of SEQ ID NO: 1, 2, 5, 6, 7, 8, 9, 10, 14, 15 or 16, or a fragment or derivative thereof.

There are also provided herein methods of treating cancer comprising administering the antisense molecules described herein or a vector that encodes them to a subject in need thereof. Methods of delaying the progression of cancer comprising administering the antisense molecules described herein or a vector that encodes them to a subject in need thereof are also provided.

In some embodiments, the antisense molecules and/or the vectors described herein may be used in combination with one or more cancer therapies selected from the group consisting of surgical resection, chemotherapy, radiation therapy, immunotherapy, and gene therapy.

In certain embodiments, the tumor cells are glioma cells, such as malignant glioma cells or glioblastoma cells.

In an embodiment, there is a provided a pharmaceutical composition for the treatment of cancer comprising an antisense molecule of the invention, or a vector that encodes the antisense molecule of the invention, and a pharmaceutically acceptable carrier. In one embodiment, the cancer is glioma, in particular malignant glioblastoma.

In another embodiment, there is provided a kit comprising the pharmaceutical compositions of the invention, and instructions for use thereof. The kits provided herein may further comprise a second active compound suitable for treating glioma and/or for delaying the progression thereof, for simultaneous, separate or sequential administration to a subject.

The present invention also provides a method for enhancing the efficacy of a cancer therapy for the treatment of glioma, comprising administering an antisense molecule of the invention or a vector that encodes the antisense molecule to a subject in need thereof, and simultaneously, separately or sequentially administrating a second cancer therapy. The second cancer therapy may be, for example, surgical resection, chemotherapy, radiation therapy, immunotherapy, and/or gene therapy.

Further provided herein is a method for inhibiting malignant glial cell invasion in a subject in need thereof, comprising providing to tumor cells an antisense molecule of the invention, or a fragment or derivative thereof, wherein the antisense molecule reduces the expression of DRR in the tumor cells. In an embodiment, malignant glial cell invasion is inhibited in a subject by providing to tumor cells a DNA molecule comprising the sequence encoding SEQ ID NO: 1, 2, 5, 6, 7, 8, 9, 10, 14, 15 or 16 or a fragment or derivative thereof, wherein the DNA encodes an antisense molecule suitable for reducing the expression of DRR in the tumor cells.

In an embodiment, a method for diagnosis or prognosis of glioma in a subject, comprising measuring DRR expression in the glioma cells of the subject, wherein DRR expression indicates invasiveness of the cells, is provided. In another embodiment, a method for visualizing invasive glioma cells in a subject, comprising contacting glioma cells with a molecule which specifically binds DRR protein or mRNA and measuring DRR protein or mRNA levels in the cells, wherein cells which express DRR are invasive, is provided.

In yet another embodiment, there is provided a kit for diagnosis or prognosis of invasive glioma in a subject, comprising a detectably-labelled probe specific for DRR RNA or protein, a reporter means for detecting binding of the probe to the DRR RNA or protein, and instructions for use thereof.

In an embodiment, there is a provided a method for treating cancer comprising administering a therapeutic nucleic acid, e.g. an antisense molecule, which reduces the expression of DRR, or a vector encoding the therapeutic molecule to a subject in need thereof. In some embodiments, the progression of the cancer is delayed, malignant cell invasion is inhibited, and/or malignant glial cell invasion is inhibited. In an embodiment, the cancer is glioma, preferably malignant glioma, and more preferably glioblastoma. In an embodiment, the therapeutic oligonucleotide(s) which reduces the expression of DRR is complementary to or specifically hybridizes to DRR mRNA, or a fragment or derivative thereof.

It should be understood that the invention is not meant to be limited to the specific therapeutic nucleic acids recited herein; rather, use of any nucleic acid which functions to reduce the expression of DRR in the compositions and methods of the invention is contemplated. In particular, therapeutic oligonucleotides (e.g. antisense RNA, antisense oligonucleotides, aptamers or ribozymes) complementary to, or specifically hybridizing to a region of DRR, e.g. a region, fragment, portion or derivative of the DRR mRNA, and which reduce expression of DRR, are encompassed. DNAs or vectors encoding the therapeutic oligonucleotides of the invention are also encompassed herein. Nucleic acids aptamers, which are sequences that adopt a unique three-dimensional structure that recognize (binds to) DRR through protein-nucleic acid interactions, are also encompassed herein.

BRIEF DESCRIPTION OF THE DRAWINGS

Having thus generally described the nature of the invention, reference will now be made to the accompanying drawings, showing by way of illustration, an embodiment or embodiments thereof, and in which:

FIG. 11 shows that DRR regulates focal adhesion dynamics and invasion in multiple glioma cell lines. Control U343 or U343-DRR⁻ cells (A) and control C6 or C6-DRR⁻ cells (B) were colabeled for actin (phalloidin) and FAs (vinculin). Control cells contain small FAs whereas cells with reduced DRR expression contain large FAs. Bars=20 µm. Reduced DRR expression in U343 (C), C6 (D), and U87 (E) glioma cells leads to a significant reduction in invasiveness in a 3D invasion assay.

FIG. 13 shows a comparison of amino acid sequences within regions required for DRR-actin association across species.

DETAILED DESCRIPTION

Figure 1:
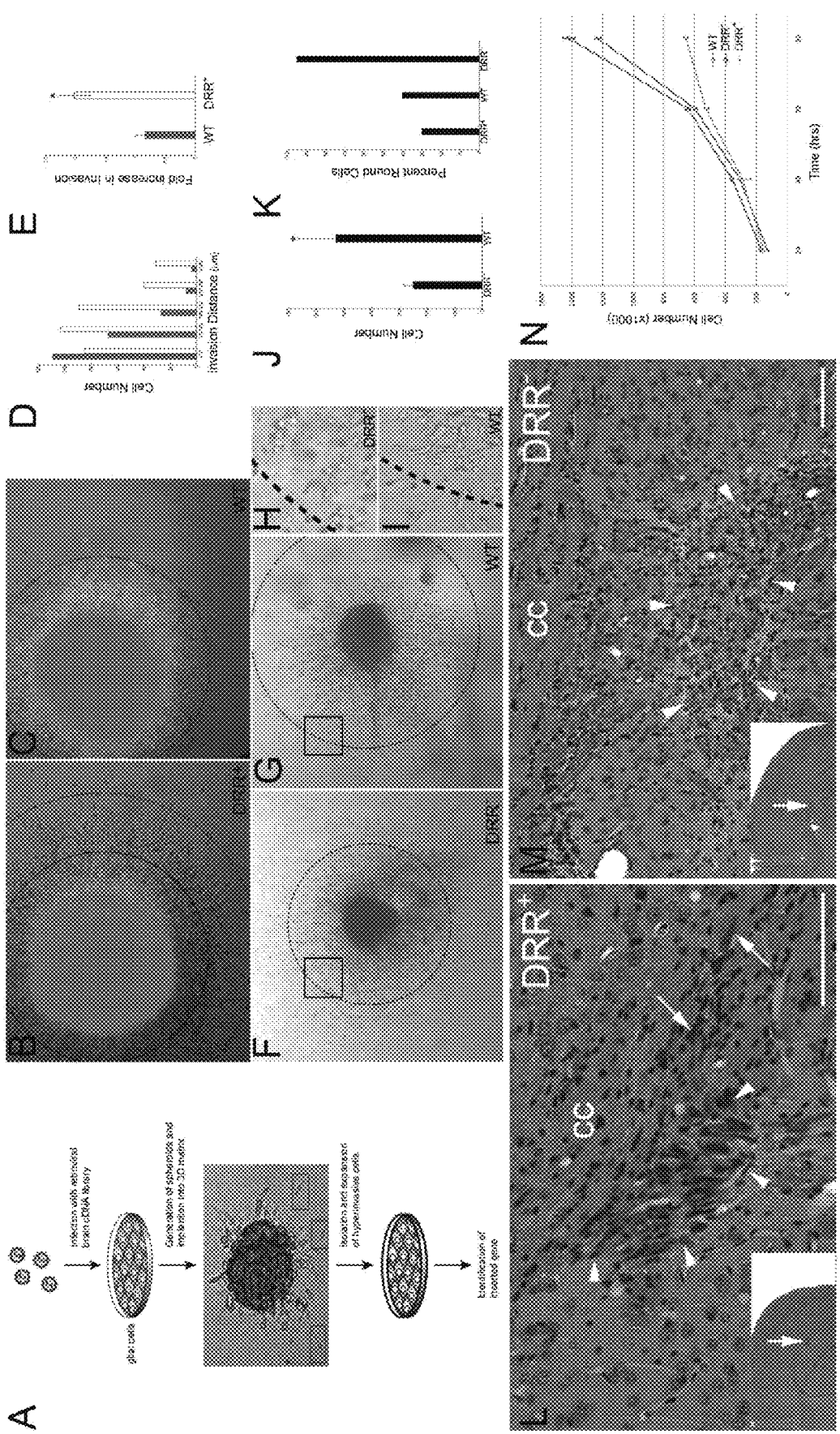
FIG. 1 shows the validation of DRR as a regulator of invasion, wherein: (A) shows and outline of a functional genetic screening assay; (B) shows a mixed tumor spheroid containing WT glial cells (cytotracker red label) and DRR overexpressing cells (DRR+, transparent) showing hyperinvasion of DRR+ cells; solid circle demarcates invasion front of WT cells, and dashed circle demarcates invasion front of DRR+ cells; (C) shows control mixed tumor spheroid showing equal invasion of WT cytotracker red labeled cells and WT unlabelled cells demonstrating that cytotracker red labeling does not influence invasion; (D) shows quantitative analysis of invasion; (E) shows quantification of maximal invasion of WT—(red bars) and DRR+—(empty bars) cells; data are mean±s.e.m. (n=14 for each cell line); asterisk, $P<0.001$; (F) shows tumor spheroid generated from DRR− cells, wherein circle demarcates invasion front; (G) shows tumor spheroid generated from WT cells, wherein circle demarcates invasion front; (H) shows high magnification image of inset in (F), showing that DRR− cells have a round cell shape; (I) shows high magnification image of inset in (G), showing that WT cells have an elongated cell shape; (J) shows quantification of cell invasion comparing DRR− cells and WT cells; Cells invading greater than 400 µm were counted; data are mean±s.e.m. (n=8 for each cell line); asterisk, $P<0.001$; (K) shows quantification of the effect of DRR expression on cell shape showing that DRR expression promotes an elongated cell shape; (L) shows DRR cells implanted into mouse brain showing elongated cell shape and invasion into corpus callosum (cc), wherein arrows indicate MGCs that have invaded the corpus callosum, arrowheads delineate tumor border, arrow in inset indicates tumor implantation site, bar=100 µm; (M) shows DRR− cells implanted into mouse brain showing round cell shape and no evidence of invasion towards the corpus callosum, wherein arrowheads delineate tumor border and arrow in inset indicates tumor implantation site, bar=100 µm; and (N) shows quantification of cell proliferation in DRR+, WT, and DRR− cells.

The present invention relates to the identification of down-regulated in renal carcinoma (referred to herein as DRR, DRR1 or DRR-1) as a novel regulator of brain cancer invasion and a target for therapeutic intervention in the treatment of glioma, particularly malignant glioblastoma. In particular, there are provided herein novel compounds, pharmaceutical compositions and methods for inhibiting glioma tumor cell invasion and/or treating glioma comprising molecules which reduce the expression of DRR in glioma tumor cells.

The present invention thus provides compounds, in particular oligonucleotides and similar species, for use in modulating the function or effect of nucleic acid molecules encoding DRR. In some embodiments, this is accomplished by providing oligonucleotides which specifically hybridize with one or more nucleic acid molecules encoding DRR. A compound of this invention which hybridizes with its target nucleic acid is generally referred to as "antisense" and consequently, the mechanism of inhibition of DRR is referred to as "antisense inhibition." Such antisense inhibition is typically based upon hydrogen bonding-based hybridization of oligonucleotide strands or segments such that the target RNA molecule is cleaved, degraded, or otherwise rendered inoperable. The present invention is concerned with targeting specific nucleic acid molecules which encode for DRR or a portion thereof, such as the mRNA encoding DRR.

As used herein, "hybridization" refers to the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances. "Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

An antisense compound is specifically hybridizable when binding of the compound to the target nucleic acid, e.g. DRR mRNA, interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense compounds of the present invention comprise at least 70% sequence complementarity to a target region within the target nucleic acid, more preferably that they comprise at least 80% sequence complementarity, at least 85% sequence complementarity, at least 90% sequence complementarity or at least 95% sequence complementarity to the target nucleic acid sequence. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol. 215: 403-410, 1990; Zhang and Madden, Genome Res. 7: 649-656, 1997).

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated. A non-limiting example of a hybridization condition is hybridization in 6×SSC buffer (900 mM sodium chloride containing 90 mM sodium citrate at pH 7.0) containing 50% formamide, 0.5% sodium dodecyl sulfate and blocking reagents, carried out at 42° C. for 16 hours. Membranes are then washed twice with I×SSC containing 0.1% SDS at room temperature, then O. I×SSC containing 0. 1% SDS at room temperature, and finally O. I×SSC containing 0.5% SDS at 42° C.

Antisense drugs are typically small (e.g. 12-21 nucleotides, or 15-30 nucleotides) pieces of DNA or RNA that are chemically modified to engineer good drug properties. Antisense drugs work after binding (hybridizing) to a target RNA and forming a duplex. The formation of this duplex, or two-stranded molecule, prevents the RNA from functioning normally and/or from producing a protein. Antisense oligonucleotides inhibit mRNA translation via a number of alternative mechanisms including destruction of the target mRNA through RNaseH recruitment, interference with RNA processing or translation, nuclear export, folding or ribosome scanning. There are at least a dozen known antisense mechanisms that may be exploited once an antisense drug binds to its target RNA. For example, therapeutic molecules may target non-coding RNAs, such as microRNAs, which are involved in the regulation of protein production within the cell. MicroRNAs are small naturally occurring RNA molecules that are created inside cells and appear to have critical functions in controlling processes or pathways of gene expression. There are nearly 700 microRNAs that have been identified in the human genome, and these are believed to regulate the expression of approximately one-third of all human genes. Other antisense drugs may for example control splicing, to favour production of one protein versus another.

Many different types of antisense oligonucleotides are known and may be used in the compositions and methods of the invention. It is contemplated that any of the known antisense technologies may be used to target DRR and reduce DRR expression. For example, oligonucleosides having alternating segments of sugar-modified nucleosides (e.g., 2'-O-modified ribonucleosides or arabinonucleosides) and 2'-deoxynucleosides, and/or oligonucleotides having alternating segments of sugar-modified nucleotides and 2'-deoxynucleotides, are known as "altimers" and may be used for the preparation of antisense oligonucleotides.

Altimers are described in, for example, PCT publication no. WO/2003/064441, the contents of which are hereby incorporated by reference. In one embodiment, the therapeutic molecule of the invention is an antisense comprising an oligonucleoside comprising alternating segments of sugar-modified nucleosides and 2'-deoxynucleosides, wherein the segments or units each independently comprise at least one sugar-modified nucleoside or 2'-deoxynucleoside, respectively. For example, the oligonucleoside comprises alternating first and second segments, wherein the first segment comprises at least one sugar-modified nucleoside, and wherein the second segment comprises at least one 2'-deoxynucleoside. In embodiments, the oligonucleoside comprises at least 2 of each of the first and second segments thereby comprising at least 4 alternating segments.

In an embodiment, the oligonucleoside comprises an internucleoside linkage comprising a phosphate, thereby being an oligonucleotide. In embodiments the sugar-modified nucleosides and/or 2'-deoxynucleosides comprise a phosphate, thereby being sugar-modified nucleotides and/or 2'-deoxynucleotides. Thus in an embodiment, the invention provides an oligonucleotide comprising alternating segments or units of arabinonucleotides and 2'-deoxynucleotides, wherein said segments or units each independently comprise at least one arabinonucleotide or 2'-deoxynucleotide, respectively. In an embodiment, the oligonucleotide comprises at least 2 arabinonucleotide segments and at least 2 2'-deoxynucleotide segments thereby having at least 4 of the alternating units.

In an embodiment, the sugar-modified oligonucleotide is capable of adopting a DNA-like conformation. In an embodiment, the sugar-modified nucleotide is selected from the group consisting of arabinonucleotides, alpha-L-locked nucleic acids, cyclohexene nucleic acids, and ribonucleotides lacking an electronegative 2'-oxygen atom. In an embodiment, the ribonucleotides lacking an electronegative 2'-oxygen atom are selected from the group consisting of 2'-alkyl-D-ribose and 2'-SCH$_3$-D-ribose.

In an embodiment, the segments each independently comprise about to about 6 arabinonucleotides or 2'-deoxynucleotides. In further embodiments, the segments each independently comprise about 2 to about 5 or about 3 to about 4 arabinonucleotides or 2'-deoxynucleotides. In a further embodiment, the segments each independently comprise about 3 arabinonucleotides or 2'-deoxynucleotides.

In an embodiment, the above-mentioned oligonucleotide has a structure selected from the group consisting of:

a) $(A_x\text{-}D_y)_n$     I b) $(D_y\text{-}A_x)_n$     II c) $(A_x\text{-}D_y)_m\text{-}A_x\text{-}D_y\text{-}A_x$     III d) $(D_y\text{-}A_x)_m\text{-}D_y\text{-}A_x\text{-}D_y$     IV wherein each of m, x and y are each independently an integer greater than or equal to 1, n is an integer greater than or equal to 2, A is an sugar-modified nucleotide and D is a 2'-deoxyribonucleotide.

In an embodiment, the above-mentioned sugar-modified nucleotide comprises a 2' substituent selected from the group consisting of fluorine, hydroxyl, amino, cyano, azido, —CH=CH$_2$, —C≡CH, alkyl, functionalized alkyl, alkoxy and functionalized alkoxy groups. In an embodiment, the alkyl group is a lower alkyl group. In an embodiment, the lower alkyl group is selected from the group consisting of methyl, ethyl and propyl groups. In an embodiment, the functionalized alkyl group is selected from the group consisting of methylamino, ethylamino and propylamino groups. In an embodiment, the alkoxy group is selected from the group consisting of methoxy, ethoxy and propoxy groups. In an embodiment, the functionalized alkoxy group is —O(CH$_2$)$_q$—R, wherein q=2, 3 or 4 and —R is selected from the group consisting of —NH$_2$, —OCH$_3$, and —OCH$_2$CH$_3$ groups.

In an embodiment, the sugar-modified nucleotide is an arabinonucleotide. In a further embodiment, the 2' substituent is fluorine and the arabinonucleotide is a 2'-fluoroarabinonucleotide (2'F-ANA; also abbreviated "FANA").

In an embodiment, the antisense oligonucleotide of the invention comprises one or more internucleotide linkages selected from the group consisting of: a) phosphodiester; b) phosphotriester; c) phosphorothioate; d) phosphorodithioate; e) Rp-phosphorothioate; f) Sp-phosphorothioate; g) boranophosphate; h) methylene (methylimino) (3'CH$_2$—N(CH$_3$)-05').; i) 3'-thioformacetal (3'S—CH$_2$-05') j) amide (3'CH$_2$—C(O)NH-5'; k) methylphosphonate; l) phosphoramidate (3'-OP(0$_2$)—N5'); and m) any combination of (a) to (1).

In an embodiment, the antisense oligonucleotide consists of about 30 or fewer nucleotides, in a further embodiment, about 8 to about 25 nucleotides, and in yet a further embodiment, about 18 nucleotides. In an embodiment, the antisense oligonucleotides has about 12 nucleotides, about 15 nucleotides, about 18 nucleotides, about 20 nucleotides, about 25 nucleotides, or about 30 nucleotides. In another embodiment, the antisense oligonucleotide is from about 12 to about 30 nucleotides long.

In an embodiment, the antisense oligonucleotide has structure I wherein x=1, y=1 and n=9, thereby having a structure: A-D-A-D-A-D-A-D-A-D-A-D-A-D-A-D-A-D. In an embodiment, the antisense oligonucleotide has structure II wherein x=1, y=1 and n=9, thereby having a structure: D-A-D-A-D-A-D-A-D-A-D-A-D-A-D-A-D-A. In an embodiment, the above-mentioned oligonucleotide has structure III wherein x=2, y=2 and m=3, thereby having a structure: A-A-D-D-A-A-D-D-A-A-D-D-A-A-D-D-A-A. In an embodiment, the above-mentioned oligonucleotide has structure IV wherein x=2, y=2 and m=3, thereby having a structure: D-D-A-A-D-D-A-A-D-D-A-A-D-D-A-A-D-D. In an embodiment, the above-mentioned oligonucleotide has structure I wherein x=3, y=3 and n=3, thereby having a structure: A-A-A-D-D-D-A-A-A-D-D-D-A-A-A-D-D-D. In an embodiment, the above-mentioned oligonucleotide has structure II wherein x=3, y=3 and n=3, thereby having a structure: D-D-D-A-A-A-D-D-D-A-A-A-D-D-D-A-A-A. In an embodiment, the above-mentioned oligonucleotide has structure III wherein x=4, y=3 and m=1, thereby having a structure: A-A-A-A-D-D-D-A-A-A-A-D-D-D-A-A-A-A. In an embodiment, the above-mentioned oligonucleotide has said structure IV wherein x=4, y=3 and m=1, thereby having a structure: D-D-D-D-A-A-A-D-D-D-D-A-A-A-D-D-D-D.

In an embodiment, the antisense oligonucleoside further comprises a third segment comprising a modified nucleoside, wherein said third segment is adjacent to (a) the 5' end of said alternating first and second segments, (b) the 3' end of said alternating first and second segments, or (c) both (a) and (b).

In an embodiment, the antisense oligonucleotide further comprises a third segment comprising a modified nucleotide, wherein said third segment is adjacent to (a) the 5' end of said alternating first and second segments, (b) the 3' end of said alternating first and second segments, or (c) both (a) and (b). In an embodiment, the modified nucleotide is a modified ribonucleotide. In an embodiment, the modified ribonucleotide comprises a modification at its 2' position. In an embodiment, the 2' modification is selected from the group consisting of methoxy, methoxyethyl, fluoro and propylamino groups.

In an embodiment, the antisense oligonucleotide is an altimer comprising alternating segments of arabinonucleotide (ANA) such as 2'F-ANA (or FANA) and DNA. "Arabinonucleotide" as used herein refers to a nucleotide comprising an arabinofuranose sugar.

Preferably, in antisense molecules, there is a sufficient degree of complementarity to the target RNA (e.g., DRR) to avoid non-specific binding of the antisense molecule to non-target sequences under conditions in which specific binding is desired, such as under physiological conditions in the case of in vivo assays or therapeutic treatment or, in the case of in vitro assays, under conditions in which the assays are conducted. The target RNA for antisense binding may include not only the information to encode a protein, but also associated ribonucleotides, which for example form the 5'-untranslated region, the 3'-untranslated region, the 5' cap region and intron/exon junction ribonucleotides.

Antisense molecules (oligonucleosides or oligonucleotides) of the invention may include those which contain intersugar backbone linkages such as phosphotriesters, methyl phosphonates, 3'-thioformacetal, amide, short chain alkyl or cycloalkyl intersugar linkages or short chain heteroatomic or heterocyclic intersugar linkages, phosphorothioates and those with $CH_2-NH-O-CH_2$, $CH_2-N(CH_3)-O-CH_2$ (known as methylene (methylimino) or MMI backbone), $CH_2-O-N(CH_3)-CH_2$, $CH_2-N(CH_3)-N(CH_3)-CH_2$ and $O-N(CH_3)-CH_2-CH_2$ backbones (where phosphodiester is $O-P(O)_2-O-CH_2$). In alternative embodiments, antisense oligonucleotides may have a peptide nucleic acid (PNA, sometimes referred to as "protein" or "peptide" nucleic acid) backbone, in which the phosphodiester backbone of the oligonucleotide may be replaced with a polyamide backbone wherein nucleosidic bases are bound directly or indirectly to aza nitrogen atoms or methylene groups in the polyamide backbone (see for example, Nielsen et al., Science, 1991, 254: 1497 and U.S. Pat. No. 5,539,082). The phosphodiester bonds may be substituted with structures that are chiral and enantiomerically specific.

As noted above, oligonucleotides may also include species which include at least one modified nucleotide base.

Thus, purines and pyrimidines other than those normally found in nature may be used. As noted above, a nucleotide of the sugar-modified nucleotide segment (e.g. ANA segment) may comprise modifications on its pentofuranosyl portion.

Examples of such modifications are 2'-O-alkyl- and 2'-halogen-substituted nucleotides. Some specific examples of modifications at the 2' position of sugar moieties which are useful in the present invention are OH, SH, $SCH_3$, F, OCN, $O(CH_2)_n$, $NH_2$ or $O(CH_2)_n CH_3$ where n is from 1 to about 10; Ci to ClO lower alkyl, substituted lower alkyl, alkaryl or aralkyl; Cl; Br; CN; $CF_3$; $OCF_3$; O-, S-, or N-alkyl; O-, S-, or N-alkenyl; $SOCH_3SO_2 CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. One or more pentofuranosyl groups of the nucleotide of the sugar-modified nucleotide segment may be replaced by another sugar, by a sugar mimic such as cyclobutyl or by another moiety which takes the place of the sugar.

"Nucleoside" refers to a base (e.g. a purine [e.g. A and G] or pyrimidine [e.g. C, 5-methyl-C, T and U]) combined with a sugar (e.g. [deoxy] ribose, arabinose and derivatives). "Nucleotide" refers to a nucleoside having a phosphate group attached to its sugar moiety. In embodiments these structures may include various modifications, e.g. either in the base, sugar and/or phosphate moieties. "Modified nucleotide/nucleoside" as used herein refers to a nucleotide/nucleoside that differs from and thus excludes the defined native form.

"Oligonucleotide" as used herein refers to a sequence comprising a plurality of nucleotides joined together. An oligonucleotide may comprise modified structures in its backbone structure and/or in one or more of its component nucleotides. In embodiments, oligonucleotides of the invention are about 1 to 200 bases in length, in further embodiments from about 5 to about 50 bases, from about 8 to about 40 bases, and yet further embodiments, from about 12 to about 25 bases in length.

As will be understood by those skilled in the art, the term "RNA" is used uniquely to refer to a nucleic acid with ribose as the sugar, whereas "oligonucleotide" is a broad term that covers RNA, DNA, modified nucleosides, modified nucleotides, FANA, and so on.

In an embodiment, the therapeutic molecule of the invention comprises an antisense oligonucleotide comprising a "gapmer". "Gapmers", which are also known as "chimeric antisense" oligos, are described for example in PCT international publication no. WO/2002/20773, the contents of which are hereby incorporated by reference.

For example, the antisense oligonucleotide may be a chimera constructed from arabinonucleotide or modified arabinonucleotide residues, flanking a series of deoxyribose nucleotide residues of variable length, that form a duplex with its target RNA sequence. Such resulting antisense oligonucleotide/RNA duplex is a substrate for RNaseH, an enzyme that recognizes this duplex and degrades the RNA target portion. RNaseH mediated cleavage of RNA targets is considered to be a major mechanism of action of antisense oligonucleotides.

In an embodiment, the therapeutic oligonucleotide is an antisense hybrid chimera, constructed from 2'-deoxy-2'-fluoro-β-D-arabinonucleotides (FANA) flanking a defined sequence constructed from β-D-2'-deoxyribonucleotides (DNA). In one embodiment the oligonucleotide comprises a chimera of modified arabinose and 2'-deoxy sugars. Such an oligonucleotide has a general backbone composition of "[FANA WING]-[DNA GAP]-[FANA W1NG]", or 5'RO(FANA-p)x-(DNA-p)y-(FANA-p)z-(FANA)3'OH, and more precisely has the general structure:

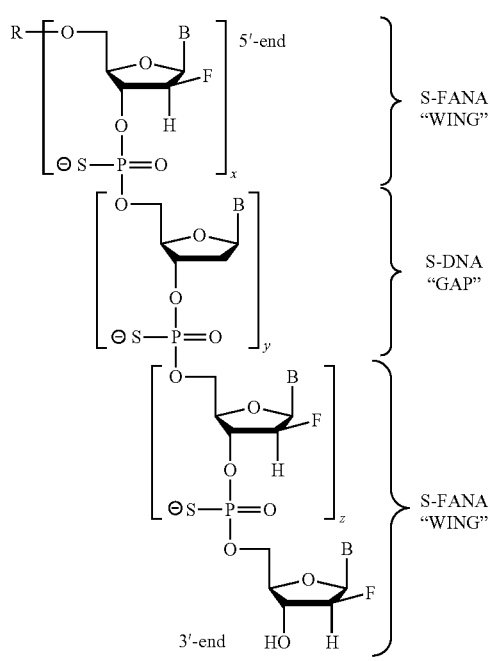

wherein, x≥1, y≥1, and z≥0, and R is selected from the group consisting of hydrogen, thiophosphate, and a linker moiety that enhances cellular uptake of such oligonucleotide.

In another embodiment of the present invention, the antisense oligonucleotide has the formula:

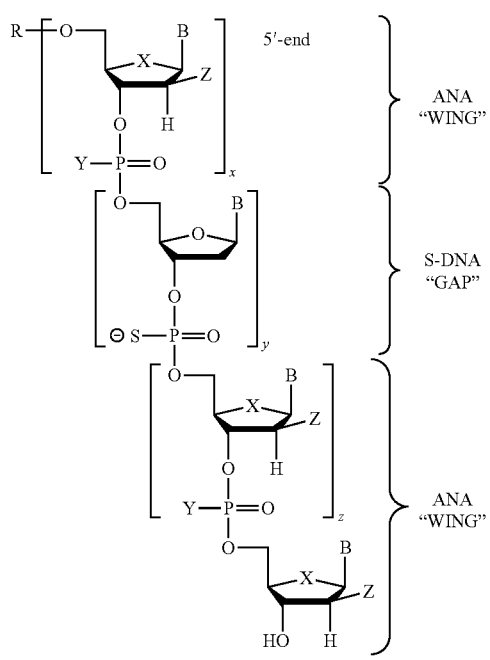

wherein x≥1, y≥1, and z≥0; R is selected from the group consisting of hydrogen, thiophosphate, and a linker moiety that enhances cellular uptake of such oligonucleotide; B is selected from the group consisting of adenine, guanine, uracil, thymine, cytosine, inosine, and 5-methylcytosine; Y at the internucleotide phosphate linkage is selected from the group consisting of sulfur, oxygen, methyl, amino, alkylamino, dialkylamino (the alkyl group having one to about 20 carbon atoms), methoxy, and ethoxy; X at the furanose ring (position 4') is selected from the groups oxygen, sulfur, and methylene ($CH_2$); and Z at the 2' position of the sugar ring is selected from the group consisting of a halogen (fluorine, chlorine, bromine, iodine), alkyl, alkylhalide (e.g., —$CH_2F$), allyl, amino, aryl, alkoxy, and azido.

In another embodiment of the present invention, the antisense oligonucleotide has the formula:

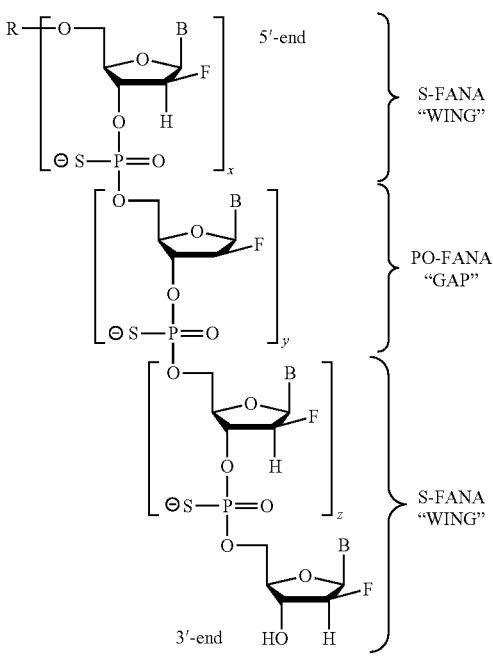

wherein x≥1, y≥1, and z≥0; R is selected from the group consisting of hydrogen, thiophosphate, and a linker moiety that enhances cellular uptake of such oligonucleotide; B is selected from the group consisting of adenine, guanine, uracil, thymine, cytosine, inosine, and 5-methylcytosine.

In accordance with another embodiment of the present invention there is provided an antisense oligonucleotide targeting DRR which has the formula:

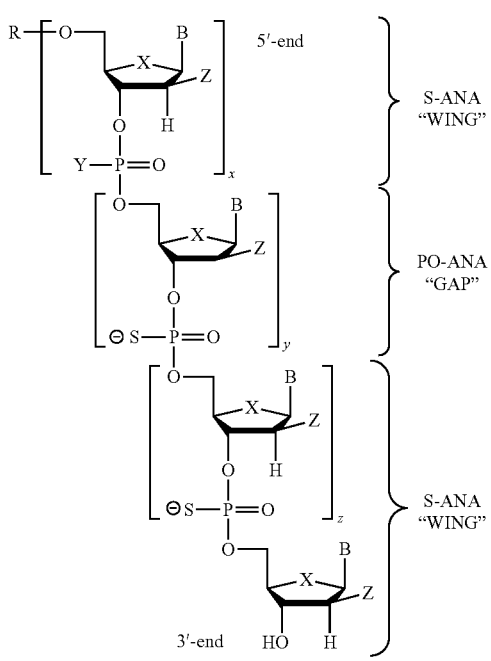

wherein x≥1, y≥1, and z≥0; R is selected from the group consisting of hydrogen, thiophosphate, and a linker moiety that enhances cellular uptake of such oligonucleotide; B is selected from the group consisting of adenine, guanine, uracil, thymine, cytosine, inosine, and 5-methylcytosine; Y at the internucleotide phosphate linkage is selected from the group consisting of sulfur, oxygen, methyl, amino, alkylamino, dialkylamino (the alkyl group having one to about 20 carbon atoms), methoxy, and ethoxy; X at the furanose ring (position 4') is selected from the groups oxygen, sulfur, and methylene ($CH_2$); and Z at the 2' position of the sugar ring is selected from the group consisting of a halogen (fluorine, chlorine, bromine, iodine), hydroxyl, alkyl, alkylhalide (e.g., —$CH_2F$), allyl, amino, aryl, alkoxy, and azido. In a particular embodiment, R is a thiophosphate and the antisense oligonucleotide is a phosphorothioate.

In other embodiments, antisense oligonucleotides entirely made up of FANA units, as described in WO/1999/67378 are used in the compositions and methods of the invention. For example, the antisense oligonucleotide may comprise sugar-modified oligomers composed of P-D-arabinonucleotides (i.e., ANA oligomers) and 2'-deoxy-2'-fluoro-β-D-arabinonucleosides (i.e., 2'F-ANA oligomers), such as those described in International PCT publication no. WO/1999/67378.

In still other embodiments, the oligonucleotide of the invention may be a nucleic acid ligand (or "aptamer") capable of forming a G-tetrad or a unique 3-dimensional structure that binds DRR, and comprising at least one arabinose modified nucleotide. For example, the arabinose modified nucleotide may be 2'-deoxy-2'-fluoroarabinonucleotide (FANA). The arabinose modified nucleotide may be in the loop of the G-Tetrad or alternatively a guanosine residue of the G-tetrad.

In an embodiment, the aptamer is fully substituted with arabinonucleotides. For example: 5'-AAAAAAAAAAAAAAA-3'. In another embodiment, the antisense RNA is a chimera constructed from 2'-deoxyribonucleotide (DNA) and 2'-deoxy-2'-fluoroarabinonucleotide (FANA). In another embodiments of the invention, the antisense RNA of the invention is an aptamer having a sugar-phosphate backbone composition selected from any combination of arabinose and deoxyribose nucleotides. In a particular embodiment, the arabinose nucleotides are 2'-deoxy-2'-fluoroarabinonucleotide (FANA). In other embodiments of the invention, the arabinonucleotide comprises a 2' substituent selected from the group consisting of fluorine, hydroxyl, amino, azido, alkyl, alkoxy, and alkoxyalkyl groups. In a further embodiment of the invention, the alkyl group is selected from the group consisting of methyl, ethyl, propyl, butyl, and functionalized alkyl groups such as ethylamino, propylamino and butylamino groups. In embodiments, the alkoxy group is selected from the group consisting of methoxy, ethoxy, proproxy and functionalized alkoxy groups such as —$O(CH_2)_q$—R, where q=2-4 and —R is a —$NH_2$, —$OCH_3$, or —$OCH_2CH_3$ group. In embodiments, the alkoxyalkyl group is selected from the group consisting of methoxyethyl, and ethoxyethyl. In embodiments, the 2' substituent is fluorine and the arabinonucleotide is a 2'-fluoroarabinonucleotide (FANA). In one embodiment, the FANA nucleotide can be araF-N (wherein N=U, T, C, G or A).

In other embodiments of the invention, the oligonucleotide of the invention is an aptamer comprising one or more internucleotide linkages selected from the group consisting of: a) phosphodiester; b) phosphotriester; c) phosphorothioate; d) methylphosphonate; e) boranophosphate; and f) any combination of (a) to (e).

In yet other embodiments, oligonucleotides such as those described in PCT international publication no. WO/2007/038869 are used in the compositions and methods of the invention. Such oligonucleotides may be nucleic acid ligands (or aptamers) capable of forming a G-tetrad or other unique three dimensional structures that bind DRR, and comprising at least one arabinose modified nucleotide. In an embodiment, the arabinose modified nucleotide is 2'-deoxy-2'-fluoroarabinonucleotide (FANA).

In an embodiment, the aptamer may have any number of arabinonucleotides at any location in the aptamer, for example:

```
5'-ADADADADADADADA-3';  5'-AADADDADDDAADAD-3';

5'-AAAADAAADADDDAD-3'; etc,
``` wherein A is an arabinonucleotide and D is a 2'-deoxyribonucleotide.

In other embodiments of the invention, the aptamer is fully substituted with arabinonucleotides. For example: 5'-AAAAAAAAAAAAAAA-3'.

In other embodiments of the present invention, chimeras constructed from 2'-deoxyribonucleotide (DNA) and 2'-deoxy-2'-fluoroarabinonucleotide (FANA) capable of binding DRR selectively are provided.

In other embodiments, the oligonucleotide of the invention is an aptamer of any one of sequence having a sugar-phosphate backbone composition selected from any combination of arabinose and deoxyribose nucleotides. The arabinose nucleotides may be 2'-deoxy-2'-fluoroarabinonucleotide (FANA).

In other embodiments of the invention, the arabinonucleotide comprises a 2' substituent selected from the group consisting of fluorine, hydroxyl, amino, azido, alkyl, alkoxy, and alkoxyalkyl groups. In a further embodiment of the invention, the alkyl group is selected from the group consisting of methyl, ethyl, propyl, butyl, and functionalized alkyl groups such as ethylamino, propylamino and butylamino groups. In embodiments, the alkoxy group is selected from the group consisting of methoxy, ethoxy, proproxy and functionalized alkoxy groups such as —O(CH$_2$)$_q$—R, where q=2-4 and —R is a —NH$_2$, —OCH$_3$, or —OCH$_2$CH$_3$ group. In embodiments, the alkoxyalkyl group is selected from the group consisting of methoxyethyl, and ethoxyethyl. In embodiments, the 2' substituent is fluorine and the arabinonucleotide is a 2'-fluoroarabinonucleotide (FANA). In an embodiment, the FANA nucleotide is araF-G, araF-T, araF-C, araF-A or araF-U.

In other embodiments of the invention, the aptamer comprising one or more internucleotide linkages selected from the group consisting of: a) phosphodiester; b) phosphotriester; c) phosphorothioate; d) methylphosphonate; e) boranophosphate; and f) any combination of (a) to (e).

In another embodiment, the aptamer with at least one nucleotide of the aptamer, preferably in a loop of the aptamer that forms a G-tetrad, or a unique 3-dimensional structure that binds DRR, replaced with an arabinose modified nucleotide, preferably 2'-deoxy-2'-fluoroarabinonucleotide (FANA).

In other embodiments, antisense oligonucleotides such as those described in WO/2003/037909 may be used in the methods and compositions of the invention. In brief, such oligonucleotides have the structure: [R'—XJ$_a$-R$^2$]a
wherein a is greater than or equal to 1; wherein each of R$^1$ and R$^2$ are independently at least one nucleotide; and wherein X is an acyclic linker. In an embodiment, the oligonucleotide comprises at least one modified deoxyribonucleotide, i.e. either R$^1$, R$^2$ or both may comprise at least one modified deoxyribonucleotide. In an embodiment, the modified deoxyribonucleotide is selected from the group consisting of ANA, PS-ANA, PS-DNA, RNA-DNA and DNA-RNA chimeras, PS-[RNA-DNA] and PS-[DNA-RNA] chimeras, PS-[ANA-DNA] and PS-[DNA-ANA] chimeras, RNA, PS-RNA, PDE- or PS-RNA analogues, locked nucleic acids (LNA), phosphorodiamidate morpholino nucleic acids, N3'-P5' phosphoramidate DNA, cyclohexene nucleic acid, alpha-L-LNA, boranophosphate DNA, methylphosphonate DNA, and combinations thereof. In an embodiment, the ANA is FANA (e.g. PDE- or PS-FANA).

In an embodiment, the above-mentioned PDE- or PS-RNA analogues are selected from the group consisting of 2'-modified RNA wherein the 2'-substituent is selected from the group consisting of alkyl, alkoxy, alkylalkoxy, F and combinations thereof. In an embodiment, the acyclic linker is selected from the group consisting of an acyclic nucleoside and a non-nucleotidic linker. In embodiments, the acyclic nucleoside is selected from the group consisting of purine and pyrimidine seconucleosides. In embodiments, the purine seconucleoside is selected from the group consisting of secoadenosine and secoguanosine. In embodiments, the pyrimidine seconucleoside is selected from the group consisting of secothymidine, secocytidine and secouridine. In an embodiment, the non-nucleotidic linker comprises a linker selected from the group consisting of an amino acid and an amino acid derivative. In embodiments, the amino acid derivative is selected from the group consisting of (a) an N-(2-aminoethyl) glycine unit in which an heterocyclic base is attached via a methylene carbonyl linker (PNA monomer); and (b) an O-PNA unit.

According to a further aspect of the invention, there is provided an antisense oligonucleotide chimera of general structure Ib:

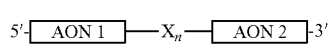

Ib wherein n is greater than or equal to 1. With reference to structure Ib above, "AON1" is an oligonucleotide chain, which in embodiments is selected from the group consisting of ANA (e.g. FANA), DNA, PS-DNA, 5'-RNA-DNA-3' chimeras, as well as other RNase H-competent oligonucleotides, for example arabinonucleic acids (2'-OH substituted ANA) (Damha, M. J. et al. J. Am. Chem. Soc. 1998, 120, 12976), cyclohexene nucleic acids (Wang J. et al. J. Am. Chem. Soc. 2000, 122, 8595), boranophosphate linked DNA (Rait, V. K. et al. Antisense Nucleic Acid Drug Dev. 1999, 9, 53), and alpha-L-locked nucleic acids (Sørensen, M. D. et al. J. Am. Chem. Soc. 2002, 124, 2164) or combinations thereof; and "AON2" is an oligonucleotide chain, which in embodiments is selected from the group consisting of FANA, DNA, PS-DNA, 5'-DNA-RNA-3' chimeras, as well as other RNase H-competent oligonucleotides such as those described above, or combinations thereof. The internucleotide linkages of the AON1 and AON2 include but are not necessarily limited to phosphodiester, phosphotriester, phosphorothioate, methylphosphonate, and/or phosphoramidate (5'N-3'P and 5'P-3'N) groups. The substituent directly attached to the C2'-atom of the arabinose sugar in ANA-X-ANA chimera constructs includes but is not limited to fluorine, hydroxyl, amino, azido, alkyl (e.g. 2'-methyl, ethyl, propyl, butyl, etc.), and alkoxy groups (e.g., 2'-OMe, 2'-OEt, 2'-OPr, 2'-OBu, 2'-OCH$_2$CH$_2$OMe, etc.).

In other embodiments, an antisense oligonucleotide of the invention has the structure:

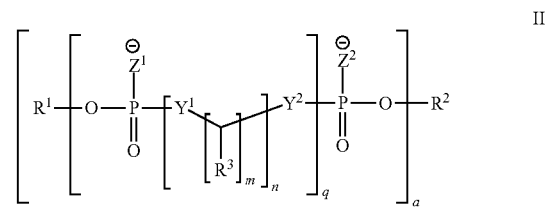

II wherein each of m, n, q and a are independently integers greater than or equal to 1; wherein each of R and R$^2$ are independently at least one nucleotide, wherein each of Z$^1$ and Z$^2$ are independently selected from the group consisting of an oxygen atom, a sulfur atom, an amino group and an alkylamino group; wherein each of Y$^1$ and Y$^2$ are independently selected from the group consisting of oxygen, sulfur and NH; and wherein R$^3$ is selected from the group consisting of H, alkyl, hydroxyalkyl, alkoxy, a purine, a pyrimidine and combinations thereof. In embodiments, R$^3$ is adenine or guanine, or derivatives thereof. In embodiments, R$^3$ is thymine, cytosine, 5-methylcytosine, uracil, or derivatives thereof. In embodiments, each of R$^1$ and R$^2$ noted above are independently selected from the group consisting of ANA, PS-ANA, PS-DNA, RNA-DNA and DNA-RNA chimeras, PS-[RNA-DNA] and PS-[DNA-RNA] chimeras, PS-[ANA-DNA] and PS-[DNA-ANA] chimeras, alpha-L-LNA, cyclohexene nucleic acids, RNA, PS-RNA, PDE- or PS-RNA analogues, locked nucleic acids (LNA), phosphorodiamidate morpholino nucleic acids, N3'-P5' phosphoramidate DNA, methylphosphonate DNA, and combinations thereof.

In embodiments, each of R$^1$ and R$^2$ noted above independently may comprise at least two nucleotides connected via an internucleotide linkage, wherein said internucleotide linkage is selected from the group consisting of phosphodiester, phosphotriester, phosphorothioate, methylphosphonate, phosphoramidate (5'N-3'P and 5'P-3'N) groups and combinations thereof. In other embodiments, each of $R^1$ and $R^2$ noted above independently comprise ANA. In embodiments the above-noted ANA comprises a 2'-substituent selected from the group consisting of fluorine, hydroxyl, amino, azido, alkyl (e.g. methyl, ethyl, propyl and butyl) and alkoxy (e.g. methoxy, ethoxy, propoxy, and methoxyethoxy) groups. In an embodiment, the 2'-substituent is fluorine and said ANA is FANA. In embodiments, the alkyl group is selected from the group consisting of methyl, ethyl, propyl and butyl groups. In embodiments, the alkoxy group is selected from the group consisting of methoxy, ethoxy, propoxy, and methoxyethoxy groups.

In other embodiments, an antisense oligonucleotide of the invention targeting DRR is selected from the group consisting of:

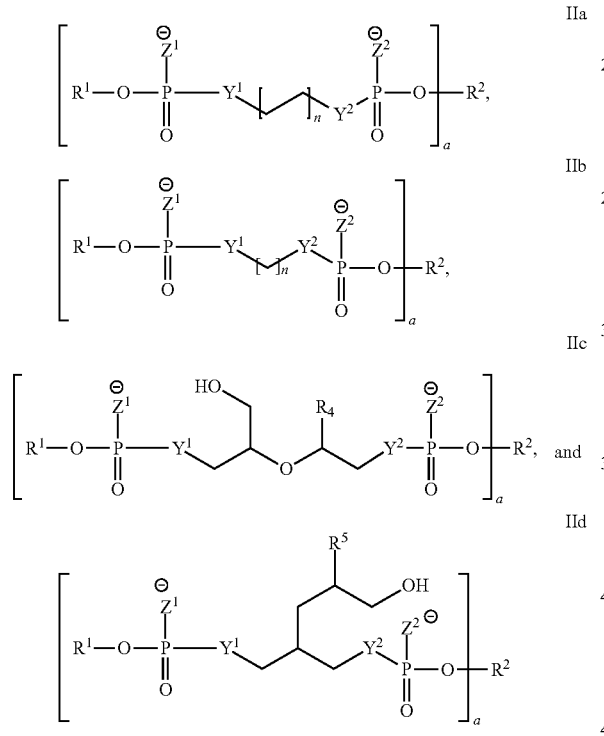

wherein $R^1$, $R^2$, n, a, $Z^1$, $Z^2$, $Y^1$ and $Y^2$ are as defined above and each of $R^4$ and $R^5$ are independently selected from the group consisting of a purine (e.g. adenine and guanine or derivatives thereof) and a pyrimidine (e.g. thymine, cytosine, uracil, or derivatives thereof). In an embodiment, $R^1$ and $R^2$ are PDE-FANA; and a=1. In an embodiment, $R^1$ and $R^2$ are PS-FANA; and a=1. In an embodiment, $R^1$ is [FANA-DNA]; $R^2$ is [DNA-FANA]; and a=1. In an embodiment, $R^1$ is [FANA-DNA]; $R^2$ is FANA; and a=1. In an embodiment, $R^1$ is FANA; $R^2$ is [DNA-FANA]; and a=1. In an embodiment, $R^1$ and $R^2$ are PS-DNA; and a=1. In an embodiment, $R^1$ is PDE-[RNA-DNA], $R^2$ is PDE-[DNA-RNA]; and a=1. In an embodiment, $R^1$ is RNA; $R^2$ is [DNA-RNA]; and a=1. In an embodiment, $R^1$ is S-[(2'O-alkyl) RNA-DNA]; $R^2$ is S-[DNA-(2O-alkyl)RNA]; and a=1. In an embodiment, $R^1$ is S-[(2'O-alkyl) RNA-DNA]; $R^2$ is S-[(2'O-alkyl) RNA]; and a=1. In an embodiment, $R^1$ is S-[(2'O-alkyl) RNA]; $R^2$ is S-[DNA-(2'O-alkyl) RNA]; and a=1. In an embodiment, $R^1$ is S-[(2' O-alkoxyalkyl) RNA-DNA]; $R^2$ is S-[DNA-(2' O-alkoxyalkyl) RNA]; and a=1. In an embodiment, $R^1$ is S-[(2'O-alkoxyalkyl) RNA-DNA]; $R^2$ is S-[(2'O-alkoxy-alkyl) RNA]; and a=1. In an embodiment, $R^1$ is S-[(2' O-alkoxyalkyl) RNA]; $R^2$ is S-[DNA-(2' O-alkoxyalkyl) RNA]; and a=1. In an embodiment, $R^1$ is PDE-[(2' O-alkyl-RNA)-DNA]; $R^2$ is PDE-[DNA-(2'O-alkyl RNA)]; and a=1. In an embodiment, $R^1$ is PS-[(2' O-alkyl-RNA)-DNA]; $R^2$ is PS-[DNA-(2'O-alkyl RNA)]; and a=1. In an embodiment, $R^1$ is PDE-[(2' O-alkoxyalkyl-RNA)-DNA]; $R^2$ is PDE-[DNA-(2' O-alkoxyalkyl RNA)]; and a=1.

In an embodiment, $R^1$ is PS-[(2' O-alkoxyalkyl-RNA)-DNA]; $R^2$ is PS-[DNA-(2' O-alkoxyalkyl RNA)]; and a=1. In an embodiment, $R^1$ and $R^2$ are PDE-[FANA]; a=1; and the oligonucleotide has structure IIb in which $Y^1$, $Y^2$ are oxygen; $Z^1$, $Z^2$ are both oxygen or sulfur, and n=4. In an embodiment, $R^1$ is PS-[FANA]; $R^2$ is PDE-[FANA]; a=1; and the oligonucleotide has structure IIb in which $Y^1$, $Y^2$ are oxygen; $Z^1$, $Z^2$ are both oxygen or sulfur, and n=4. In an embodiment, $R^1$ is FANA; $R^2$ is PS-FANA; a=1; and the oligonucleotide has structure IIb in which $Y^1$, $Y^2$, $Z^1$ and $Z^2$ are oxygen and n=4. In an embodiment, $R^1$ and $R^2$ are PS-[FANA]; a=1; and the oligonucleotide has structure IIb in which $Y^1$, $Y^2$ are oxygen; $Z^1$, $Z^2$ are both oxygen or sulfur, and n=4. In an embodiment, $R^1$ is PS-[DNA]; $R^2$ is PDE-[DNA]; a=1; and the oligonucleotide has structure IIb in which $Y^1$, $Y^2$ are oxygen; $Z^1$, $Z^2$ are both oxygen or sulfur, and n=4. In an embodiment, $R^1$ is PDE-[DNA]; $R^2$ is PS-[DNA]; a=1; and the oligonucleotide has structure IIb in which $Y^1$, $Y^2$ are oxygen; $Z^1$, $Z^2$ are both oxygen or sulfur, and n=. In an embodiment, $R^1$ and $R^2$ are PS-[DNA]; a=1; and the oligonucleotide has structure IIb in which $Y^1$, $Y^2$ are oxygen; $Z^1$, $Z^2$ are both oxygen or sulfur, and n=4. In an embodiment, $R^1$ and $R^2$ are PDE-[FANA]; a=1; and the oligonucleotide has structure IIc in which $Y^1$, $Y^2$ are oxygen; $Z^1$, $Z^2$ are both oxygen or sulfur. In an embodiment, $R^1$ is PS-[FANA]; $R^2$ is PDE-[FANA]; a=1; and the oligonucleotide has structure IIc in which $Y^1$, $Y^2$ are oxygen; $Z^1$, $Z^2$ are both oxygen or sulfur. In an embodiment, $R^1$ is PDE-[FANA]; $R^2$ is PS-[FANA]; a=1; and the oligonucleotide has structure IIb in which $Y^1$, $Y^2$ are oxygen; $Z^1$, $Z^2$ are both oxygen or sulfur, and n=4. In an embodiment, $R^1$ and $R^2$ are PS-[FANA]; a=1; and the oligonucleotide has structure IIc in which $Y^1$, $Y^2$ are oxygen; $Z^1$, $Z^2$ are both oxygen or sulfur. In an embodiment, $R^1$ is PS-[DNA]; $R^2$ is PDE-[DNA]; a=1; and the oligonucleotide has structure IIc in which $Y^1$, $Y^2$ are oxygen; $Z^1$, $Z^2$ are both oxygen or sulfur. In an embodiment, $R^1$ is DNA; $R^2$ is PS-DNA; a=1; and the oligonucleotide has structure IIe. In an embodiment, $R^1$ and $R^2$ are PS-[DNA]; a=1; and the oligonucleotide has structure IIc in which $Y^1$, $Y^2$ are oxygen; $Z^1$, $Z^2$ are both oxygen or sulfur. In an embodiment, a=2 and each of $R^1$ and $R^2$ independently consist of at least 3 nucleotides, in a further embodiment, of 3-8 nucleotides. In an embodiment, a=3 and each of $R^1$ and $R^2$ independently consist of at least 2 nucleotides, in a further embodiment, wherein each of $R^1$ and $R^2$ independently consist of 2-6 nucleotides. In an embodiment, the oligonucleotide is antisense to a target RNA.

In the present context, the term "therapeutic molecule" refers to nucleic acid molecules for use in reducing or inhibiting DRR expression. A therapeutic molecule may be, for example, a therapeutic oligonucleotide or a therapeutic RNA. Non-limiting examples of therapeutic molecules include antisense RNAs, antisense oligonucleotides, aptamers, ribozymes and other like nucleic acid molecules, as are known in the art to reduce expression of a target RNA. In an embodiment, the target RNA is the DRR mRNA or a fragment or portion thereof. Therapeutic molecules are also referred to herein as "therapeutic nucleic acid molecules" and the terms are used interchangeably. In some embodiments, the therapeutic molecule or oligonucleotide encompasses oligonucleotides which specifically hybridize with one or more nucleic acid molecules encoding DRR or a portion or fragment thereof. In other embodiments, oligonucleotides comprising the sequence of SEQ ID NO: 1, 2, 5, 6, 7, 8, 9, 10, 14, 15 or 16, or a fragment or derivative thereof, are encompassed.

In an embodiment, the therapeutic molecule, e.g. therapeutic RNA or therapeutic oligonucleotide, of the invention is an oligonucleotide which is complementary to or specifically hybridizes with a fragment or portion of the DRR mRNA. Non-limiting examples of the fragment or portion of the DRR mRNA to which the therapeutic molecule is complementary or specifically hybridizes include the following: nucleotides 170-190 of the DRR mRNA; nucleotides 175-195 of the DRR mRNA; nucleotides 180-200 of the DRR mRNA; nucleotides 185-205 of the DRR mRNA; nucleotides 190-210 of the DRR mRNA; nucleotides 195-215 of the DRR mRNA; nucleotides 200-220 of the DRR mRNA; nucleotides 205-225 of the DRR mRNA; nucleotides 210-230 of the DRR mRNA; nucleotides 215-235 of the DRR mRNA; nucleotides 220-240 of the DRR mRNA; nucleotides 225-245 of the DRR mRNA; nucleotides 230-250 of the DRR mRNA; nucleotides 235-255 of the DRR mRNA; nucleotides 240-260 of the DRR mRNA; nucleotides 245-265 of the DRR mRNA; nucleotides 250-270 of the DRR mRNA; nucleotides 255-275 of the DRR mRNA; nucleotides 260-280 of the DRR mRNA; nucleotides 265-285 of the DRR mRNA; nucleotides 270-290 of the DRR mRNA; nucleotides 275-295 of the DRR mRNA; nucleotides 280-300 of the DRR mRNA; nucleotides 285-305 of the DRR mRNA; nucleotides 290-310 of the DRR mRNA; nucleotides 295-315 of the DRR mRNA; nucleotides 300-320 of the DRR mRNA; nucleotides 305-325 of the DRR mRNA; nucleotides 310-330 of the DRR mRNA; nucleotides 315-335 of the DRR mRNA; nucleotides 320-340 of the DRR mRNA; nucleotides 325-345 of the DRR mRNA; nucleotides 330-350 of the DRR mRNA; nucleotides 335-355 of the DRR mRNA; nucleotides 340-360 of the DRR mRNA; nucleotides 345-365 of the DRR mRNA; nucleotides 350-370 of the DRR mRNA; nucleotides 355-375 of the DRR mRNA; nucleotides 360-380 of the DRR mRNA; nucleotides 365-385 of the DRR mRNA; nucleotides 370-390 of the DRR mRNA; nucleotides 375-395 of the DRR mRNA; nucleotides 380-400 of the DRR mRNA; or a fragment, portion or derivative thereof.

In other embodiments, the therapeutic nucleic acid molecule has a sequence complementary to or specifically hybridizing to nucleotides 425 to 439 of the DRR mRNA, or complementary to or specifically hybridizing to nucleotides 420 to 444 of the DRR mRNA, or complementary to or specifically hybridizing to nucleotides 415 to 439 of the DRR mRNA, or complementary to or specifically hybridizing to nucleotides 424 to 439 of the DRR mRNA, 423 to 439, 422 to 439, 421 to 439, or 420 to 439, or 420 to 434 of the DRR mRNA; or a fragment, portion or derivative thereof.

It shall be understood that nucleic acids hybridizing to an additional 1 to 3 nucleotides at either end or to a smaller fragment or to a derivative of the recited sequences and regions are also encompassed. In addition, nucleic acid sequences may include extra nucleotides required for function of the therapeutic molecule.

In yet other embodiments, the therapeutic molecule of the invention is an antisense oligonucleotide which has the structure of an altimer, a gapmer, and/or comprises one or more modified nucleotide such as 2'-deoxy-2'-fluoroarabinonucleotide (FANA), or is an aptamer, as described herein.

Nucleic Acid Molecules and Expression Constructs

The invention is in one aspect related to the use of a nucleic acid sequence (e.g. a therapeutic nucleic acid molecule, e.g., an antisense oligonucleotide, a DNA encoding same, or a vector producing same) to prepare an antisense molecule suitable for reducing the expression of a target gene, e.g. DRR, in tumor cells, e.g. glioma cells.

As used herein the term "reducing the expression of a target gene" refers to the ability of the present therapeutic molecule or therapeutic oligonucleotide, e.g. antisense, or other therapeutic molecules (e.g., aptamer), to block expression of the target gene in a specific and post-transcriptional manner.

In one embodiment the invention relates to the use of an RNA sequence or oligonucleotide sequence to prepare a therapeutic molecule as defined herein. In an embodiment, the therapeutic molecule is characterized by one or more, and in one embodiment by all, of the following criteria: having at least 50% sequence identity, or at least 70% sequence identity, or at least 80% sequence identity, or at least 90% sequence identity with the target mRNA; having a sequence which targets the exon area of the target gene; and/or showing a preference for targeting the 3' end of the target gene rather than for targeting the 5' end of the target gene. In some embodiments, the target gene is DRR or a fragment of the gene encoding DRR.

In a further embodiment, the therapeutic molecule may be further characterized by one or more, or by all, of the following criteria: having a nucleic acid length of between 15 to 25 nucleotides, or of between 18 to 22 nucleotides, or of 19 nucleotides, or of between 19 to 33 nucleotides, 21 to 31 nucleotides, or of 29 nucleotides; or of 13 to 17 nucleotides, having a GC content comprised between 30 and 50%; showing a TT(T) sequence at its 3' end; showing no secondary structure when adopting the duplex form; having a Tm (melting temperature) of lower than 20° C.; or having the nucleotides indicated in SEQ ID NOs: 1, 2, 5-10 or 14-16 (the nucleotide sequences are given in Table 1; "nt" stands for nucleotide). In an embodiment, the therapeutic molecule has a nucleic acid length of 15 nucleotides.

In another embodiment, the therapeutic molecule or oligonucleotide comprises 15 nucleotides complementary to the DRR mRNA with additional nucleotides necessary to improve function as a therapeutic nucleic acid. In yet another embodiment, the therapeutic nucleic acid molecule has the sequence of SEQ ID NO: 1 or 2. In another embodiment, the therapeutic nucleic acid molecule has a sequence complementary to or specifically hybrizing to nucleotides 425 to 439 of the DRR mRNA, or complementary to or specifically hybrizing to nucleotides 420 to 444 of the DRR mRNA or a fragment or derivative thereof, or complementary to or specifically hybrizing to nucleotides 415 to 439 of the DRR mRNA or a fragment or derivative thereof, or complementary to or specifically hybrizing to nucleotides 424 to 439 of the DRR mRNA, 423 to 439, 422 to 439, 421 to 439, or 420 to 439, or 420 to 434 of the DRR mRNA. It shall be understood that nucleic acids hybridizing to an additional 1 to 3 nucleotides at either end or to a smaller fragment or derivative of the recited sequences are also encompassed. In addition, nucleic acid sequences may include extra nucleotides required for function of the therapeutic molecule.

In an embodiment, the therapeutic molecule or oligonucleotide of the invention comprises the sequences provided herein, for example SEQ ID NOs: 1, 2, 5-10 or 14-16. In another embodiment, the therapeutic molecule or oligonucleotide of the invention consists of the sequences provided herein, for example SEQ ID NOs: 1, 2, 5-10 or 14-16.

In another embodiment, the therapeutic molecule or oligonucleotide of the invention has the sequence of SEQ ID NO: 14, 15 or 16.

TABLE 1

Exemplary nucleic acid sequences

| Sequence (5' -> 3') | SEQ ID NO: | Brief description |
|---|---|---|
| 5' GCTCTCTCTCTTCGCCGGCCAATGCGGCA | 1 | RNAi primer sequence (29 nt) |
| 5' GCTCTCTCTCTTCGC | 2 | Antisense nt sequence |
| 5' GCGAAGAGAGAGAGC | 3 | Sense sequence complementary to SEQ ID NO: 2 (nts 425-439 of DRR mRNA) |
| 5' atgtactcgg agatccagag ggagcgggca gacattgggg gcctgatggc ccggccagaa tacagagagt ggaatccgga gctcatcaag cccaagaagc tgctgaaccc cgtgaaggcc tctcggagtc accaggagct ccaccgggag ctgctcatga accacagaag gggccttggt gtggacagca agccagagct gcagcgtgtc ctagagcacc gccggcggaa ccagctcatc aagaagaaga aggaggagct ggaagccaag cggctgcagt gccccttga gcaggagctg ctgagacggc agcagaggct gaaccagctg gaaaaaccac cagagaagga agaggatcac gcccccgagt ttattaaagt cagggaaaac ctgcggagaa ttgccacact gaccagcgaa gagagagagc tttaa | 4 | DRR mRNA sequence |
| 5' GCTCTCTCTCTTCGCT | 5 | Antisense nt sequence |
| 5' GCTCTCTCTCTTCGCTG | 6 | Antisense nt sequence |
| 5' GCTCTCTCTCTTCGCTGG | 7 | Antisense nt sequence |
| 5' GCTCTCTCTCTTCGCTGGT | 8 | Antisense nt sequence |
| 5' GCTCTCTCTCTTCGCTGGTC | 9 | Antisense nt sequence |
| 5' CTCTCTTCGCTGGTC | 10 | Antisense nt sequence |
| 5' T-T-C-C-T-T-G-G-T-C-G-A-G-T-A-G-T-T-C-T-T | 11[a] | Antisense nt sequence |
| 5' T-T-C-C-T-T-G-G-T-C-G-A-G-T-A-G-T-T-C-T-T | 12[a] | Antisense nt sequence |
| 5' A-T-A-T-C-C-T-T-G-T-C-G-T-A-T-C-C-C | 13[a] | Antisense nt sequence |
| 5' A-A-T-G-T-C-T-G-C-C-C-G-C-T-C-C-C-T-C-T 3' | 14[a] | Antisense nt sequence |
| 5' A-A-T-G-T-C-T-G-C-C-C-G-C-T-C-C-C-T-C-T 3' | 15[a] | Antisense nt sequence |
| 5' A-A-T-G-T-C-T-G-C-C-C-G-C-T-C-C-C-T-C-T 3' | 16[a] | Antisense nt sequence |

[a]Nucleotides shown in bold and underlined are FANA nucleotides; other nucleotides are DNA; "-" indicates phosphorothioate (PS) linkages.

In another embodiment, the invention is related to the use of a nucleic acid sequence containing any of the following sequences: SEQ ID NO: 1, 2, 5, 6, 7, 8, 9, 10, 14, 15 or 16, or a fragment or derivative thereof, to prepare a therapeutic molecule, for example an antisense oligonucleotide, suitable for reducing the expression of DRR in glioma cells.

In the context of the present invention, the terms "fragment" and "derivative" refer to nucleic acids that may differ from the original nucleic acid in that they are extended or shortened on either the 5' or the 3' end, on both ends or internally, or extended on one end, and shortened on the other end, provided that the function of the resulting molecule, namely the down-regulation of the target gene, is not abolished or inhibited. The terms "fragment" and "derivative" also refer to nucleic acids that may differ from the original nucleic acid in that one or more nucleotides of the original sequence are substituted by other nucleotides and/or (chemically) modified by methods available to the skilled person, provided that the function of the resulting molecule is not abolished or inhibited. The "fragment" and "derivative" may typically show at least 80%, e.g., at least 85%, at least 90%, at least 95% or even at least 99% sequence identity to the original nucleic acid. Sequence identity between two nucleotide sequences can be calculated by aligning the said sequences and determining the number of positions in the alignment at which the two sequences contain the same nucleic acid base vs. the total number of positions in the alignment.

It should be understood that fragments and derivatives of the nucleic acid sequences in Table 1 which retain the ability to reduce or decrease DRR expression are encompassed. For example, nucleic acid sequences comprising about 12, about 13, about 14, about 15, about 16, about 17, about 18 or about 19 contiguous nucleotides from the sequences given in Table 1, and retaining the ability to reduce/decrease DRR expression, are encompassed.

It shall be clear to a person of skill in the art that any of the above-given sequences or complementary sequences thereof may be used to prepare a therapeutic molecule, e.g. an antisense oligonucleotide, for example a double stranded RNA molecule. The person of skill in the art knows how to prepare an antisense oligonucleotide when the above disclosed nucleic acids, particularly RNAs, are provided. Briefly, the required nucleic acids may be synthesized by any available method and strands annealed, as required, under appropriate conditions. The annealing conditions, e.g. temperatures and incubation periods, may be adjusted according to the respective nucleic acid sequences.

In a particular embodiment the invention relates to the use of a nucleic acid sequence containing the sequence of SEQ ID NO: 1, 2, 5, 6, 7, 8, 9, 10, 14, 15 or 16, a fragment or derivative thereof, to prepare a therapeutic molecule, such as an antisense oligonucleotide.

In another embodiment, the invention relates to the use of an RNA sequence containing the sequence of SEQ ID NO: 1, 2, 5, 6, 7, 8, 9, 10, 14, 15 or 16, a fragment or derivative thereof, to prepare an antisense molecule.

In order to exert the desired function, i.e. reducing the expression of DRR in glioma cells, the therapeutic molecules (antisense oligonucleotides, antisense RNAs, aptamers, ribozymes and so on) according to the invention are prepared from ribonucleic acids of the present invention as defined above, are delivered into target cells, preferably human GBM cells.

There are several well-known methods of introducing (ribo)nucleic acids into animal cells, any of which may be used in the present invention and which depend on the host. At the simplest, the nucleic acid can be directly injected into the target cell/target tissue. Other methods include fusion of the recipient cell with bacterial protoplasts containing the nucleic acid, the use of compositions like calcium chloride, rubidium chloride, lithium chloride, calcium phosphate, DEAE dextran, cationic lipids or liposomes or methods like receptor-mediated endocytosis, biolistic particle bombardment ("gene gun" method), infection with viral vectors, electroporation, and the like. Other techniques or methods which are suitable for delivering therapeutic molecules are known in the art. Convection-enhanced delivery (as detailed by Kawakami et al., *J Neurosurg* 101:1004-1011, 2004) of stabilized molecules can also be used. Another possibility is the use of implantable drug-releasing biodegradable microspheres, as those reviewed by Menei and Benoit, *Acta Neurochir* 88:51-55, 2003. It shall be clear that also a combination of different above-mentioned delivery modes or methods may be used. Another approach is to use either an Ommaya reservoir (micropumps) delivering the nucleic acid molecules versus encapsulated nucleic acid molecules in biodegradable microspheres, or both approaches at the same time.

The main obstacle to achieve in vivo gene silencing with therapeutic molecules, such as antisense technology, is delivery. To improve thermal stability, resistance to nuclease digestion and to enhance cellular uptake of the nucleic acids, various approaches have been tested in the art. These include chemical modifications like locked nucleic acid, phosphorothioate substitution, 2'-fluoro substitution, 2'-O-methyl substitution, encapsulation of nucleic acid molecules in various types of liposomes (immunoliposomes, PEGylated (immuno) liposomes), cationic lipids and polymers, nanoparticules or dendrimers, poly(lactic-Co-Glycolic Acid) polymeric microspheres, implantable drug-releasing biodegradable microspheres, co-injection of the nucleic acid molecules with a protective agent, and so on. It shall be understood that these methods and others known in the art may be used in the methods of the present invention.

In one aspect, the nucleic acid molecules of the present invention, optionally stabilized, encapsulated or otherwise modified as above, are delivered at the site of the tumor, e.g., the primary tumor and/or metastases. A manner of achieving localized delivery is the use of the Ommaya reservoir as described elsewhere. Another way of targeting the present nucleic acid molecules to tumor cells is to use antibody-directed, cell type-specific delivery. For example, some nucleic acids can be complexed with Fab specifically recognizing tumor cells, such as Fab-protamine-complexes (Song et al., *Nat Biotechnol* 23:709-717, 2005), or may be encapsulated in immunoliposomes. Such antibody-targeted nucleic acid molecules, e.g., in the form of nanoparticles, can be administrated by various means, such as systemic administration (i.v. injection, subcutaneous injection, intramuscular injection, oral administration, nasal inhalation, etc.) or locally, e.g., using an Ommaya reservoir. In particular, convection delivery with injection at a remote date or at the time of surgery may be used. Inhalative administration of the present nucleic acid molecules, e.g., in the form of nasal sprays or aerosol mixtures, may also be employed. Another option is use of nanotechnology for delivery.

In vivo delivery of nucleic acid molecules has been described, e.g., intravenous, intracerebroventricular or intranasal administration of naked or lipid-encapsulated nucleic acid molecules. Intravenous administration of vectors encapsulated in immunoliposomes or in viral particles have also been described and are known in the art.

The effect of a therapeutic nucleic acid molecule, i.e. the reduction of the expression of a target gene, may be only transient when the molecules are directly applied to cells as for instance described above. In some cases it can be advantageous if a nucleic acid encoding the respective nucleic acid molecule is integrated in an expression vector. Providing suitable elements, as described hereinafter, the DNA is transcribed into the corresponding RNA which is capable of forming the desired antisense molecule.

Thus, according to a further aspect of the present invention, expression constructs are provided to facilitate introduction into a host cell and/or facilitate expression and/or facilitate maintenance of the nucleotide sequence encoding the therapeutic molecules according to the invention. The expression constructs may be inserted into a plasmid, a virus, or a vector, which may be commercially available. In another embodiment, the invention therefore relates to the use of a DNA sequence to prepare an RNA molecule as defined herein. For example, the DNA sequences may comprise the DNA sequences which correspond to or encode the RNA sequences depicted in SEQ ID NOs: 1, 2, 5, 6, 7, 8, 9, 10, 14, 15 or 16, a linker, and the sequence complementary to the DNA. The linker is preferably 4 to 15 nucleotides in length, more preferably the linker is 4 to 10 nucleotides long and most preferably it is 4 to 8 nucleotides long. The linker can consist of any suitable nucleotide sequence. In one embodiment, the DNA sequences consist of 15 nt sequences derived from the DRR gene which are separated by a 4 to 15 nucleotide linker, from the reverse complement of the same 15 nt sequences and showing an tt(t) sequence at its 3' end. In another embodiment, the DNA sequences are inserted into an expression vector suitable for use in the methods provided herein.

Expression vectors, capable of giving rise to transcripts which form therapeutic nucleic acids as defined herein, can for instance be cloning vectors, binary vectors or integrating vectors. The invention thus also relates to a vector comprising any of the DNA sequences described herein. The expression vector is preferably a eukaryotic expression vector, or a retroviral vector, a plasmid, bacteriophage, or any other vector typically used in the biotechnology field. Such vectors are known to the person skilled in the art. If necessary or desired, the DNA nucleic acid can be operatively linked to regulatory elements which direct the synthesis of mRNA in eukaryotic cells.

To drive the expression of RNA these vectors usually contain an RNA Polymerase I, an RNA Polymerase II, an RNA Polymerase III, T7 RNA polymerase or SP6 RNA polymerase and preferably RNA polymerase III promoters, such as the H1 or U6 promoter, since RNA polymerase III expresses relatively large amounts of small RNAs in mammalian cells and terminates transcription upon incorporating a string of 3-6 uridines. Type III promoters lie completely upstream of the sequence being transcribed which eliminates any need to include promoter sequence in the therapeutic molecule. Optionally, one or more transcription termination sequences may also be incorporated in the expression vector. The term "transcription termination sequence" encompasses a control sequence at the end of a transcriptional unit, which signals 3' processing and poly-adenylation of a primary transcript and termination of transcription. Additional regulatory elements, such as transcriptional or translational enhancers, may be incorporated in the expression construct.

For therapeutic purposes, the use of retroviral vectors has been proven in some cases to be most appropriate to deliver a desired nucleic acid into a target cell. It shall be understood that retroviral vectors or adenoviral vectors, of which many are known in the art, may also be used in the vectors, compositions and methods provided herein. It shall also be understood that expression vectors containing the DNA sequences of the present invention can be introduced into the target cell by any of the delivery methods described above or otherwise known in the art.

Uses, Compositions and Kits

The therapeutic molecules and/or vectors according to the present invention may be used as a medicament for treating cancer, preferably glioma, more preferably glioblastoma, or for the manufacture of a medicament for treating cancer, preferably glioma, more preferably glioblastoma. The therapeutic molecules and/or vectors according to the present invention may also be used as a medicament for delaying the progression of cancer, for example glioma, such as glioblastoma. The term "delaying the progression of cancer" as used herein, refers to a delay in cancer re-growth by more than 30%, or by more than 50%, or by more than 70% and/or to an increase in the survival periods of affected subjects. In an embodiment, the therapeutic molecules and/or vectors according to the present invention may be used to inhibit brain cancer invasion, for example malignant glial cell (MGC) invasion.

The therapeutic molecules and/or vectors according to the present invention may be used alone or in combination with other cancer therapies. Non-limiting examples of other cancer therapies include resection of the cancer, chemotherapy, radiation therapy, immunotherapy, and/or gene-based therapy. The term "resection" refers to the surgical removal or excision of part or all of the tumor. The term "radiation therapy" refers to the treatment of cancer using radiation. The term "chemotherapy" refers to the treatment of cancer with chemical substances, so-called chemotherapeutics. The term "immunotherapy" as used herein refers to the stimulation of the reactivity of the immune system towards eliminating the cancer cells by using immunotherapeutics. The term "gene-based therapy" refers to the treatment of cancer based upon the transfer of genetic material (DNA, or possibly RNA) into an individual. Examples of such other cancer therapies include: chemotherapeutics including but not limited to temozolomide, vincristine, vinorelbine, procarbazine, carmustine, lomustine, taxol, taxotere, tamoxifen, retinoic acid, 5-fluorouracil, cyclophosphamide and thalidomide; immunotherapeutics such as but not limited to activated T cells and pulsed dendritic cells; gene transfer of CD3, CD7 and CD45 in glioma cells, concomitantly with the delivery of an RNA molecule as defined herein.

The therapeutic molecules and/or vectors according to the present invention may be administered alone or in combination with one or more additional cancer therapy. The latter can be administered before, after or simultaneously with the administration of the therapeutic molecules and/or expression vectors.

A further object of the present invention are pharmaceutical preparations which comprise a therapeutically effective amount of a therapeutic molecule, e.g., an antisense oligonucleotide and/or expression vector of the invention, and a pharmaceutically acceptable carrier. The term "therapeutically effective amount" as used herein means that amount of therapeutic molecule(s) and/or expression vector(s) that elicits the biological or medicinal response in a tissue, system, animal or human that is being sought by a researcher, veterinarian, medical doctor or other clinician.

In another embodiment, the invention therefore relates to a pharmaceutical composition for the treatment of cancer, preferably glioma, and more preferably glioblastoma, comprising a therapeutic molecule and/or expression vector according to the invention, and a pharmaceutically acceptable carrier. In yet another embodiment, the invention relates to a pharmaceutical composition for the delay of progression of cancer, preferably glioma, and more preferably glioblastoma, comprising a therapeutic molecule and/or expression vector according to the invention, and a pharmaceutically acceptable carrier. In a further embodiment, the invention relates to a pharmaceutical composition for the inhibition of cancer invasion, preferably glioma, and more preferably glioblastoma, comprising a therapeutic molecule and/or expression vector according to the invention, and a pharmaceutically acceptable carrier. In one embodiment, the invention relates to a pharmaceutical composition for the inhibition of malignant glial cell (MGC) invasion.

The pharmaceutical composition according to the invention may further comprise at least one additional cancer therapeutic, as discussed above.

The pharmaceutical composition according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or wafers.

The preparation of the pharmaceutical compositions can be carried out as known in the art. For example, the therapeutic molecule and/or the active compound, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human medicine. The pharmaceutical preparations can also contain additives, of which many are known in the art, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier may be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, an oligonucleotide of the invention can be administered in a time release formulation, for example in a composition which includes a slow release polymer. The modified oligonucleotide can be prepared with carriers that will protect the modified oligonucleotide against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG).

Many methods for the preparation of such formulations are patented or generally known to those skilled in the art. Sterile injectable solutions can be prepared by incorporating an active compound, such as a therapeutic molecule of the invention, in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. Therapeutic molecules of the invention may also be formulated with one or more additional compounds that enhance their solubility.

The dosage or amount of a therapeutic molecule and/or expression vector used, alone or in combination with one or more active compounds to be administered, depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to the therapeutic molecule and/or expression vector. It shall be understood that dosing and administration regimens are within the purview of the skilled artisan.

In another embodiment, the invention provides a kit comprising a RNA therapeutic or expression vector or a pharmaceutical composition according to the invention, and instructions for use thereof.

Therapeutic Methods

Without intending to be limited by theory, the present inventors contemplate that the therapeutic benefits of knocking-down and thus significantly reducing DRR expression in tumor cells may be mediated by inhibiting the invasion of the tumor into the brain, for example by inhibiting malignant glial cell (MGC) invasion, so as to reduce or delay the cancer invasion into adjacent healthy tissues (e.g., the brain in the case of glioma), based on the inventors' novel and unexpected findings that DRR is highly expressed in the invasive component of malignant gliomas and drives MGC invasion in both in vivo and in vitro invasion assays.

Cell invasion requires a cycle of events that utilizes both the actin cytoskeleton and MTs along with the continuous formation and disassembly of FAs. The role of MTs in FA turnover has been well established, and accumulating evidence suggests that MTs grow towards FAs in a process that is coordinated by F-actin. Much less is known about the constituents of FAs in normal glial cells and gliomas, and the molecular mechanisms that regulate FA turnover in normal glial cells and gliomas have not been described.

Our findings reported herein suggest that the de novo expression of DRR observed in invasive MGCs leads to more rapid FA disassembly and thus invasion. The inability of MGCs to separate from the tumor mass when the DRR-actin association is abolished has clinical implications. Indeed, a CD151-specific metastasis blocking monoclonal antibody has been shown to inhibit metastasis by preventing cell rear retraction and thus cell detachment and migration from the primary tumor mass (Zijlstra et al., *Cancer Cell* 13:221-34.2008).

Malignant glioma invasion is a primary cause of brain cancer treatment failure. We report herein the development of a novel functional screening strategy and identification of downregulated in renal cell carcinoma (DRR) as a regulator of invasion. We show herein that: DRR drives invasion in vitro and in vivo; although not expressed in normal glial cells, DRR is highly expressed in the invasive component of gliomas; DRR associates with and organizes the actin and microtubular cytoskeletons; and these associations of DRR with the actin and microtubular cytoskeletons are essential for focal adhesion (FA) disassembly and cell invasion. Our results provide evidence in support of the view that MTs facilitate FA disassembly and identify DRR as a new player in this normal physiologic process. We have shown that DRR is a novel actin/MT crosslinker that regulates FA disassembly. In support, we show that DRR localizes to the actin cytoskeleton and FAs and interacts with the LC2 subunit MAP1A. We show that DRR expression organizes both the actin and MT cytoskeletons so that MTs approach FAs and promote their disassembly. DRR deficiency, or the disruption of this complex by abolishing DRR-actin or DRR-LC2 association, leads to a loss of coordination between actin and MTs, as well as the inability of MTs to reach FAs. These findings identify DRR as a new cytoskeletal crosslinker that regulates FA dynamics and cell movement.

In view of the above, the invention provides a method for treating cancer, such as glioma, for example glioblastoma, in a subject in need thereof, comprising administering a therapeutic molecule of the invention, a vector or a pharmaceutical composition as described herein to said subject. In another embodiment, the invention relates to a method for delaying the progression of cancer, such as glioma, for example glioblastoma, in a subject in need thereof, comprising administering a therapeutic molecule, a vector or a composition as provided herein to said subject. The term "subject" as used herein preferably refers to a human, but veterinary applications are also in the scope of the present invention targeting for example domestic livestock, laboratory or pet animals. The invention further provides methods for down-regulating DRR expression, for example decreasing DRR expression by more than 50%, by more than 70%, or by more than 90%. In an embodiment, DRR expression is decreased or reduced by about 50%, about 60%, about 70%, about 80%, or about 90%. In another embodiment, the invention relates to a method for inhibiting or reducing the migration or invasiveness of tumor cells, preferably cells of glioma such as glioblastoma, comprising administering a therapeutic molecule, a vector or a composition of the invention to a subject in need thereof.

The invention further provides a method for enhancing the efficacy of cancer therapies for the treatment of cancer, in particular glioma (preferably glioblastoma), selected from the group comprising resection, chemotherapy, radiation therapy, immunotherapy, and/or gene therapy, comprising administering a therapeutic molecule, a vector or a composition as defined herein, and simultaneously, separately or sequentially administrating said cancer therapy. The term "enhancing the efficacy of a cancer therapy", as used herein, refers to an improvement of conventional cancer treatments and includes reduction of the amount of the anti-cancer composition which is applied during the conventional cancer treatment, e.g. amount of radiation in radiotherapy, of chemotherapeutics in chemotherapy, of immunotherapeutics in immunotherapy or of vectors in gene based therapies, and/or to an increase in efficacy of the conventional therapy and the anti-cancer composition when applied at conventional doses or amounts during the conventional cancer therapy. In one embodiment, enhancing the efficacy of a cancer therapy refers to prolonging the survival rate of subjects receiving the therapy.

There is also provided herein the use of DRR as a biomarker for invasive brain cancer cells. Detection of elevated DRR expression can be used to identify invasive tumor cells and for diagnosis and/or prognosis of a tumor, based on DRR expression. Accordingly methods for diagnosis and prognosis of malignant glioma are provided, along with use of DRR as a biomarker for invasiveness.

Kits for use in diagnostic and prognostic applications are also provided. Such kits can comprise a carrier, package or container that is compartmentalized to receive one or more containers such as vials, tubes, and the like, each of the container(s) comprising one of the separate elements to be used in the method. For example, the container(s) can comprise a probe that is or can be detectably labeled. The probe can be, for example, an antibody specific for the DRR biomarker or an RNA specifically hybridizing to DRR. The kit can also include a container comprising a reporter-means, such as a biotin-binding protein, e.g., avidin or streptavidin, bound to a detectable label, e.g., an enzymatic, florescent, or radioisotope label. The kit can include all or part of the amino acid sequence of the biomarker protein, or a nucleic acid molecule that encodes such amino acid sequences, or a nucleic acid molecule that binds to the mRNA of the DRR biomarker, or a nucleic acid molecule that encodes a nucleic acid molecule binding to the mRNA of the DRR biomarker.

The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific application. Directions and or other information can also be included on an insert which is included with the kit.

In one embodiment, the invention provides a kit comprising at least one agent that binds the DRR protein or the DRR mRNA; and instructions for use of the at least one agent for determining invasiveness of brain cancer cells in a subject.

In summary, the present invention, relates to the use of an anti-DRR therapeutic approach to treat malignant gliomas. The present therapeutic approach is based on the use of anti-DRR molecules relating to antisense-, viral-vector-, or any other related approaches aiming to knock-down DRR expression in human tumor cells. The technical feasibility of the present approach is further illustrated by means of the following non-limiting examples.

EXAMPLES

The present invention will be more readily understood by referring to the following examples, which are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention.

Materials and Methods

Functional Screening Assay

A normal human adult brain cDNA library (Clontech) was subcloned into the pLib retroviral vector (Clontech) and used to transfect the PT67 packaging cell line using Lipofectamine PLUS reagent (Clontech). The secreted replication deficient retrovirus was collected from the supernatant 24-72 hours post transfection and used to consecutively transduce, over a 72 hour time course, the WT-U251 glial cell line (FIG. 1A).

Human Glioma Analysis

Human glioma samples were obtained from the Brain Tumor Research Centre Tissue Bank at the Montreal Neurological Institute and Hospital (Montreal, Quebec, Canada). Written consent was obtained from all patients and the project was approved by the Institutional Ethics Board at the Montreal Neurological Institute and Hospital.

Cells

U251 human oligodendroglioma cell line (WT), human glial tumor cell line (U343MG), rat astrocytoma cell line (C6), DRR$^-$ and DRR$^+$ cells were cultured in DMEM high-glucose supplemented with 10% FBS and a penicillin-streptomycin antibiotic mixture. Human glioblastoma cell line (U87MG) (Cavanee lab, University of California at San Diego) were grown in DMEM high-glucose supplemented with 10% inactivated FBS and a penicillin-streptomycin antibiotic mixture.

Antibodies and Reagents

Affinity-purified rabbit polyclonal anti-DRR antibody directed against amino acids 67-92 was generated by Covance. Mouse anti-vinculin and mouse anti-tubulin antibodies, nocodazole, and G418 were purchased from Sigma. Rat anti-tubulin and mouse anti-GFAP antibodies were purchased from Chemicon. Rhodamine-phalloidin, rabbit anti-FAKpY$^{397}$ and Alexa 488-, 694-, and 647-conjugated secondary antibodies, and lipofectamine 2000 were purchased from Invitrogen. Chicken anti-MAP2 antibody was purchased from Encor Biotechnology Inc. GFP-paxillin cDNA plasmid was a generous gift from Dr. I. R. Nabi (University of British Columbia).

Human Glioma Immunolabelling

Fixed paraffin-embedded tissue was sectioned at 5 μm and mounted. Slides underwent heat-induced epitope-retrieval in citrate buffer (pH 6.0, Lab Vision), at 120° C. under high pressure for 10 minutes. All labeling was performed at room temperature on a Lab Vision 360 Autostainer. Antibody binding was amplified using Streptavidin or LV-polymer conjugated to HRP, and visualized using AEC chromogen (Lab Vision). All sections were counterstained with Surgipath 560 hematoxylin, and mounted with Aquatex. DRR antibody controls include antigenic peptide competition, immunolabelling with preimmune serum and single secondary antibody immunolabelling.

Cells

DRR$^-$ cell lines were generated using short hairpin RNAs (Paddison et al., 2002) and retroviral transduction. The distal C-terminal sequence (GCTCTCTCTCTTCGCCGGC-CAATGCGGCA) was used to generate the short hairpin loop. RT-PCR was used to confirm reduced DRR mRNA levels and western blotting was used to demonstrate reduced protein levels. DRR$^{\Delta PEPE}$ and DRR$^{\Delta HRE}$ constructs were generated using the Stratagene QuikChange Site-Directed Mutagenesis kit. DRR$^+$, DRR$^{\Delta PEPE}$ and DRR$^{\Delta HRE}$ stable cell lines were generated by transfecting WT-U251 cells with DRR, DRR$^{\Delta PEPE}$ or DRR$^{\Delta HRE}$ expression vectors using Lipofectamine 2000 following the manufacturer's protocol. 72 hours post-transfection cells were expanded and selected in DMEM supplemented with 0.6 mg/ml of G418 for 2 weeks. The resistant colonies were trypsinized and expanded in the selection media. E18-19 rat hippocampal neurons were a generous gift from Dr. P. McPherson (McGill University). Cells were fed every seven days with Neurobasal medium supplemented with B-27, N-2, l-glutamine (500 μM) and penicillin/streptomycin (100 units/ml) (Invitrogen).

Cell Proliferation, Migration and Invasion Assays

Cells were trypsinized and counted using the Coulter Z Series counter (Beckman-Coulter, Inc.). Measurements were taken twice for two samples of the same cell line and averaged. Cells were plated in a 6-well plate and counted after 24, 48, 72 and 96 hours. To assess 2D cell migration, cells were grown to confluency and a scratch was generated using a pipette tip. Images were captured at regular intervals 1-11 hours post scratch. Tumor spheroids were generated using the hanging drop method and implanted in a collagen type 1 matrix as previously described (Werbowetski-Ogilvie et al., *Cancer Research* 66:1464-1472, 2006). The implanted spheroids were imaged after the following time points (0, 24, 48 and 72 hours). Invading areas were measured by calculating the extreme diameter at 4 different angles and by subtracting the extreme diameter of the spheroids at time zero. All experiments were performed in triplicate and are from 3 independent experiments.

Figure 22:
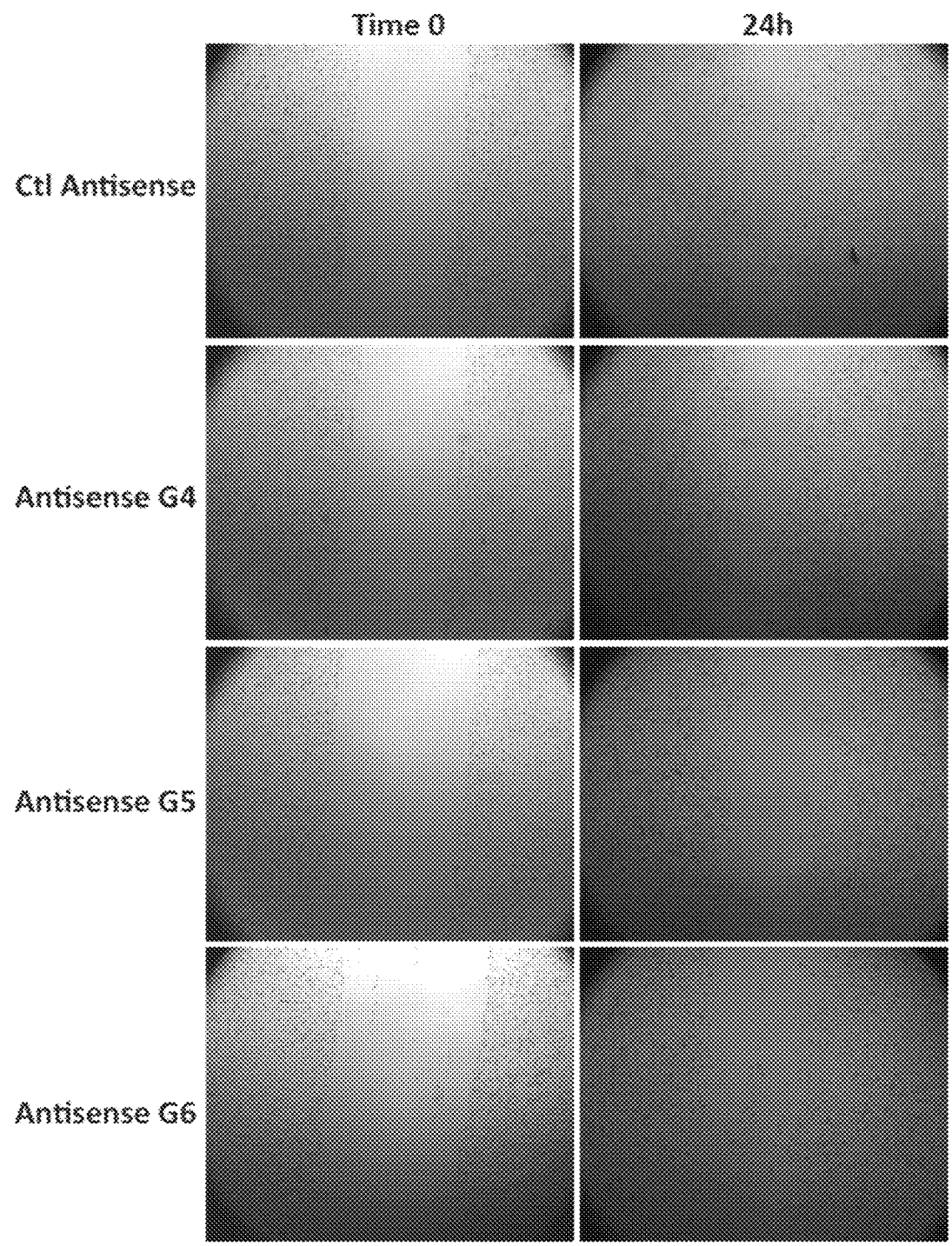
FIG. 22 shows the extent of human glioblastoma cell migration following reduction of DRR expression using an in vitro scratch assay. GBM6 cells were transfected with the indicated antisense (Antisense G4 (SEQ ID NO: 14), Antisense G5 (SEQ ID NO: 15), or Antisense G6 (SEQ ID NO: 16)) or a non-targeting control antisense (CTL Antisense (antisense G1/SEQ ID NO: 11)). Images of the scratch were acquired at 0 and 24 hours.

For the scratch assay shown in FIG. 22, the following procedure was used: Following 72 hours post-transfection, cells have reached a monolayer. A 200 μl pipette was used to perform a scratch. Cells were rinsed 3 times with PBS and fresh media was added to the cells. Images were captured with a 5× objective at the beginning of the scratch and at 24 hours and 48 hours. For each image, distances between one side of the scratch and the other were measured. The distance (μm) of cell migration was quantified by measuring the distance of the scratch at each time interval and subtracting it from the distance of the scratch at time zero.

Mouse Intracerebral Tumor Implantation

The mouse was secured to a stereotactic frame (Kopf Instruments) and a small incision was made in the scalp at the midline. A burr hole was created 0.5 mm anterior and 2 mm lateral to bregma. A microliter syringe (Hamilton Company) was slowly lowered through the burr hole to a depth of 4.4 mm and a cell suspension containing 2×10$^5$ cells in 3 μl of PBS was injected over 12 minutes. Animals were euthanized at one month post-injection to assess tumour growth and invasion.

Western Blot and Immunoprecipitation

To determine DRR expression levels in WT, DRR$^-$ and DRR$^+$ cells, cells were allowed to grow to 80% confluency, washed in cold PBS and lysed with RIPA buffer or 2% hot SDS. Lysates (30 μg) were separated on a 12% polyacrylamide gel and transferred to a nitrocellulose membrane. Membranes were probed with rabbit anti-DRR and mouse anti-tubulin antibodies followed by the appropriate HRP-conjugated secondary antibodies (Jackson ImmunoResearch). The ECL Plus™ reagent detection kit was used (Pierce). Immunoprecipitation experiments were performed in HEK-293 cells as previously described (Angers-Loustau et al., *Molecular Cancer Research* 2:595-605, 2004).

Mouse Intracerebral Tumor Implantation

All animal experimentation was approved by the Institution's Animal Care Committee and conformed to the guidelines of the Canadian Council of Animal Care. Six week old CD1 nu/nu athymic mice (Charles River, Canada) were anaesthetized by an intraperitoneal injection containing Ketamine, Xylazine and Acepromazine.

Yeast Two-Hybrid Screening

Yeast two-hybrid screens were performed using the Matchmaker™ Two-Hybrid System 3 (Clontech). Full-length DRR was used as the bait to screen a human brain cDNA library (Clontech).

Immunocytochemistry

Cells were grown on glass coverslips or on fibronectin (10 µg/ml) coated coverslips, fixed with 4% PFA and permeabilized with 0.5% TritonX-100 before being immunolabeled. The FA disassembly assay was performed as previously described (Ezratty E J et al., Nat. Cell Biol. 7:581-590, 2005). Briefly, cells were incubated in serum-free media for 24 h before being treated with nocodazole (10 µM; 4 h). The drug was washed out along a variable time course (5, 15, 30 and 60 min) using serum-free media. Fluorescently labeled cells were visualized with a Zeiss 510 confocal microscope (63× objective). The number and surface area of vinculin-stained focal adhesions were quantified using Image J software. At least 10 fields from three independent experiments were quantified.

For immunofluorescence studies, cells were fixed with 4% PFA and permeabilized with 0.5% TritonX-100 before being processed for immunostaining, as described above. Cells were labelled with mouse anti-vinculin to visualize focal adhesions and rhodamine-phalloidin was used to stain actin. Fluorescently labelled cells were visualized with a Zeiss 510 confocal microscope using 63× objectives.

Confocal Videomicroscopy

WT or DRR$^+$ cells were seeded on 35 mm glass bottom culture dishes (MatTek Corporation) before being transfected with GFP-paxillin. 24-48 h post-transfection the images were captured every 1 min for 170 minutes using a Zeiss 510 confocal microscope (63× objective). Five DRR$^+$ and five control (WT) cells were analyzed, and a total of 17 FAs were analyzed for DRR$^+$ cells. The apparent rate constants for the incorporation of GFP-paxillin into FAs and its disassembly from FAs was quantified using the technique described in Webb et al., 2004. Measurements were obtained from five cells, 5-10 FAs/cell. In control cells, no FAs were identified that assembled or disassembled within the 170 minute imaging interval. Data is presented as mean±standard error.

Primary Culture of Human Glioma

Tissues obtained from surgical resection were rinsed two times with Phosphate Buffered Saline 1× (PBS) before being transferred to cell culture dishes. Necrotic tissues and blood vessels were separated from the tumor. Tissues were then cut and incubated with 5 ml of 1.25% of trysin-EDTA for 30 minutes at 37° C., after which 7.5 ml of cell culture media (Dulbecco's modified Eagle's medium (DMEM) supplemented with 20% fetal bovine serum (FBS), 250 U/mL penicillin G, 250 µg/mL streptomycin sulfate, and 4.4 µg/mL amphotericin B (Fungizone)) was added to the sample to neutralize trypsin-EDTA. The sample was then transferred through to a cell strainer. 5 ml of cell culture media was added to the cell strainer and the process was repeated three times. The suspension was then centrifuged for 20 minutes at 1000 rpm at 4° C. to pellet the cells. The supernatant was discarded and the cell pellet was resuspended with 3 ml of erythrocyte lysing buffer (155 mM NH$_4$Cl/5.7 mM K$_2$HPO$_4$/0.1 mM EDTA, pH=7.3). The cells were incubated for 15 minutes at room temperature and then 15 ml of culture media was added to the sample, mixed thoroughly and centrifuged for 10 minutes at 1000 rpm. The supernatant was discarded and cells were resuspended in culture media. After which, cells were allowed to grow for a minimum of 2 weeks in DMEM supplemented with 20% FBS, 2× antibiotics before use. After 2 weeks, cells were cultured in DMEM supplemented with 10% FBS and 2× antibiotics. Cultures were maintained at 37° C. in a humidified atmosphere of 5% CO$_2$. Upon reaching confluency, cells were trypsinized using 0.05% trypsin-EDTA.

Cell Transfection and 3D Invasion Assay 50 000 cells were plated in a 6 well dish overnight and the next day, they were transfected with plasmid vector expressing GFP alone or DRR antisense using GeneJuice™ (Novagen) according to the manufacturer's instructions (2.5 µg DNA; 4 µl GeneJuice™ in 100 µl of OptiMEM). 72 h post-transfection, cells were detached by adding 0.5 ml of 0.05% Trypsin-EDTA to the wells and incubated for 30 second at 37° C. Cells were then neutralised with 1 ml of culture media, transferred to 15 ml tube and counted.

To generate tumor spheroids, drops (20 µl) of cell culture media containing 25 000 cells were suspended from an inverted Petri dish lid. 5 ml of PBS was added at the bottom of the dish to prevent evaporation of the drops. To form cell aggregates, the hanging drops were incubated for 72 h at 37° C. The aggregates were transferred to 2% agar/PBS (pH 7.4) coated Petri dishes containing 10 ml culture media and were incubated at 37° C. for another 48 h period to allow the aggregates to become round like a spheroid. Then, spheroids were implanted into a liquid collagen Type I solution (2.5 mg/ml 0.012N HCL) mixed with 10×DMEM and 0.1 mM NaOH at a ratio of (8:1:1). Collagen-containing spheroids were allowed to solidify at 37° C. for 30 min after which 0.5 ml of tissue culture media was added to each well. The implanted spheroids were imaged after the following time points: 0, 24, 48, 72 and 96 hours. Invading areas were measured by calculating the extreme diameter at 4 different angles and by subtracting the extreme diameter of the spheroids at time zero.

For experiments in FIGS. 17-22, transfection was carried out as follows: The day before transfection, cells were plated so as to reach 75% confluency at the time of transfection. Cell media was replaced with fresh media before transfection. Complexes of DRR oligomer and lipofectamine 2000 (Invitrogen) were prepared according to the manufacturer's instructions. Briefly, lipofectamine was gently mixed in opti-MEM and left at room temperature for 5 min. DRR oligomer was first mixed with opti-MEM (so that the final concentration added to the cells was 20 nM) and gently mixed with lipofectamine. Lipofectamine-DRR oligomer complexes were incubated at room temperature for 20 minutes before being added to the cells. The day after transfection, fresh cell media was added to the transfected cells. Cells were fixed or lysed following 72 hours post-transfection.

Antisense Oligonucleotide Synthesis

Standard phosphoramidite solid-phase synthesis conditions were used for the synthesis of all modified and unmodified oligonucleotides (Damha and Ogilvie, 1993, In Agrawal, S. (ed.), Protocols for Oligonucleotides and Analogs: Synthesis and Properties, Methods in Molecular Biology, Vol. 20, The Humana Press Inc., Totowa, N.J., pp/81-114). Syntheses were performed on an Applied Biosystems 3400 DNA Synthesizer at a 1 pmol scale using Unylink CPG support (ChemGenes). All phosphoramidites were prepared as 0.15M solutions in acetonitrile (ACN), except DNA, which was prepared as 0.1 M. 5-ethylthiotetrazole (0.25M in ACN) was used to activate phosphoramidites for coupling. Detritylations were accomplished with 3% trichloroacetic acid in CH$_2$Cl$_2$ for 110 s. Capping of failure sequences was achieved with acetic anhydride in tetrahydrofuran (THF) and 16% N-methylimidazole in THF. Sulphurizations were accomplished using a 0.1 M solution of xanthane hydride in 1:1 v/v pyridine/ACN. Coupling times were 110 s for DNA amidites (270 s for guanosine), and 600 s for 2'F-ANA phosphoramidites, with the exception of guanosine phosphoramidites which were allowed to couple for 900 s. Deprotection was accomplished with an on-column decyanoethylation step using anhydrous 2:3 TEA:ACN in three 15 min washes followed by an ACN wash. Deprotection and cleavage from the solid support was accomplished with either 3:1 NH4OH:EtOH for 48 h at room temperature (RT), or with 40% methylamine for 10 min at 65° C. (Belton, L., 2000, Curr. Protocols. Nucleic Acid Chem., 3.6.1-3.6.13).

Purification of crude oligonucleotides was done either by preparative denaturing polyacrylamide gel electrophoresis (PAGE) using 24% acrylamide gels, or by reverse phase HPLC on a Waters 1525 HPLC using a Varian Pursuit 5 reverse phase C18 column with a stationary phase of 100 mmol triethylammonium acetate in water with 5% ACN, and a mobile phase of HPLC-grade acetonitrile. Gel bands were extracted overnight in DEPC-treated autoclaved Millipore water, and lyophilized to dryness. All purified oligonucleotides were desalted with Nap-25 Sephadex columns from GE Healthcare. Sequences were verified by analytical denaturing PAGE and/or ESI-LCMS.

Sequences targeting DRR mRNA were designed using the published mRNA sequences available on the NCBI website. Effective antisense sequences targeting DRR were designed using an antisense oligonucleotide (AON) sequence selection tool available from IDT (http://www.idtdna.com/Scitools/Applications/AntiSense/Antisense.aspx?source=menu). Predicted antisense sequences were checked using BLAST alignment tools (NCBI) to check for absence of off-target hits. Additionally, mRNA secondary structure of a section of the DRR mRNA was predicted using the MFOLD tool (http://mfold.rna.albany.edu/?q=mfold/RNA-Folding-Form) to look for mRNA-accessibility for AON binding. AONs targeting DRR are shown in Table 1 (G4 (SEQ ID NO: 14), G5 (SEQ ID NO: 15), and G6 (SEQ ID NO: 16)), and control AONs not targeting DRR were also prepared for control experiments (G1 (SEQ ID NO: 11), G2 (SEQ ID NO: 12), G3 (SEQ ID NO: 13)). In addition to the DRR-targeting AON sequences provided herein, e.g., in Table 1, other DRR-targeting AON sequences could be selected using these methods by choosing sequences complementary to other DRR mRNA regions, while ensuring specificity for DRR mRNA but not other mRNA sequences. It should be understood that any antisense molecule, e.g., antisense oligonucleotide, which targets DRR and reduces or decreases DRR expression is encompassed.

Results

Functional Screening Assay Identifies DRR as a Promoter of Invasion

MGC invasiveness can be assayed using a 3D invasion model (Del Duca, D. et al., *Journal of Neurooncology* 67:295-303, 2004). Using this model as a starting point, we developed a novel functional screening assay by retrovirally transducing MGCs, the U251 glioma cell line, to express an entire brain cDNA library. We reasoned that if we could make a cell heterologously express a gene that promotes invasion, it would be distinguishable from other cells as a hyperinvasive cell. Tumor spheroids were generated from the transduced MGCs and their invasiveness was assessed in the 3D invasion model. Distinguishable hyperinvasive cells were then captured and expanded in culture and the originally transduced gene was identified (FIG. 1A). DRR was identified as a strong promoter of invasion using this forward genetic approach.

Figure 8:
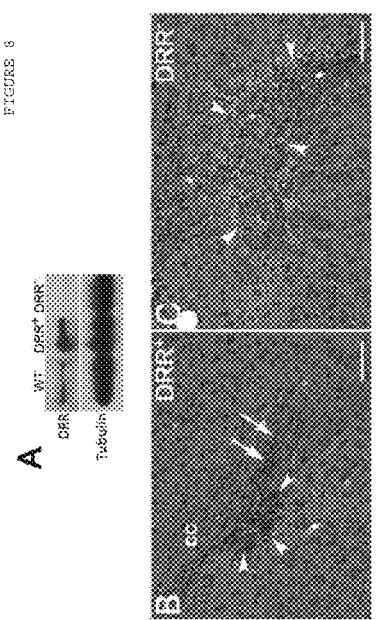
FIG. 8 shows DRR protein expression in DRR− and DRR+ stable cell lines. (A) shows protein blotting showing increased DRR expression in the DRR cell line and reduced DRR expression in the DRR− cell line in comparison to wild-type cells. (B) shows DRR cells implanted into mouse brain showing elongated cell shape and invasion into corpus callosum (cc). Arrows indicate MGCs that have invaded the corpus callosum. (C) shows DRR− cells implanted into mouse brain showing round cell shape and no evidence of invasion towards the corpus callosum. Arrowheads delineate tumor border. Bars=100 µm.
Figure 9:
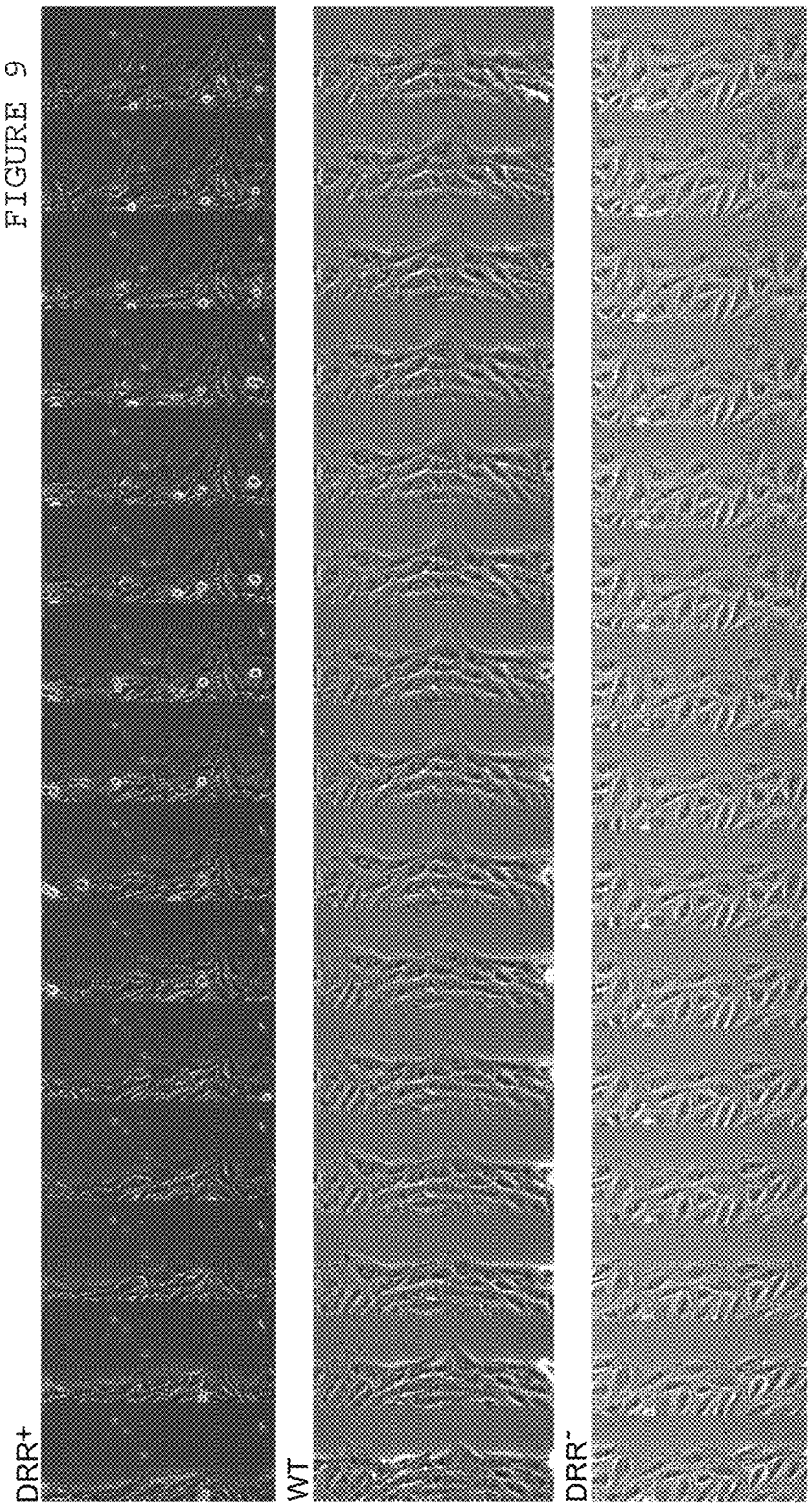
FIG. 9 shows that DRR regulates the morphology of migrating cells. The morphology of migrating DRR+, WT and DRR− cells was assessed in a 2D migration assay. Representative images captured over a 10 hour interval show that DRR cells extend long thin protrusions whereas WT and DRR− cells migrate using broad lamella.

To test whether or not DRR acts as an effector of MGC invasion, we generated composite tumor spheroids made up of both DRR-overexpressing MGCs (DRR$^+$, FIG. 8) and wild-type (WT) MGCs, and studied the invasion parameters of each cell line (FIG. 1B-E). While MGCs endogenously express DRR, DRR$^+$ cells invade 240% farther than WT cells. By contrast, reducing DRR expression in MGCs using RNA interference (DRR$^-$, FIG. 8) causes a significant decrease in invasion (FIGS. 1F, G & J). To test if reducing DRR expression decreases invasion in other glial cell lines, we developed U343-DRR$^-$, C6-DRR$^-$ and U87MG-DRR$^-$ and stable cell lines and tested their invasiveness. Compared to their wild-type counterparts which express endogenous DRR, all DRR$^-$ cell lines exhibited a significant reduction in their invasiveness (FIG. 11C-E). Interestingly, DRR expression also leads to a profound change in cell morphology as DRR$^+$ cells are elongated and spindle shaped whereas DRR$^-$ cells are round (FIGS. 1H, I, & K). Experiments in 2D migration assays also reveal differences in the morphology of cells as they migrate. DRR$^+$ cells migrate with long thin protrusions whereas WT and DRR$^-$ cells migrate with a uniform broad lamella (FIG. 9). An elongated spindle cell shape has been shown to be the preferred mode of MGC movement through brain (Beadle et al., *Mol Biol Cell.* 19:3357-68, 2008).

We next examined DRR's role as an invasion promoter in a mouse model. DRR$^+$ and DRR$^-$ tumors were implanted into the subcallosal/caudate region of mice and invasion was assessed (FIGS. 1L & M). DRR$^-$ tumors grow as a well circumscribed mass without invasion into the adjacent parenchyma, and these cells have a round morphology. Conversely, DRR$^+$ tumors are highly invasive. These invasive cells, which are distinguished by their large, hyperchromatic and elongated nuclei, have an elongated shape, separate from the tumor mass, invade parenchyma, and, importantly, move towards and into the corpus callosum. Invasion into white matter tracts such as the corpus callosum is a preferred invasion paradigm used by human malignant glial tumors (Pedersen et al., *Int. J. Cancer,* 62:767-71, 1995). Furthermore, DRR$^+$ tumors were smaller than DRR$^-$ tumors (FIG. 8B, C) suggesting a decrease in cell proliferation as previously described (Wang et al., *Genes Chromosomes Cancer* 27:1-10, 2000). We assessed the role of DRR in cell division and also found that cell division is inversely correlated with DRR expression (FIG. 1N). The notion that MGC invasion and proliferation are temporally exclusive events has been described (Giese et al., *Int J Cancer* 67:275-282.1996).

Thus, we have identified DRR as a regulator of cell movement and a driver of cell invasion. We have validated this finding in both in vitro and in vivo invasion assays, confirming the importance of DRR for cell invasion.

DRR is Expressed in Neurons and Human Gliomas but not in Normal Glia

Figure 2:
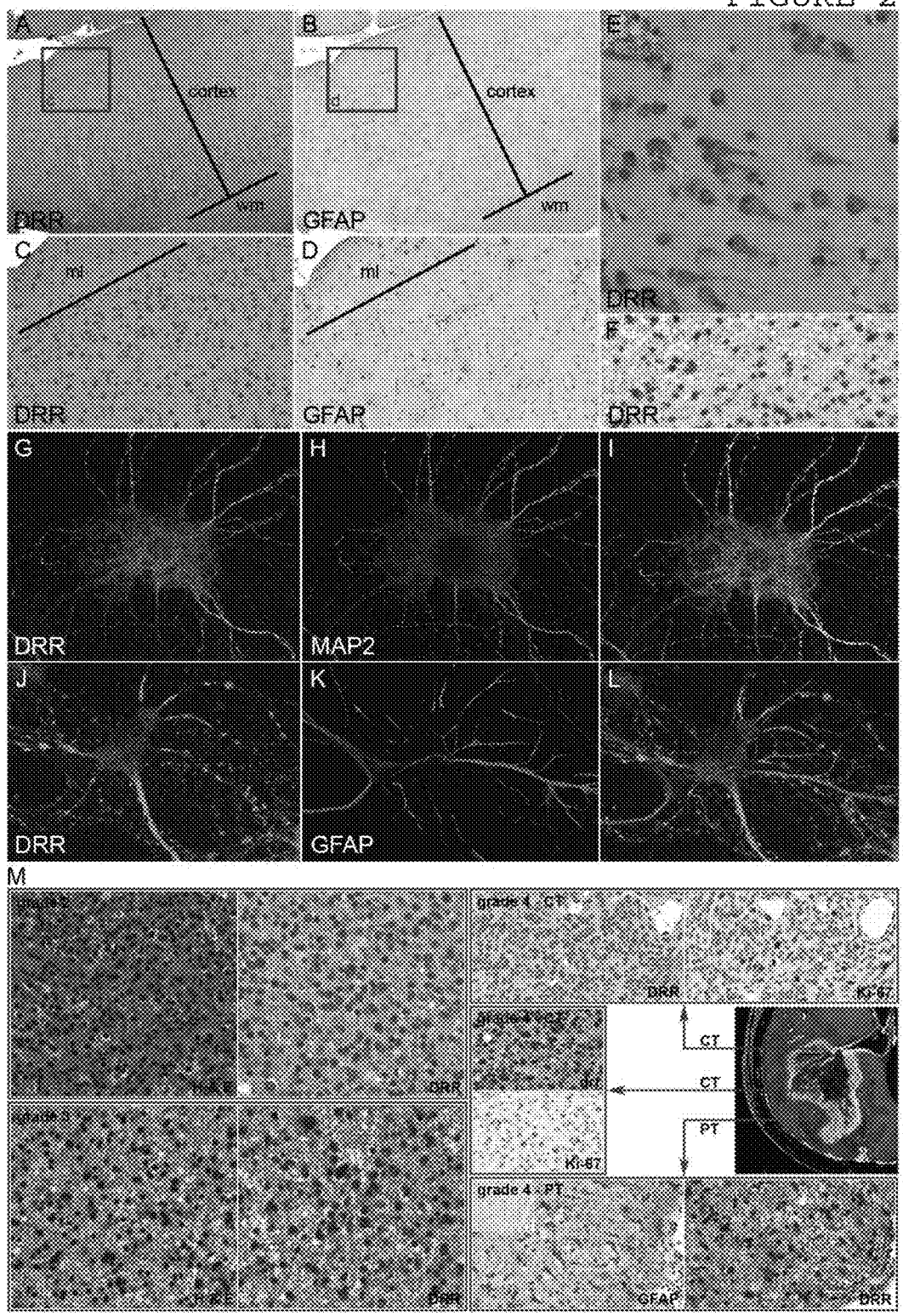
FIG. 2 shows that DRR is expressed in neurons and human gliomas but not in normal glia. DRR immunolabeling of normal human brain at low (A and B) and high (C and D) magnification shows that DRR is found within the cortex but not in white matter (wm). Expression of the glial marker GFAP does not overlap with DRR (A-D). DRR is not expressed in the aneuronal molecular layer (ml) of the cortex (C). High magnification imaging shows that DRR is highly expressed in neurons (E) but not in white matter (F). Rat brain cultures similarly show that DRR expression overlaps with the neuronal marker MAP2 in neurons (G-I) but not with the glial marker GFAP in glia (J-L). In (M), DRR expression in eight malignant gliomas of each grade was assessed. Both grade 2 and grade 3 gliomas (left panels, top and bottom) uniformly express high levels of DRR. In contrast, only the invasive peripheral tumor (PT) portions of grade 4 gliomas uniformly express DRR (right panel, bottom). The central tumor (CT) portion exhibits variable DRR expression, negative in 5 and positive in 3 tumors (right panel, top and middle). H & E: hematoxylin and eosin, Ki-67: marker of cell division revealing high levels of proliferation in the central tumor region.
Figure 10:
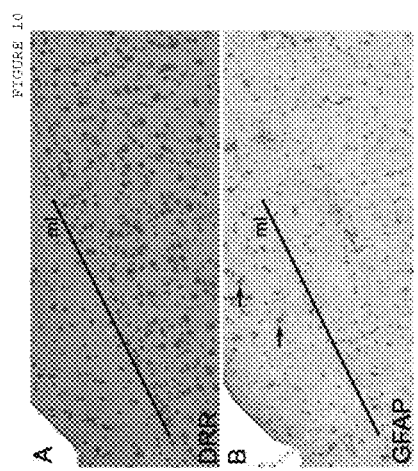
FIG. 10 shows DRR expression in human cortex. In (A) DRR immunolabelling of normal human brain cortex at high magnification shows that DRR is not expressed in the aneuronal molecular layer (ml). In (B) adjacent section GFAP immunolabelling shows the presence of astrocytes in the molecular layer (arrows) which are DRR negative.

To validate clinically our in vitro and in vivo findings, we determined the expression pattern of DRR in normal human brain and malignant gliomas. We found that in normal human brain, DRR is strongly expressed in neurons but not in astrocytes or in oligodendrocytes (FIG. 2A-F, see FIG. 10 for high magnification images). Co-labeling of cultured embryonic rat neurons and glia with neuronal and glial markers also shows that DRR is expressed in neurons but not in glial cells (FIG. 2G-L). DRR antibody controls including antigenic peptide competition, immunolabelling with pre-immune serum and single secondary antibody immunolabelling were negative. Analysis of DRR expression in 8 malignant gliomas of each grade indicates that DRR is highly but not uniformly expressed in all malignant glial tumors (FIG. 2M). Grade 2 and 3 gliomas, which are highly invasive tumors with low proliferation rates, uniformly express DRR. In contrast, grade 4 gliomas, which are both highly invasive and highly proliferative, express DRR in a suggestive pattern. The invasive peripheral tumor cells uniformly express DRR whereas the central proliferative tumor region showed variability in DRR expression. The central tumor in 5 out of 8 grade 4 gliomas showed little to no DRR expression, whereas the central tumor was DRR positive in 3 out of 8 tumors. Taken together, these data show that while DRR is not expressed in normal glial cells, it has a robust and differential expression pattern in malignant gliomas.

DRR Associates with the Cytoskeleton

Figure 3:
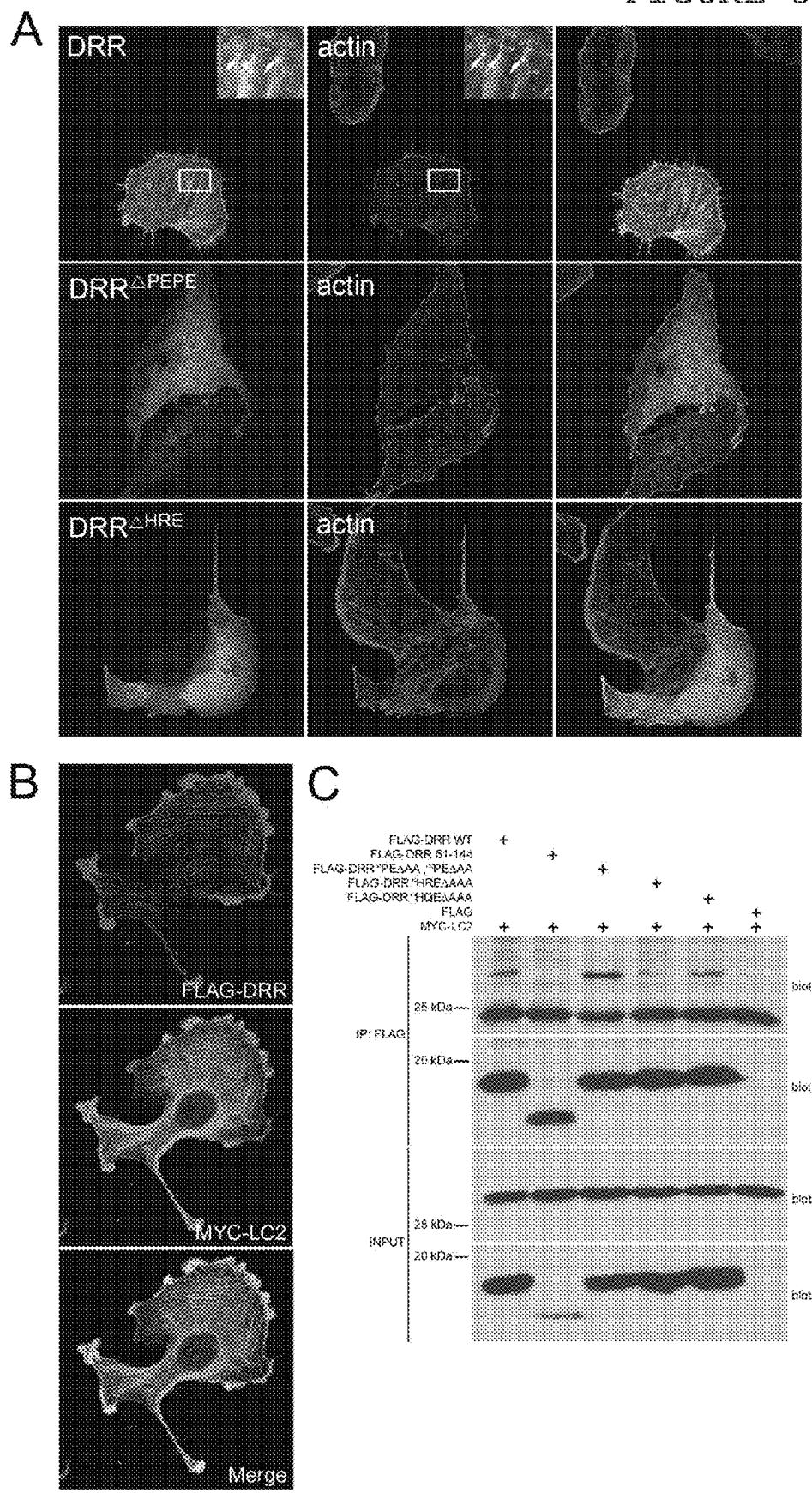
FIG. 3 shows that DRR associates with the actin cytoskeleton and interacts with LC2. (A) shows that transfected DRR localizes along actin stress fibers and focal adhesions. Arrows indicate expression at FA sites. Actin is labeled with phalloidin. The non-actin binding DRR$^{\Delta PEPE}$, and the non-LC2 binding DRR$^{\Delta HRE}$, are diffusely expressed in the cytoplasm. They do not localize to actin or FAs. DRR$^{\Delta HRE}$ can also be found in the nucleus. (B) shows co-localization of FLAG-DRR and MYC-LC2 along actin stress fibres, lamellipodia and membrane ruffles. (C) shows co-immunoprecipitation of heterologously expressed FLAG-DRR and MYC-LC2 from glial cells. MYC-LC2 co-immunoprecipitates with FLAG-DRR and FLAG-DRR$^{\Delta PEPE}$ but not when the conserved N-terminal HRE sequence, DRR$^{\Delta HRE}$, is mutated.
Figure 12:
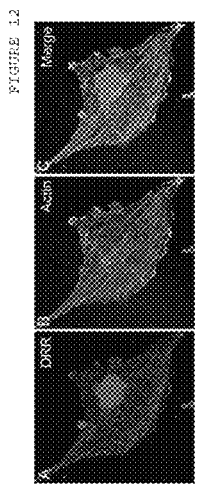
FIG. 12 shows localization of endogenous DRR in malignant glial cells. Immunolabeling wild-type U251 cells with the anti-DRR antibody reveals localization along actin stress fibers, FAs, membrane ruffles, and in the nucleus.

To uncover how DRR functions to drive cell movement, we localized DRR at the sub-cellular level. Endogenous or heterologously expressed DRR predominantly localizes along actin stress fibers, FAs and membrane ruffles (FIG. 3A). In agreement with a previous report (Wang et al., Genes Chromosomes Cancer 27:1-10, 2000), DRR can also be found in the nucleus (FIG. 12). These results suggest that DRR may be promoting invasion through a direct influence on the cytoskeletal apparatus or though a regulatory role in the nucleus.

Figure 13:
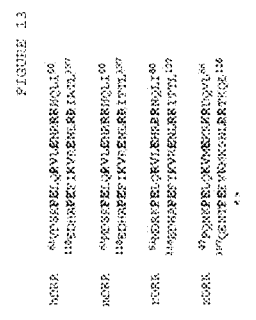
Figure 14:
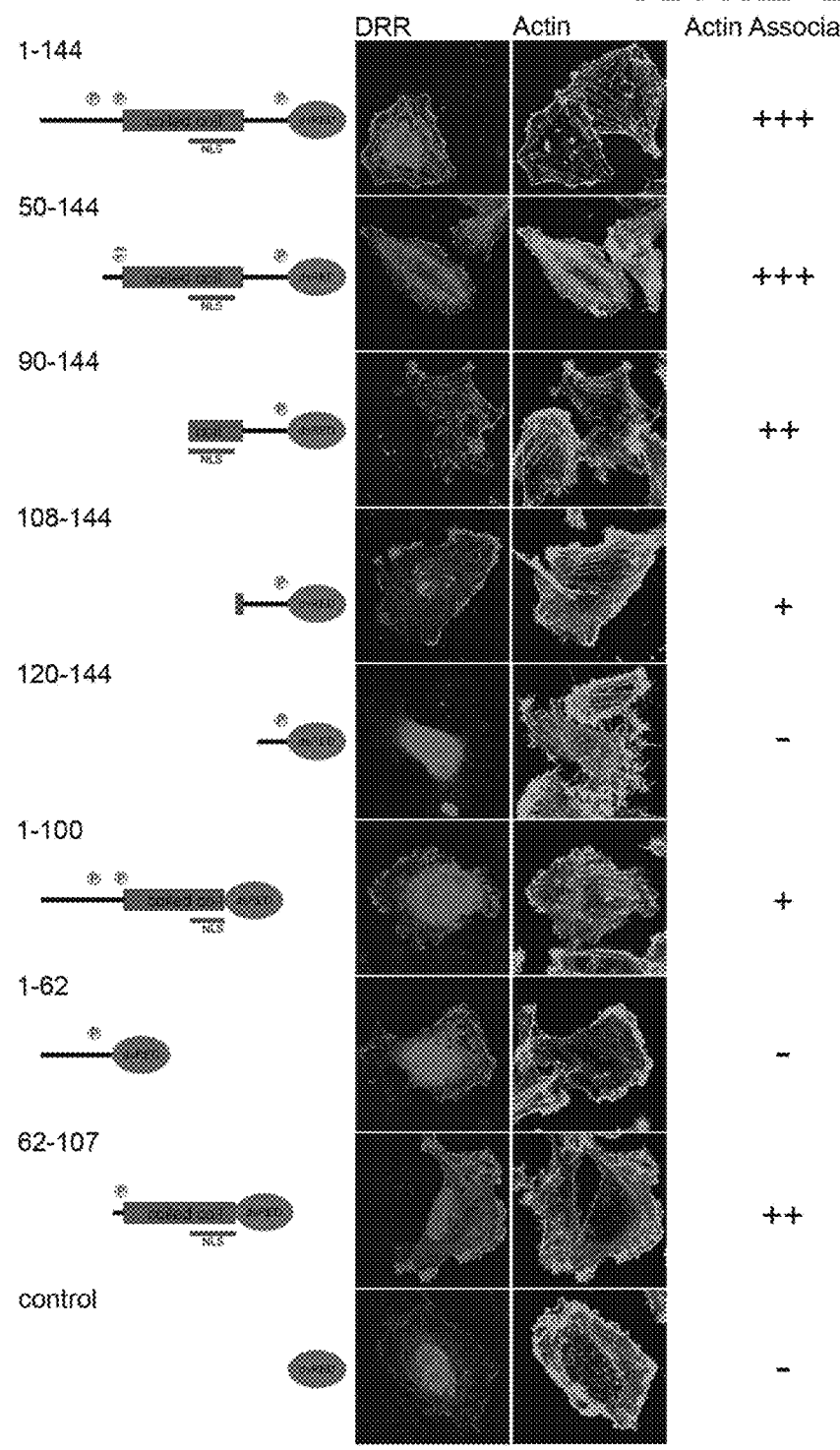
FIG. 14 shows truncation analysis to identify DRR regions required for stress fibre localization. dsRed was fused to the C-terminus of full length and truncated versions of DRR. The DRR-dsRED fusion proteins were expressed in WT U251 and assayed for stress fibre localization. These data show that amino acids 62-100 and 108-120 are required for stress fibre localization.
Figure 15:
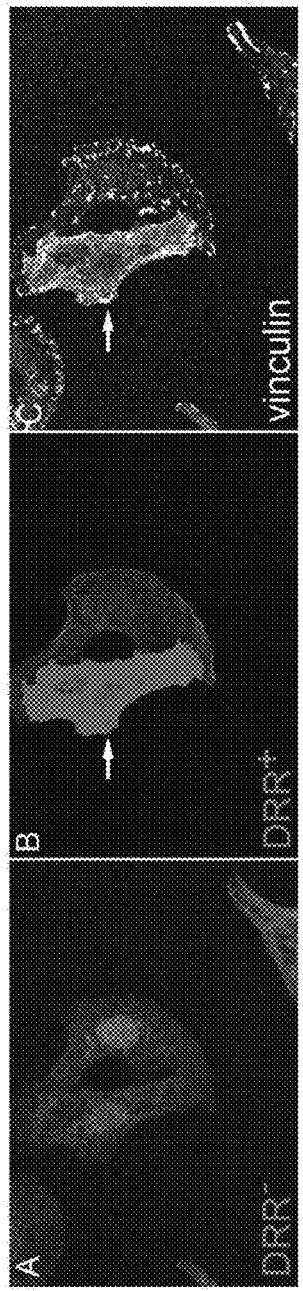
FIG. 15 shows that DRR reduction using RNA interference leads to specific on-target effects on focal adhesion dynamics. (A) shows U251 cells expressing GFP-RNAi targeting DRR, (B) shows DRR rescue cell transiently expressing DRR as identified by immunolabeling DRR (arrow), and in (C) FAs were visualized by immunolabeling vinculin. DRR FA phenotype (reduced FA size and increased FA number) can be rescued by expressing DRR in DRR⁻ cells.

To address this question, we uncoupled DRR from the actin cytoskeleton by identifying minimal domains required for actin association. Sequential N- and C-terminal truncated constructs of human DRR were generated and assayed for localization using fluorescent tags. Two minimal regions capable of actin association were identified, amino acids 62-100 and 108-120 (FIG. 14). We determined that domains required for actin association are conserved across species. We identified and mutated the amino acids within the 62-100 and 108-120 regions that were conserved across human, mouse, rat and zebrafish DRR (FIG. 13). The combined mutation of the conserved proline-glutamate (PE) motifs to alanines in both segments (DRR$^{\Delta PEPE}$) leads to a significant perturbation of the actin cytoskeleton and abolishes actin association with the remaining stress fibres (FIG. 3A). These findings indicate that cytoskeletal association of DRR is conserved across species.

In order to identify molecules that play a role in DRR association with the cytoskeleton, we used yeast two-hybrid screening of normal brain libraries to identify DRR binding partners. Using this assay, the light chain (LC2) subunit of MAP1A was identified as a candidate DRR binding protein. We have also shown that DRR and LC2 colocalize along actin stress fibers and membrane ruffles, and can be co-immunoprecipitated when heterologously expressed (FIGS. 3B and C), consistent with the association of these proteins. Interestingly, mutation of the DRR actin binding sites appears to increase DRR association with LC2 (FIG. 3B). We also found, in some cells, that the non-actin binding form of DRR (DRR$^{\Delta PEPE}$) can localize to microtubules (data not shown).

We then developed non-LC2 binding forms of DRR using truncation and amino acid mutagenesis analysis. A minimal N-terminal histidine-arginine-glutamate (HRE) sequence was found to be required for LC2 binding (FIG. 3B). When this region is mutated, DRR$^{\Delta HRE}$, there is a significant perturbation of the actin cytoskeleton and the localization pattern of DRR changes. There is an increase in DRR expression in the nucleus and diffuse cytoplasmic localization (FIG. 3A). Slight actin association was also observed.

In summary, the data show that DRR localizes to the actin cytoskeleton, FAs and nucleus. Minimal regions required for actin association (DRR$^{\Delta PEPE}$) have been defined. The LC2 subunit of MAP1A has been identified as a DRR associated protein, and this association can be disrupted by mutation of the amino terminal HRE region (DRR$^{\Delta HRE}$).

DRR Association with the Cytoskeleton is Required for Cell Movement

Figure 4:
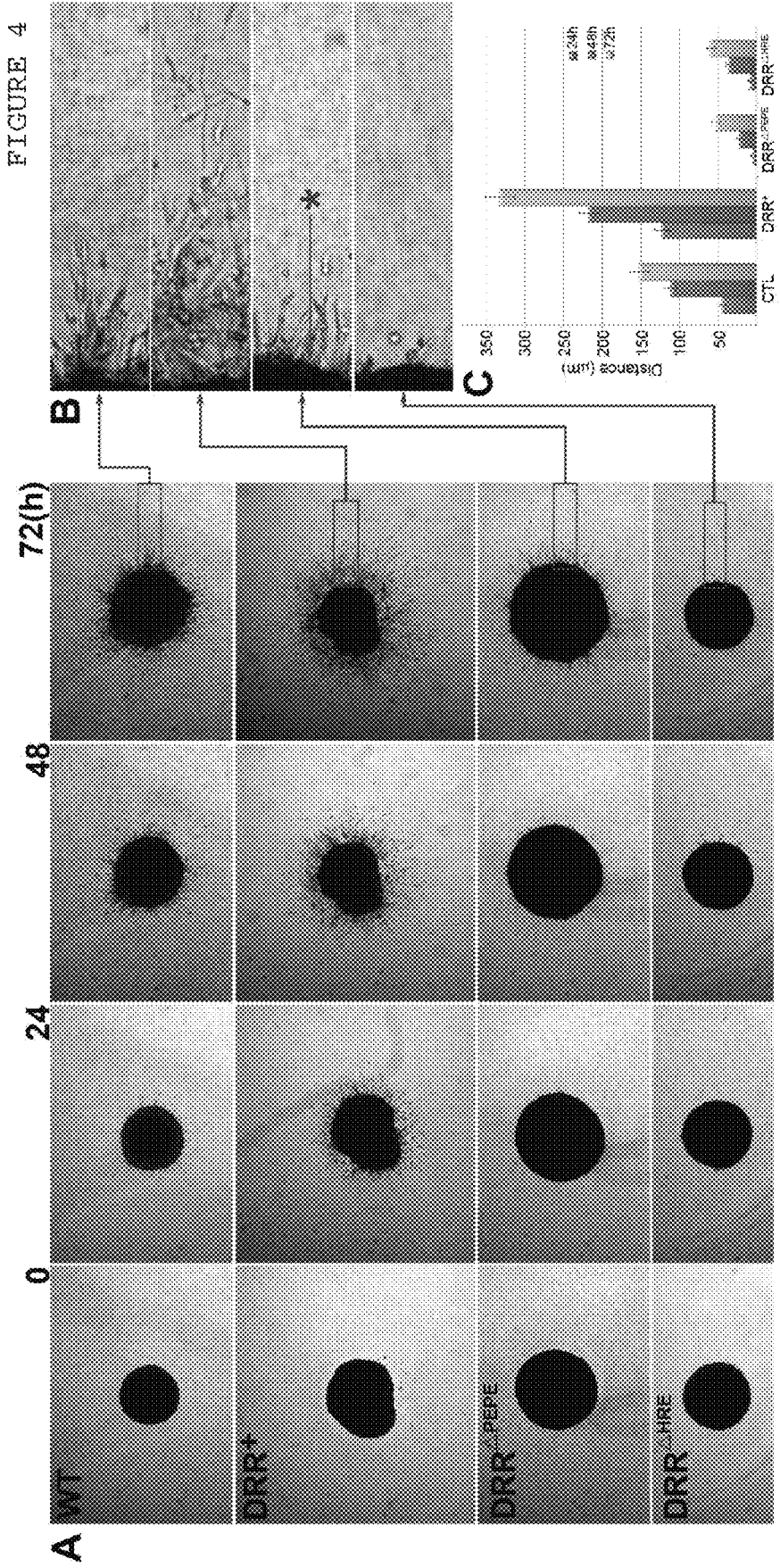
FIG. 4 shows that DRR association with actin and LC2 is required for cell invasion. (A) shows 3D invasion assays of WT, DRR+, DRR$^{\Delta PEPE}$ and DRR$^{\Delta HRE}$ in a 3D collagen matrix. (B) shows a closer view of the spheroid margins showing cell invasion. Asterisk indicates the spheroid edge in DRR$^{\Delta PEPE}$ cells. (C) Quantitative analysis of cell invasion after 24, 48 and 72 h.

The ability to disrupt the DRR-actin and DRR-LC2 associations provided two approaches to determine if DRR association with the cytoskeleton is required to drive cell movement. Stable cell lines expressing DRR$^{\Delta PEPE}$ or DRR$^{\Delta HRE}$ were generated and tested for invasiveness in a 3D invasion assay. We found that loss of the DRR-actin association leads to a ~3-fold reduction in invasion compared to WT cells, suggesting that this mutant form of DRR is acting as a functional dominant negative (FIG. 4). A similar finding is also seen when the DRR-LC2 interaction is disrupted (FIG. 4). Together, these data show that DRR association with actin and LC2 is required to drive cell invasion.

DRR Regulates Focal Adhesion Dynamics

Figure 5:
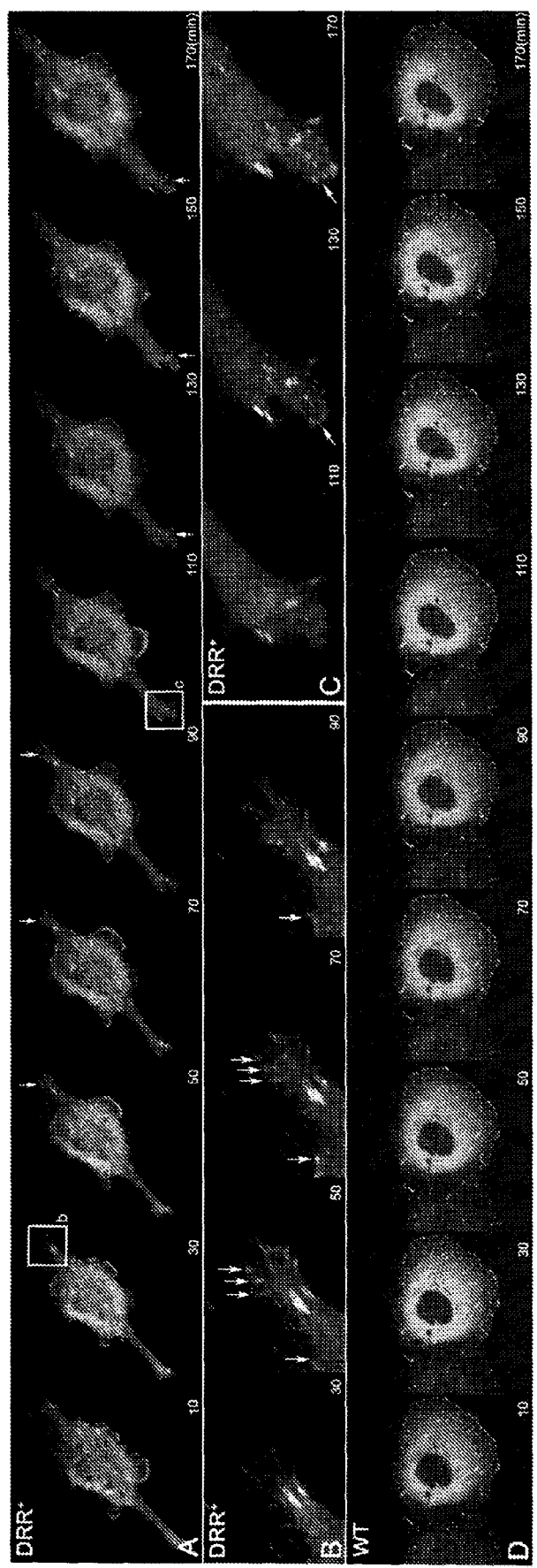
FIG. 5 shows that DRR promotes focal adhesion dynamics. DRR+ and WT cells were transfected with GFP-paxillin and imaged using confocal videomicroscopy for 170 minutes at 1 minute intervals. (A) shows DRR cells transfected with GFP-paxillin. Representative cell showing dynamic membrane protrusions and FA assembly and disassembly. Arrows indicate areas of robust FA assembly and disassembly. Boxes, b and c, represent high magnification areas shown in (B) and (C). (D) shows WT cell transfected with GFP-paxillin. Representative cell showing a lack of membrane protrusions and stable FAs. No FAs were identified that assembled or disassembled over the imaging interval.

The process of cell movement requires regulated FA dynamics (Lauffenburger et al., Cell 84:359-369, 1996; Friedl et al., Nat Rev Cancer 3:362-74, 2003). To determine if DRR expression affects FAs, we expressed a GFP-paxillin fusion protein and studied the effect of DRR expression on FA dynamics using confocal videomicroscopy (FIG. 5). In non-polarized DRR$^+$ cells we found that the total time taken for FAs to form and disassemble is 40.05±3.00 minutes (FIG. 5 A-C). The rate constant for GFP-paxillin incorporation into FAs was $(6.2\pm0.9)\times10^{-3}$ min$^{-1}$ and the rate constant for GFP-paxillin disassembly was $(8.6\pm0.7)\times10^{-3}$ min$^{-1}$. Conversely, FAs were not dynamic in WT control cells. We were unable to detect FAs that formed or disassembled within the 170 minute imaging interval (FIG. 5D). These data strongly support a mechanism whereby DRR drives cell invasion by enhancing FA dynamics.

It has been established that FA disassembly requires polymerized microtubules (MTs) (Kaverina et al., J. Cell Biol. 142:181-190, 1998; Kaverina et al., J. Cell Biol. 146:1033-1044, 1999; Krylyshkina et al., J. Cell Biol. 156:349-359, 2002; Krylyshkina et al., J. Cell Biol. 161:853-859, 2003; Ezratty et al., Nat. Cell Biol. 7:581-590, 2005). Since we have shown that DRR interacts with the LC2 subunit of MAP1A and that DRR overexpression leads to less stable FAs, we examined directly if DRR promotes FA disassembly.

MT control of FA disassembly can be examined using the microtubular depolymerizing agent nocodazole to disassemble microtubules. After nocodazole application, FAs increase in size since there are no microtubules available for disassembly. Upon nocodazole washout, microtubules polymerize and focal adhesions disassemble (Ezratty et al., Nat. Cell Biol. 7:581-590, 2005). We performed this experiment using DRR$^+$ and DRR$^-$ cells plated on the extracellular matrix component fibronectin. Two striking observations were made. First, upon nocodazole application and MT depolymerization, DRR$^+$ cells develop more and larger focal adhesions compared to non-treated cells (FIG. 6A). In contrast, we did not observe differences in FA number and size in nocodazole treated versus non-treated DRR$^-$ cells (FIG. 6A) or WT cells (data not shown), suggesting that DRR deficiency leads to large and mature FAs. Second, when MTs repolymerize in cells overexpressing DRR, FAs begin to disassemble within 5 minutes whereas FAs in DRR$^-$ cells (or WT cells, data not shown) only begin to disassemble after 15 minutes and do not completely disassemble (FIG. 6A). When the same experiment was performed with the non-actin binding form of DRR (DRR$^{\Delta PEPE}$) or the non-LC2 form of DRR (DRR$^{\Delta HRE}$) the FA disassembly kinetics were similar to DRR deficiency conditions (FIG. 6B, data not shown for DRR$^{\Delta HRE}$). The finding that DRR expression promotes FA disassembly whereas DRR deficiency leads to stable mature FAs points to DRR as a novel regulator of FA dynamics.

DRR Organizes the Actin and Microtubular Cytoskeletons

Figure 6:
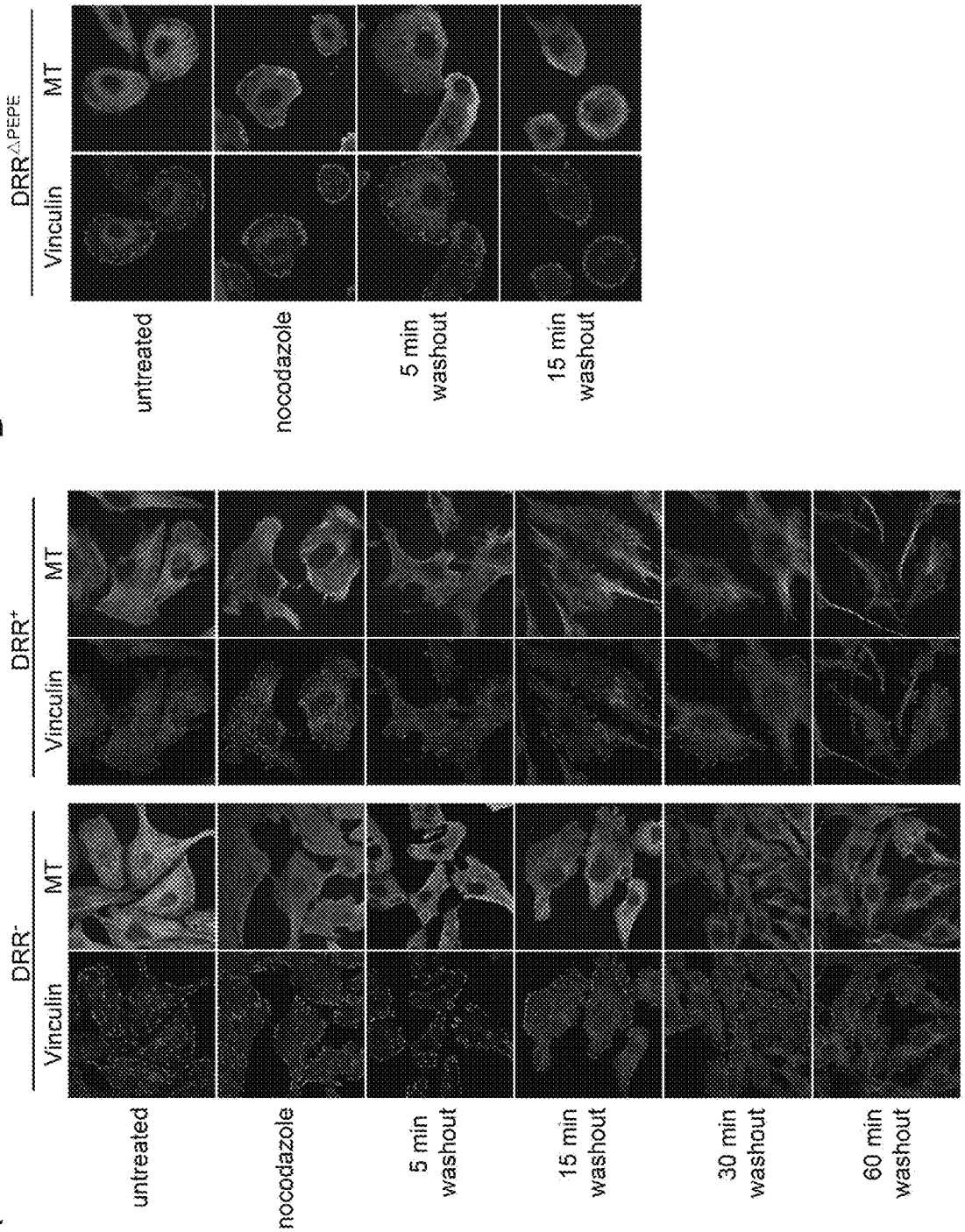
FIG. 6 shows that DRR promotes focal adhesion disassembly. DRR−, DRR+ (A) and DRR$^{\Delta PEPE}$ (B) were starved for 24 h and left untreated or treated for 4 h with 10 µM nocodazole. The MT depolymerizer was then washed out for the indicated time. DRR expression promotes FA disassembly whereas DRR deficiency leads to more stable FAs.

Results from the FA disassembly assay suggest that DRR association with both the actin cytoskeleton and the LC2 subunit of MAP1A are required for FA disassembly (FIG. 6).

Figure 7:
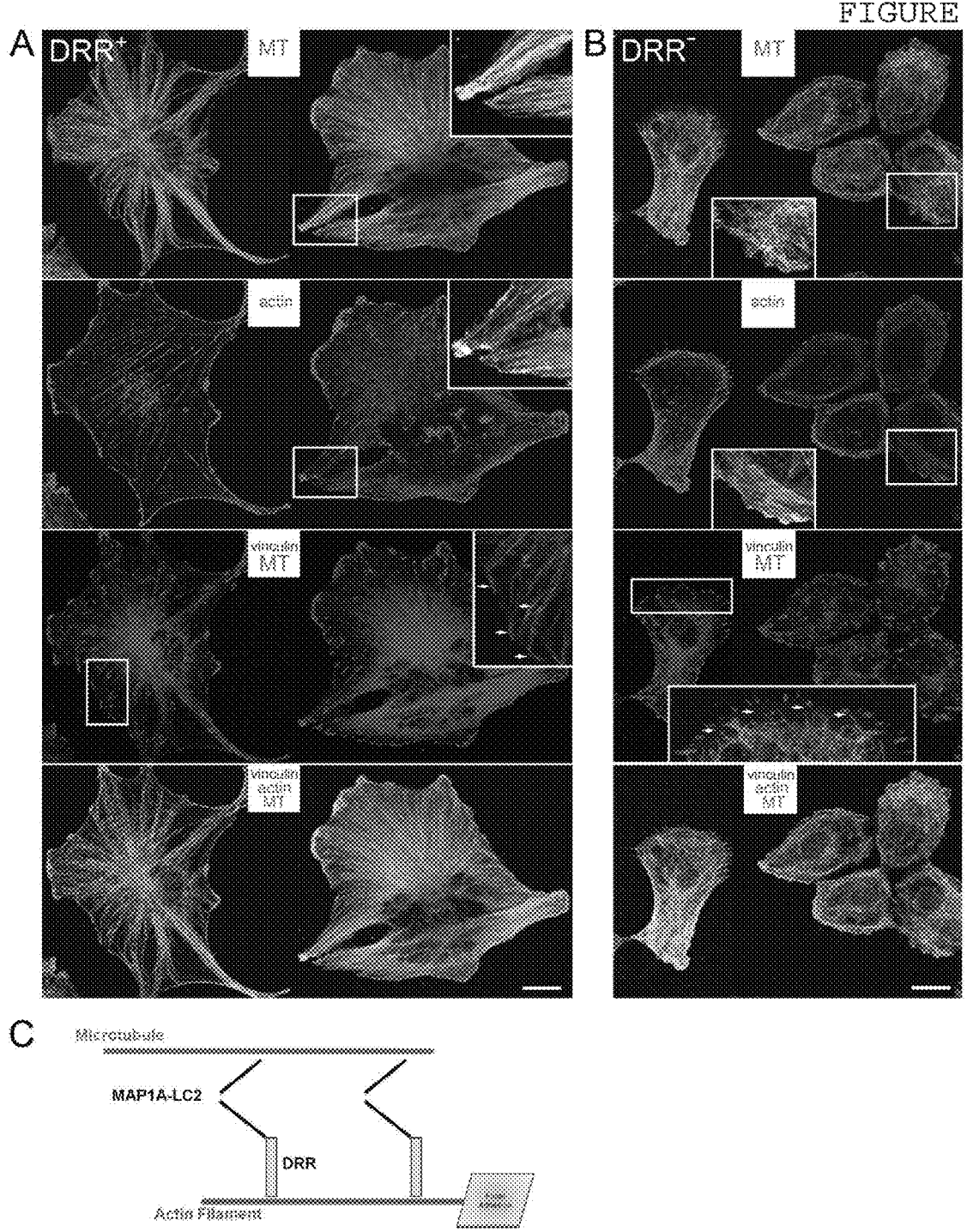
FIG. 7 shows that DRR organizes the actin and microtubular cytoskeletons. DRR+ (A) and DRR− (B) cells were grown on FN (10 µg/ml) for 48 h before fixation. Cells were then labeled for MTs (green), actin (red) and vinculin (blue). The insets represent higher magnification of the indicated outlined boxes. Arrows indicate that MTs are targeted to FAs in DRR cells, whereas MTs do not reach FAs in DRR− cells. Bars=20 µm. (C) A working model summarizing the role of DRR in cytoskeletal organization and invasion. We propose that with LC2, DRR acts as an actin-MT crosslinker. DRR targets MTs to FAs promoting their disassembly, cell rear retraction, and cell invasion.

One mechanism through which DRR could achieve this result is to alter MT dynamics by placing MTs in the vicinity of FAs (Kaverina et al., *J. Cell Biol.* 146:1033-1044, 1999). We tested this hypothesis and found that DRR regulates both the MT and actin cytoskeletons. DRR expression leads to a highly organized MT system that strongly parallels the localization pattern of the actin cytoskeleton (FIG. 7A). In contrast, DRR deficiency leads to an irregular, poorly organized MT cytoskeleton that does not parallel the actin cytoskeleton (FIG. 7B). DRR deficiency also leads to a profound change in the actin cytoskeleton with loss of stress fiber formation and the promotion of a cortical actin system (FIGS. 7 A and B). The promotion of a stress fiber actin system allows for actomyosin contraction and thus cell rear retraction (Verkhovsky et al., *J. Cell Biol.* 131:989-1002, 1995). Importantly, we also found that DRR expression is required for MTs to reach FAs. MTs in DRR deficient cells do not approach FAs (FIG. 7B). In contrast, DRR expression leads to a close association between MTs and FAs (FIG. 7A). Together, these data strongly suggest that DRR is a novel regulator of FA dynamics by controlling both the actin and MT cytoskeletons (FIG. 7C).

Reduction of DRR Expression Inhibits Human Glioma Invasion

Figure 16:
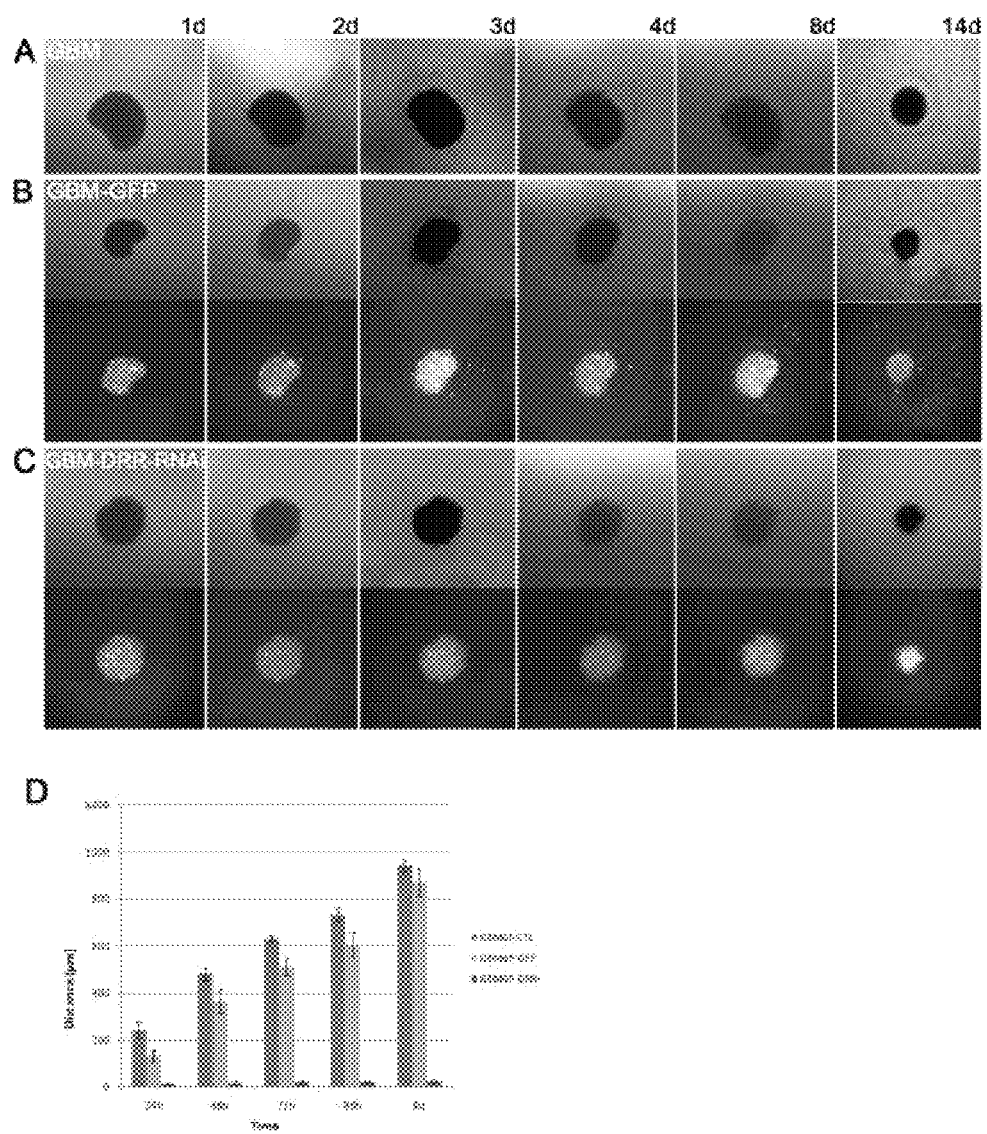
FIG. 16 shows that reduction of DRR expression inhibits human glioma invasion. Human high grade gliomas were surgically resected and immediately placed in culture. Two weeks later they were transfected with a control GFP vector or DRR-RNAi (vector also contains GFP). Tumor spheroids were generated from these cells and implanted into a collagen matrix. Brightfield (upper lanes) and fluorescence images (lower lanes) were captured at 1 to 14 days post-implantation. Non-transfected tumors (A) and control GFP-transfected tumors (B) readily invade, whereas DRR-RNAi transfected tumors (C) do not. (D) shows quantification of invasion distance from spheroid edge, wherein D indicates days, GFP is green fluorescent protein and GBM is glioblastoma (high grade glioma).

Human high grade gliomas were surgically resected and immediately placed in culture. Two weeks later they were transfected with a control GFP vector or DRR-RNAi (SEQ ID NO: 1) (vector also contains GFP). Tumor spheroids were generated from these cells and implanted into a collagen matrix. Brightfield (upper lanes) and fluorescence images (lower lanes) were captured at 1 to 14 days post-implantation (FIG. 16). Non-transfected tumors (FIG. 16A) and control GFP-transfected tumors (FIG. 16B) readily invade, whereas DRR-RNAi transfected tumors (FIG. 16C) do not. FIG. 16D shows quantification of invasion distance from spheroid edge.

These results indicate that reduction of DRR expression inhibits human glioma invasion, and represent the first demonstration of DRR as a therapeutic target to inhibit human brain cancer invasion in subjects with primary brain cancers.

Several Types of DRR Antisense Oligonucleotides Reduce DRR Expression

The efficacy of different DRR antisense oligonucleotides in reducing DRR expression was compared. Altimer oligonucleotides (oligonucleotides with alternating units; such oligos are described for example in PCT publication no. WO/2003/064441) and gapmer oligonucleotides (chimeric antisense oligonucleotides; such oligos are described for example in PCT publication no. WO/2002/20773) were tested, along with corresponding non-DRR targeting controls.

DRR+ cells were transfected with the indicated DRR antisense (Antisense G4 (SEQ ID NO: 14; an altimer), Antisense G5 (SEQ ID NO: 15; a gapmer) or Antisense G6 (SEQ ID NO: 16; a gapmer); a non-targeting control antisense (Ctl Antisense); or left untransfected (Untransfected). Oligonucleotide G1 (SEQ ID NO: 11) is a non-targeting altimer control, and oligonucleotides G2 (SEQ ID NO: 12) and G3 (SEQ ID NO: 13) are non-targeting gapmer controls.

Figure 17:
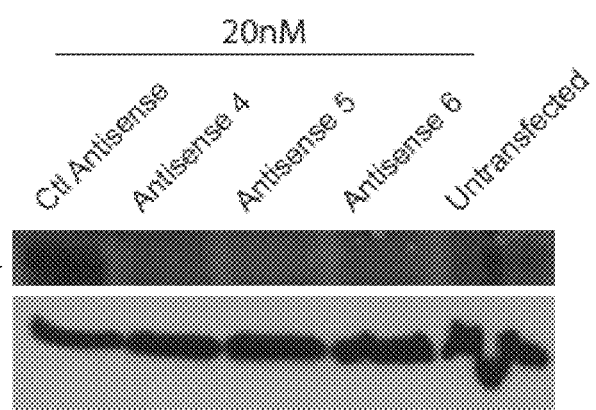
FIG. 17 shows comparison of efficacy of different DRR antisense oligonucleotides in reducing DRR expression. DRR+ cells were transfected with the indicated DRR antisense (Antisense 4 (SEQ ID NO: 14), Antisense 5 (SEQ ID NO: 15) or Antisense 6 (SEQ ID NO: 16); a non-targeting control antisense (Ctl Antisense); or left untransfected (Untransfected). 72 hours post-transfection, cells were lysed and analysed using 12% SDS-PAGE. DRR expression level was detected using an anti-DRR antibody. Western blot of tubulin is included as loading control.

DRR expression level was determined 72 hours post-transfection using Western blotting (FIG. 17). The results show that different antisense oligonucleotides are effective at reducing DRR expression.

Figure 18:
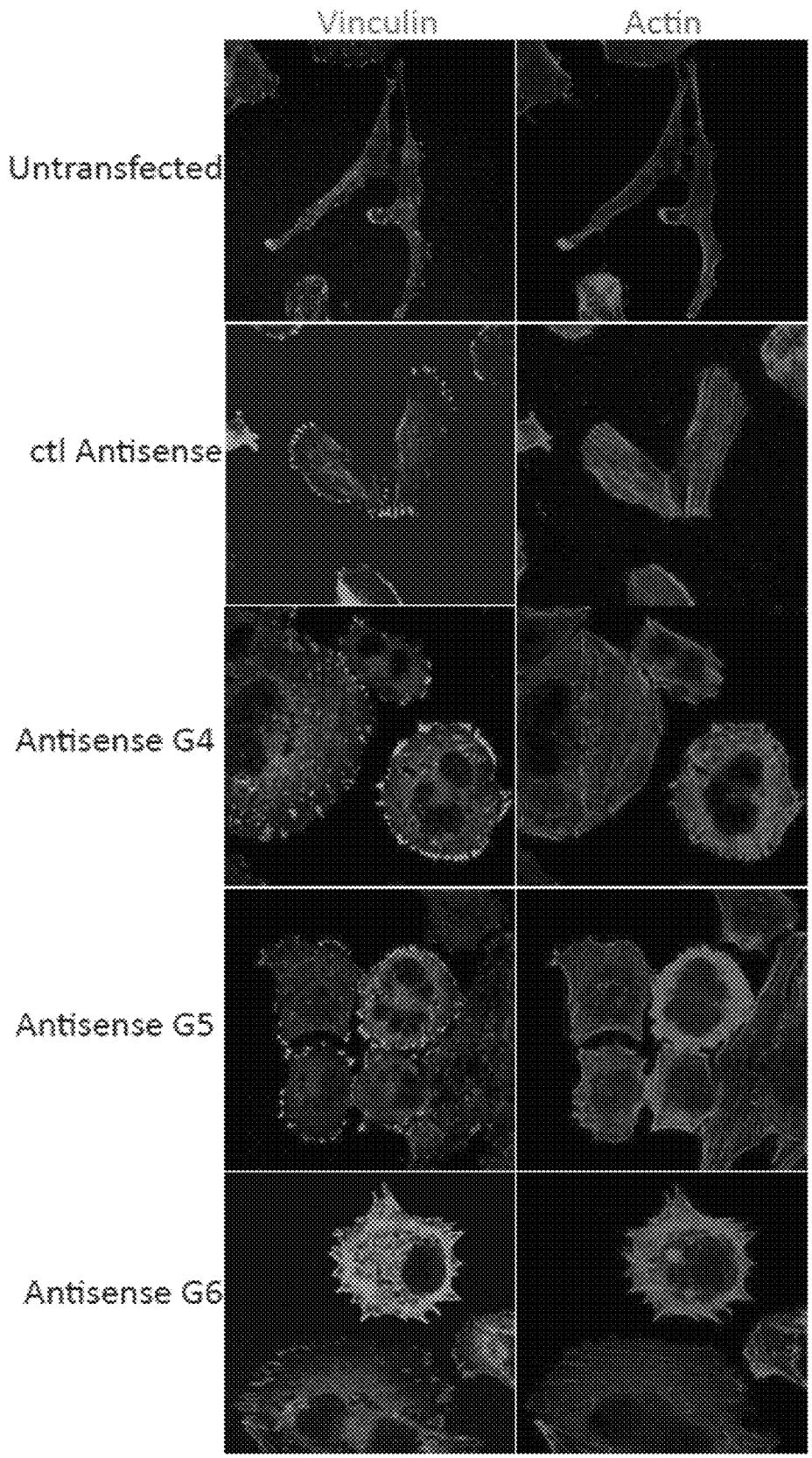
FIG. 18 shows changes in the actin cytoskeletal and focal adhesions when DRR expression is reduced. DRR+ cells were transfected with a non-targeting control antisense (ctl Antisense), the indicated DRR antisense (Antisense G4 (SEQ ID NO: 14), Antisense G5 (SEQ ID NO: 15) or Antisense G6 (SEQ ID NO: 16)) or left untransfected (Untransfected). At 72 hours, cells were fixed, counterstained, and analyzed by confocal microscopy to visualize vinculin (left column; green) and actin (right column; red).

We next looked at changes in the actin cytoskeletal and focal adhesions in DRR overexpressing cells following transfection with the different DRR antisense oligonucleotides (FIG. 18). The results show that reduction of DRR expression by treatment with DRR antisense oligonucleotides induced cells to shift from an elongated spindle morphology to a round morphology. We also found that treatment with DRR antisense oligonucleotides leads to large focal adhesions.

Figure 19A:
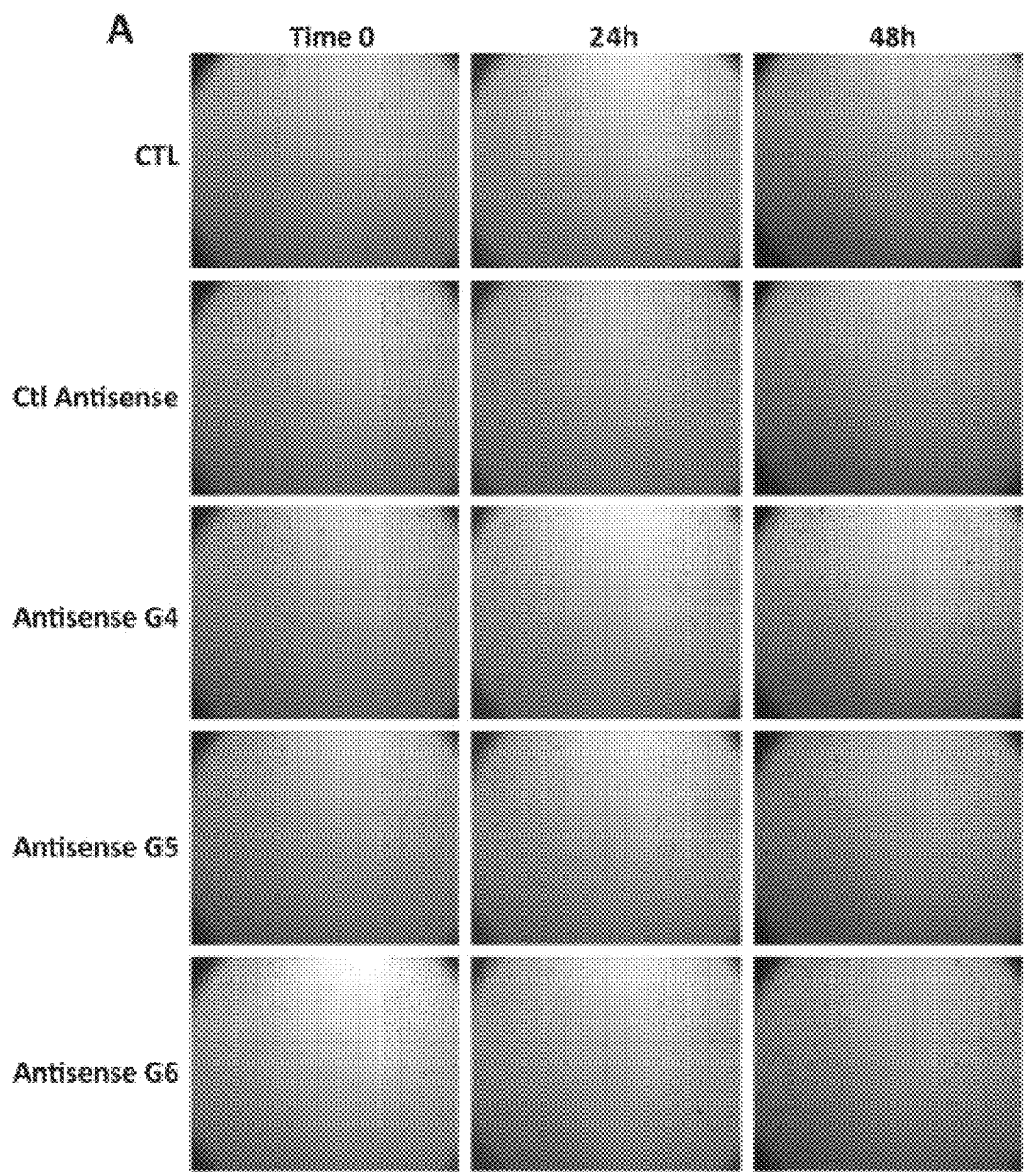
FIG. 19 shows the extent of DRR+ cell migration following reduction of DRR expression using an in vitro scratch assay. DRR+ cells were untransfected (CTL) or transfected with a non-targeting control antisense (Ctl Antisense) or transfected with the indicated antisense (antisense G4 (SEQ ID NO: 14), antisense G5 (SEQ ID NO: 15) or antisense G6 (SEQ ID NO: 16)). (A): Images from the scratch were acquired at 0, 24 hours and 48 hours; (B): Quantitative analysis of cell migration is shown; DRRCTL1 and DRRCTL2 represent untransfected, DRR+ controls. Green bar (top bar): 48 h; Red bar (center bar): 24 h; Blue bar (bottom bar): 0 h.
Figure 19B:
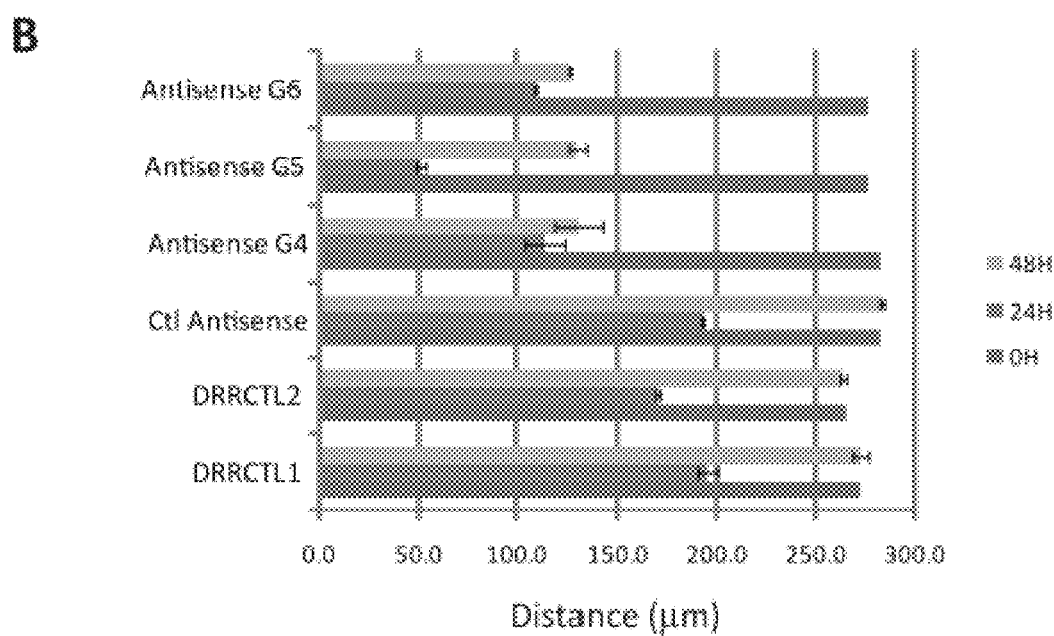

The effect of the different DRR antisense oligonucleotides on DRR+ cell migration was analyzed using an in vitro scratch assay (FIG. 19). The results show that at time zero all conditions are similar, however within 48 hours, the scratch in control DRR+ cells is no longer evident. In contrast, treatment with DRR antisense oligonucleotides prevents the gap from closing. These results demonstrate that reducing DRR expression prevents cell migration.

Figure 20A:
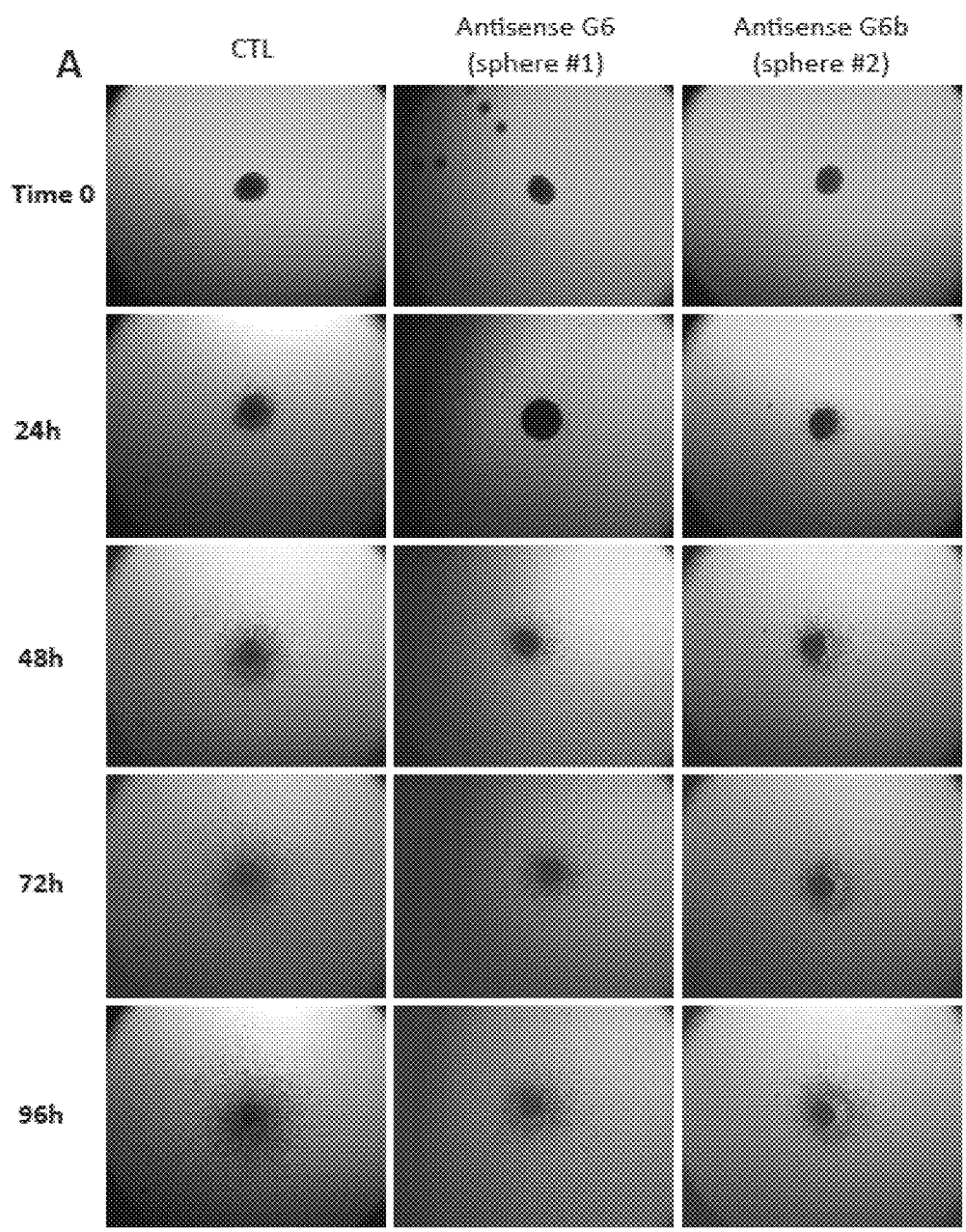
FIG. 20 shows analysis of DRR+ cell invasion following reduction of DRR expression using an in vitro 3D invasion assay. DRR+ cells were untransfected (CTL) or transfected with indicated antisense G6 (SEQ ID NO: 16). (A): Images of cell invasion were acquired at 0, 24, 48, 72 and 96 hours; G6 (sphere#1) and G6b (sphere#2) are two separate tumors treated with antisense G6. (B): Quantitative analysis of invasion is shown, where the green bars (the lefthand bar of each pair of bars) indicate CTL (control) and the red bars (the righthand bar of each pair of bars) indicate antisense G6 (SEQ ID NO: 16).
Figure 20B:
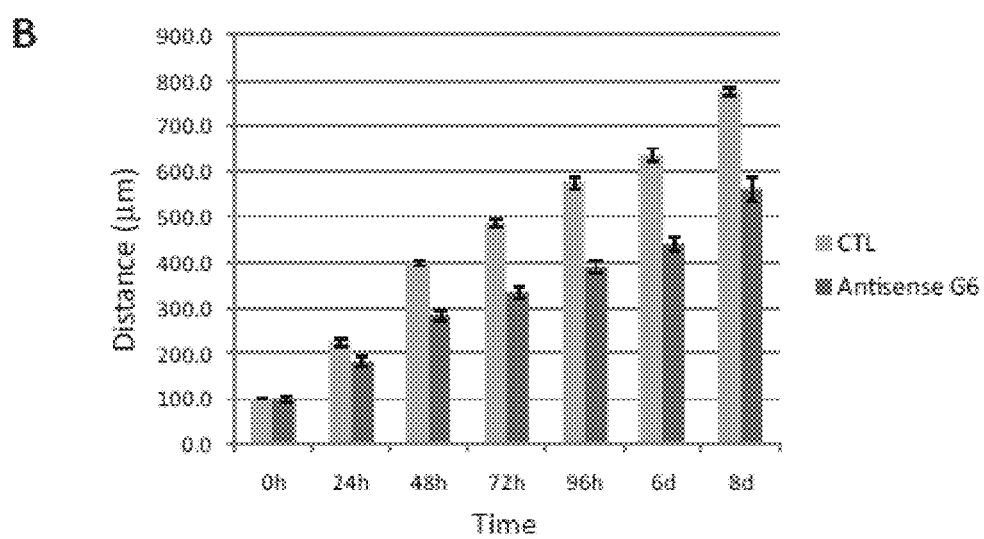

DRR+ cell invasion was also analyzed using an in vitro 3D invasion assay (FIG. 20). It can be seen that control DRR+ tumor spheroids are highly invasive whereas treatment with DRR antisense oligonucleotides impairs tumor spheroid invasion. Quantification of invasion reveals that treatment with DRR antisense oligonucleotides leads to a significant reduction in invasion (FIG. 20B).

Figure 21:
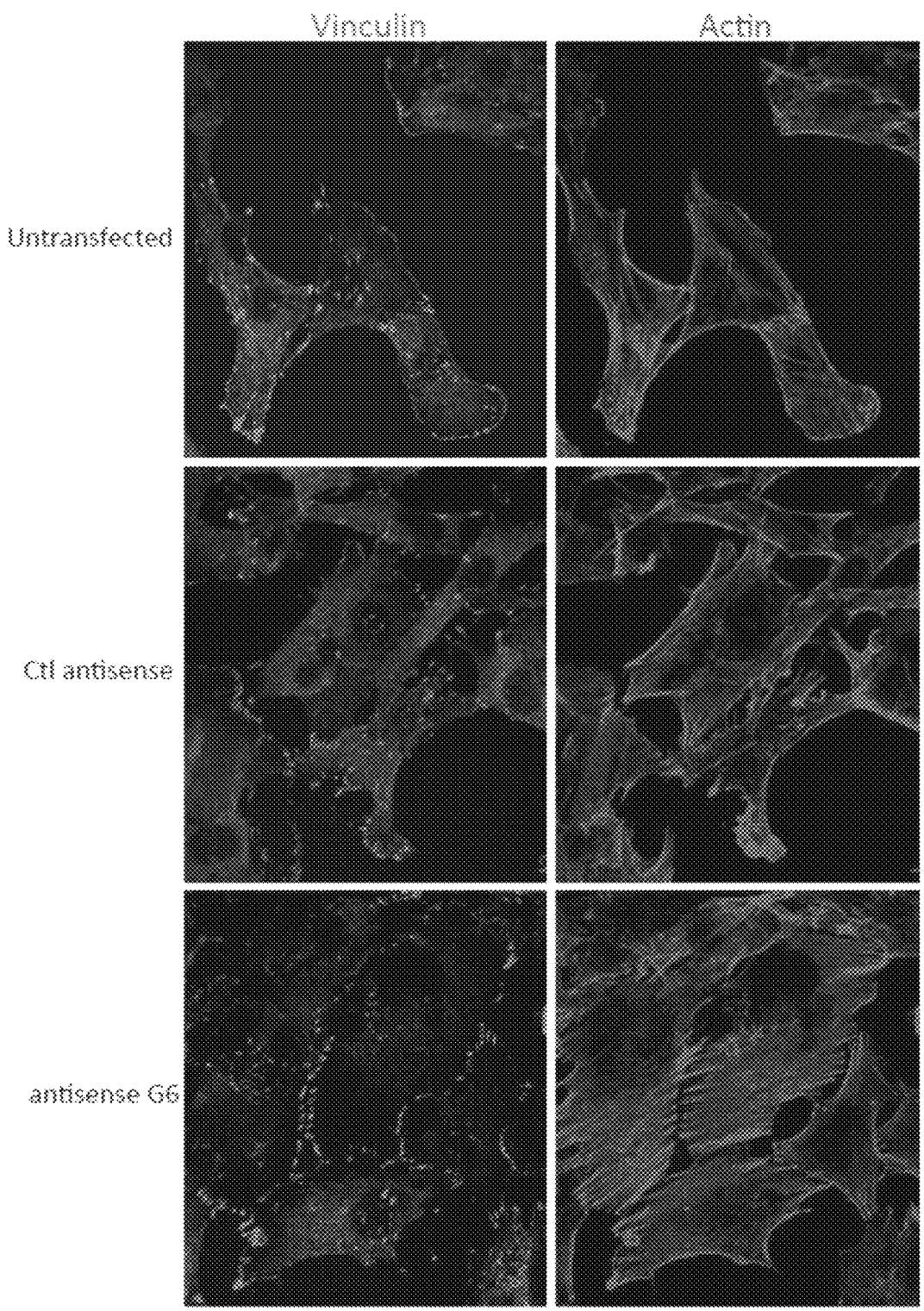
FIG. 21 shows changes in actin cytoskeletal and focal adhesions in human glioblastoma cells following reduction of DRR expression. GBM6 cells were transfected with indicated antisense (Untransfected; Ctl antisense; or antisense G6 (SEQ ID NO: 16) using lipofectamine 2000 reagent. At 72 hours, cells were fixed, counterstained, and analyzed by confocal microscopy to visualize vinculin (green; left column) and actin (red; right column).

Next, we visualized changes in the actin cytoskeletal and focal adhesions of human glioblastoma cells following transfection with the different DRR antisense oligonucleotides (FIG. 21). We found that reduction of DRR expression by treatment with DRR antisense oligonucleotides induced cells to shift from an elongated spindle morphology to a round morphology. We also found that treatment with DRR antisense oligonucleotides leads to large focal adhesions.

Human glioblastoma cell migration was analyzed using an in vitro scratch assay (FIG. 22). The results show that within 24 hours, the scratch in control glioblastoma cells has nearly closed whereas treatment with DRR antisense oligonucleotides prevents the gap from closing. These results demonstrate that reduction of DRR expression prevents glioblastoma migration.

In summary, we demonstrate herein a novel functional screening assay to identify promoters of invasion, and, using this assay, we have identified DRR as a promoter of invasion. We show here that DRR promotes MGC invasion in 3D cultures in vitro and in mouse models of invasion. Characterization of DRR expression in normal human brain and gliomas reveals that in normal brain DRR is abundantly expressed in neurons but not in glia. In contrast, DRR is uniformly and highly expressed in the invasive regions of both low and high grade gliomas, whereas its expression in the central proliferative region of high grade gliomas is variable. We also demonstrate that reduction of DRR expression inhibits human glioma invasion.

Together, these findings indicate that DRR is an important regulator of glioma invasion and a target for therapeutic treatment of glioma. In addition, DRR is a useful biomarker to delineate invasive regions and grade malignant gliomas.

We note that recent studies by others have linked DRR and malignant gliomas, reporting that DRR expression is reduced in high grade gliomas compared to low grade gliomas, while expression in normal brain was not described (van den Boom et al., *Int. J. Cancer* 119:2330-2338, 2006). An anti-proliferative function of DRR was also reported elsewhere (Wang et al., *Genes Chromosomes & Cancer* 27:1-10, 2000). In contrast to these reports of a role for DRR as a tumour suppressor, we report herein the surprising and unexpected finding that DRR acts as a driver of invasion in tumor cells and is highly expressed in the invasive regions of malignant gliomas. We show for the first time that DRR expression is associated with an invasive phenotype in glioma cells and that reduction of DRR expression inhibits human glioma invasion. Thus our results suggest for the first time a central role for DRR in glioma biology, as a driver of cell invasion as well as a regulator of cell proliferation.

The contents of all documents and references cited herein are hereby incorporated by reference in their entirety.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An antisense oligonucleotide or RNA for reducing the expression of downregulated in renal cell carcinoma (DRR) in tumor cells, comprising the nucleotide sequence:
   5' A-A-T-G-T-C-T-G-C-C-C-G-C-T-C-C-C-T-C-T 3' (SEQ ID NO: 16)
wherein said antisense oligonucleotide or RNA comprises phosphorothioate internucleotide linkages.

2. A method for treating cancer comprising administering the antisense oligonucleotide or RNA of claim 1, to a subject in need thereof.

3. The method of claim 2, wherein the antisense oligonucleotide or RNA are used in combination with one or more cancer therapies selected from the group consisting of surgical resection, chemotherapy, radiation therapy, immunotherapy, and gene therapy.

4. The method of claim 2, wherein the tumor cells are glioma cells.

5. The method of claim 4, wherein the glioma cells are glioblastoma cells.

6. A pharmaceutical composition for the treatment of cancer comprising the antisense oligonucleotide or RNA of claim 1, and a pharmaceutically acceptable carrier.

7. A method for enhancing the efficacy of a cancer therapy for the treatment of glioma, comprising administering the antisense oligonucleotide or RNA of claim 1 to a subject in need thereof, and simultaneously, separately or sequentially administrating said cancer therapy, wherein said cancer therapy is selected from the group consisting of surgical resection, chemotherapy, radiation therapy, immunotherapy, and gene therapy.

8. The method of claim 7, wherein the glioma is malignant glioblastoma.

9. A method for limiting malignant cell invasion comprising administering the antisense oligonucleotide or RNA of claim 1 to a subject in need thereof.

10. The method of claim 9, wherein malignant cell is glioma, malignant glioma or glioblastoma.

11. The antisense oligonucleotide or RNA of claim 1, wherein said antisense oligonucleotide or RNA has the sequence 5' A-A-T-G-T-C-T-G-C-C-C-G-C-T-C-C-C-T-C-T 3', wherein nucleotides shown in bold and underlined are FANA nucleotides (SEQ ID NO: 14).

12. The antisense oligonucleotide or RNA of claim 1, wherein said antisense oligonucleotide or RNA has the sequence 5' A-A-T-G-T-C-T-G-C-C-C-G-C-T-C-C-C-T-C-T 3', wherein nucleotides shown in bold and underlined are FANA nucleotides (SEQ ID NO: 15).

13. An antisense oligonucleotide or RNA for reducing the expression of downregulated in renal cell carcinoma (DRR) in tumor cells, comprising the nucleotide sequence:
   5' AATGTCTGCCCGCTCCCTCT 3' (SEQ ID NO: 16)
wherein said antisense oligonucleotide or RNA comprises at least one of the following:
   a) a sugar-modified nucleotide comprising a 2' substituent selected from the group consisting of fluorine, hydroxyl, amino, cyano, azido, —CH═CH2, —C≡CH, alkyl, functionalized alkyl, alkoxy and functionalized alkoxy groups;
   b) a modified nucleotide selected from the group consisting of: 2'O-methyl with a phosphorothioate linkage (2'O-MePS), 2'-methoxyethoxy (2'-MOE), a morpholine sugar with a phosphorodiamidate linkage (Morpholino) PMO), 2'-C, 4'-C with an oxymethylene linkage (locked nucleic acid, or LNA), N3'-P5' phosphoramidate DNA, cyclohexene nucleic acid, boranophosphate DNA, methylphosphonate DNA, and combinations thereof; or
   c) an internucleotide linkage selected from the group consisting of: phosphotriester, phosphorothioate, phosphorodithioate, boranophosphate, methylene (methylimino) (3'CH2-N(CH3)-O5'), 3'-thioformacetal (3'S—

CH2-O5'), amide (3'CH2-C(O)NH-5'), methylphosphonate, phosphoramidate (3'-OP(02)-N5'), phosphorodiamidate, oxymethylene, phosphorodiamidate, and combinations thereof; or wherein said antisense oligonucleotide or RNA is a peptide nucleic acid (PNA).

14. The antisense oligonucleotide or RNA of claim 13, wherein said antisense oligonucleotide or RNA comprises a FANA nucleotide.

15. The antisense oligonucleotide or RNA of claim 13, wherein said antisense oligonucleotide or RNA comprises a phosphorothioate internucleotide linkage.

16. The antisense oligonucleotide or RNA of claim 13, wherein said antisense oligonucleotide or RNA comprises a FANA nucleotide and a phosphorothioate internucleotide linkage.

17. A pharmaceutical composition for the treatment of cancer comprising the antisense oligonucleotide or RNA of claim 13, and a pharmaceutically acceptable carrier.

* * * * *